(12) United States Patent
Longacre et al.

(10) Patent No.: US 8,188,213 B2
(45) Date of Patent: May 29, 2012

(54) **PURIFIED POLYPEPTIDE COMPRISING OR CONSISTING OF A C-TERMINUS MSP1 ANTIGEN FROM *PLASMODIUM FALCIPARUM* CARRYING A GLYCOSYL-PHOSPHATIDYL-INOSITOL GROUP (GPI)**

(75) Inventors: Shirley Longacre, Paris (FR); Sarah Bonnet, Nantes (FR); Thierry Fontaine, Clamart (FR); Charles Roth, Rueil-Malmaison (FR); Faridabano Nato, Antony (FR)

(73) Assignee: Institut Pasteur, Paris (FR)

(*) Notice: Subject to any disclaimer, the term of this patent is extended or adjusted under 35 U.S.C. 154(b) by 1448 days.

(21) Appl. No.: 11/622,845

(22) Filed: Jan. 12, 2007

(65) Prior Publication Data
US 2010/0255038 A1 Oct. 7, 2010

Related U.S. Application Data

(63) Continuation-in-part of application No. 11/144,833, filed on Jun. 6, 2005, now Pat. No. 7,696,308, which is a continuation of application No. 09/125,031, filed as application No. PCT/FR97/00290 on Feb. 14, 1997, now Pat. No. 6,958,235.

(30) Foreign Application Priority Data

Feb. 14, 1996 (FR) ..................................... 96 01822
Jan. 13, 2006 (EP) ..................................... 06290092

(51) Int. Cl.
*A61K 38/00* (2006.01)
*C07K 14/00* (2006.01)
(52) U.S. Cl. ..................................................... 530/300
(58) Field of Classification Search .................. None
See application file for complete search history.

(56) References Cited

U.S. PATENT DOCUMENTS

| 6,958,235 B1 | 10/2005 | Longacre-Andre et al. |
| 2002/0076403 A1 | 6/2002 | Longacre-Andre et al. |
| 2007/0036818 A1 | 2/2007 | Longacre-Andre et al. |

FOREIGN PATENT DOCUMENTS

| EP | 1 529 536 A1 | 5/2005 |
| WO | WO 00/15254 | 3/2000 |

OTHER PUBLICATIONS

Egan et al. ( Infection and Immunity vol. 63, No. 2 p. 456-466, 1995).*
Schofield et al., Journal of Experimental Med. vol. 177, pp. 145-153, Jan. 1993.*

U.S. Appl. No. 12/647,674, filed Dec. 28, 2009, Longacre-Andre, et al.
U.S. Appl. No. 09/125,032, filed Mar. 12, 1999, Longacre-Andre, et al.
Shirley Longacre, Annual Report of Parasite Vaccinology for Year 2005, XP-002376623, 2005, pp. 1-2.
Udhayakumar et al, Journal of Immunology, 1995, vol. 154, pp. 6022-6030.
Longacre et al, Molecular and Biochemical Parasitology, 1994, vol. 64, pp. 191-205.
Longacre, Molecular and Biochemical Parasitology, 1995, vo. 74, pp. 105-111.
Bonnet et al, Vaccine, 2006, vol. 24, pp. 5997-6008.
Chang et al, Infection and Immunity, 1996, vol. 64, No. 1, pp. 253-261.
Altmann et al, Glycoconjugate Journal, 1999, vol. 16, pp. 109-123.
Burghaus et al, Infection and Immunity, 1996, vol. 64, No. 9, pp. 3614-3619.
Burghaus et al, Molecular and Biochemical Parasitology, 1999, vol. 104, pp. 171-183.
Darko et al, Infection and Immunity, 2005, vol. 73, No. 1, pp. 287-297.
Dutta et al, Infection and Immunity, 2001, vol. 69, No. 9, pp. 5464-5470.
Egan et al, Infection and Immunity, 1997, vol. 65, No. 8, pp. 3024-3031.
Egan et al, Infection and Immunity, 2000, vol. 63, No. 3, pp. 1418-1427.
Eisenhaber et al, BioEssays, 2003, vol. 25, pp. 367-385.
Gerold et al, Molecular and Biochemical Parasitology, 1996, vol. 75, pp. 131-143.
John et al, Journal of Immunology, 2004, vol. 173, pp. 666-672.
Kumar et al, Infection and Immunity, 2000, vol. 68, No. 4, pp. 2215-2223.
Kumar et al, Molecular Medicine, 1995, vol. 1, No. 3, pp. 325-332.
Lien et al, Nature Immunology, 2003, vol. 4, No. 12, pp. 1162-1164.
Martinez et al, Parasite Immunology, 2000, vol. 22, pp. 493-500.
Moran et al, Journal of Cell Biology, 1994, vol. 125, No. 2, pp. 333-343.
Pizarro et al, J. Mol. Biology, 2003, vol. 328, pp. 1091-1103.
Ropert et al, Current Opinion in Microbiology, 2000, vol. 3, pp. 395-403.
Smith et al, Parasitol Res, 2003, vol. 89, pp. 26-33.
Stowers et al, Infection and Immunity, 2001, vol. 69, No. 3, pp. 1536-1546.
Tine et al, Infection and Immunity, 1995, vol. 64, No. 9, pp. 3833-3844.
Wunderlich et al, Infection and Immunity, 2000, vol. 68, No. 10, pp. 5839-5845.

* cited by examiner

*Primary Examiner* — Gary B. Nickol
*Assistant Examiner* — Khattol Shahnan-Shah
(74) *Attorney, Agent, or Firm* — Oblon, Spivak, McClelland, Maier & Neustadt, L.L.P.

(57) ABSTRACT

The present invention relates to a purified polypeptide comprising or consisting of a C-terminus Merozoite Surface Protein 1 (MSP1) antigen from *Plasmodium falciparum* carrying a Glycosyl-phosphatidyl-inositol group (GPI), an immunogenic composition and a vaccine against a *Plasmodium* infection comprising said purified polypeptide.

16 Claims, 33 Drawing Sheets

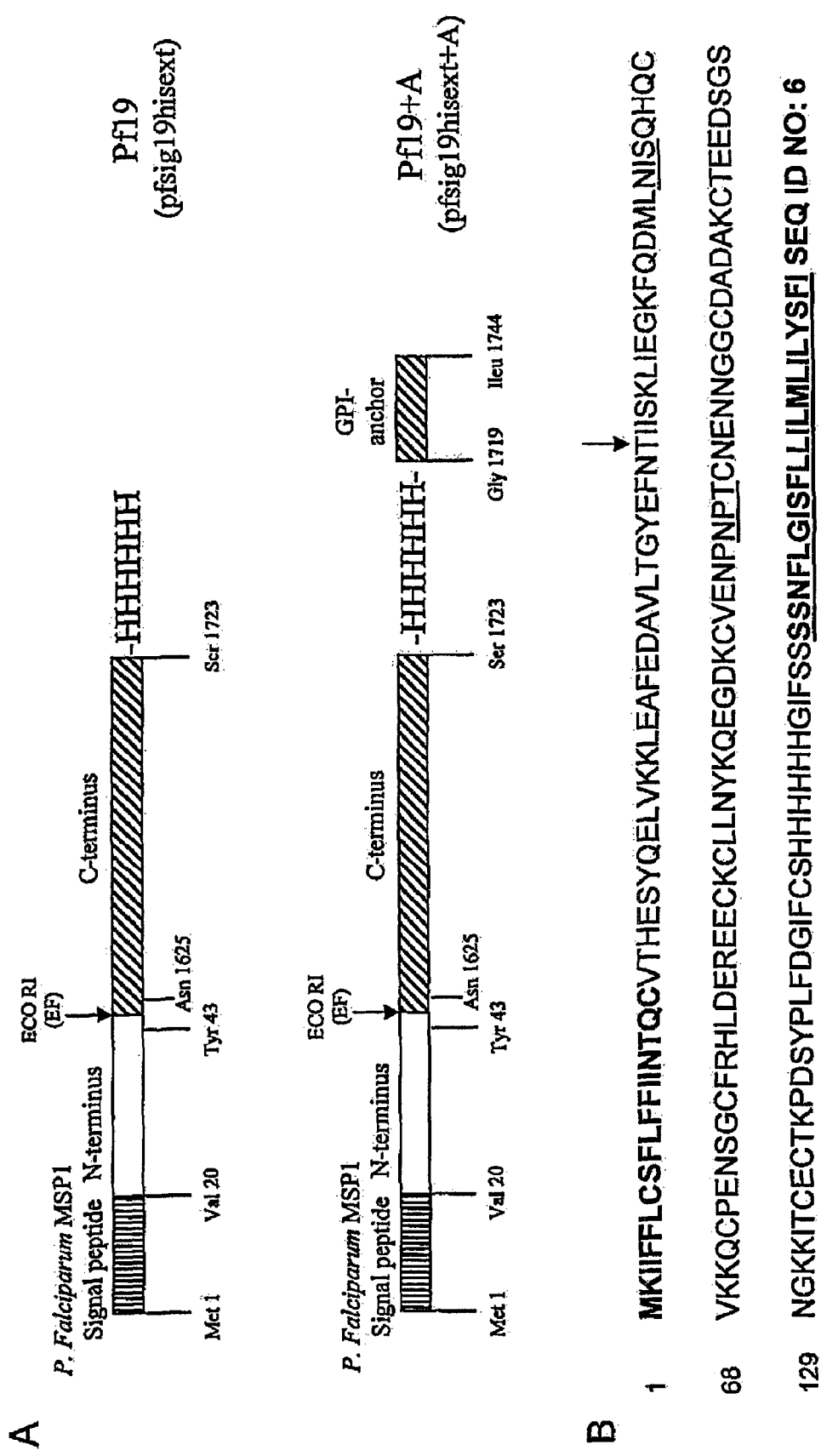
Figure 2A-B

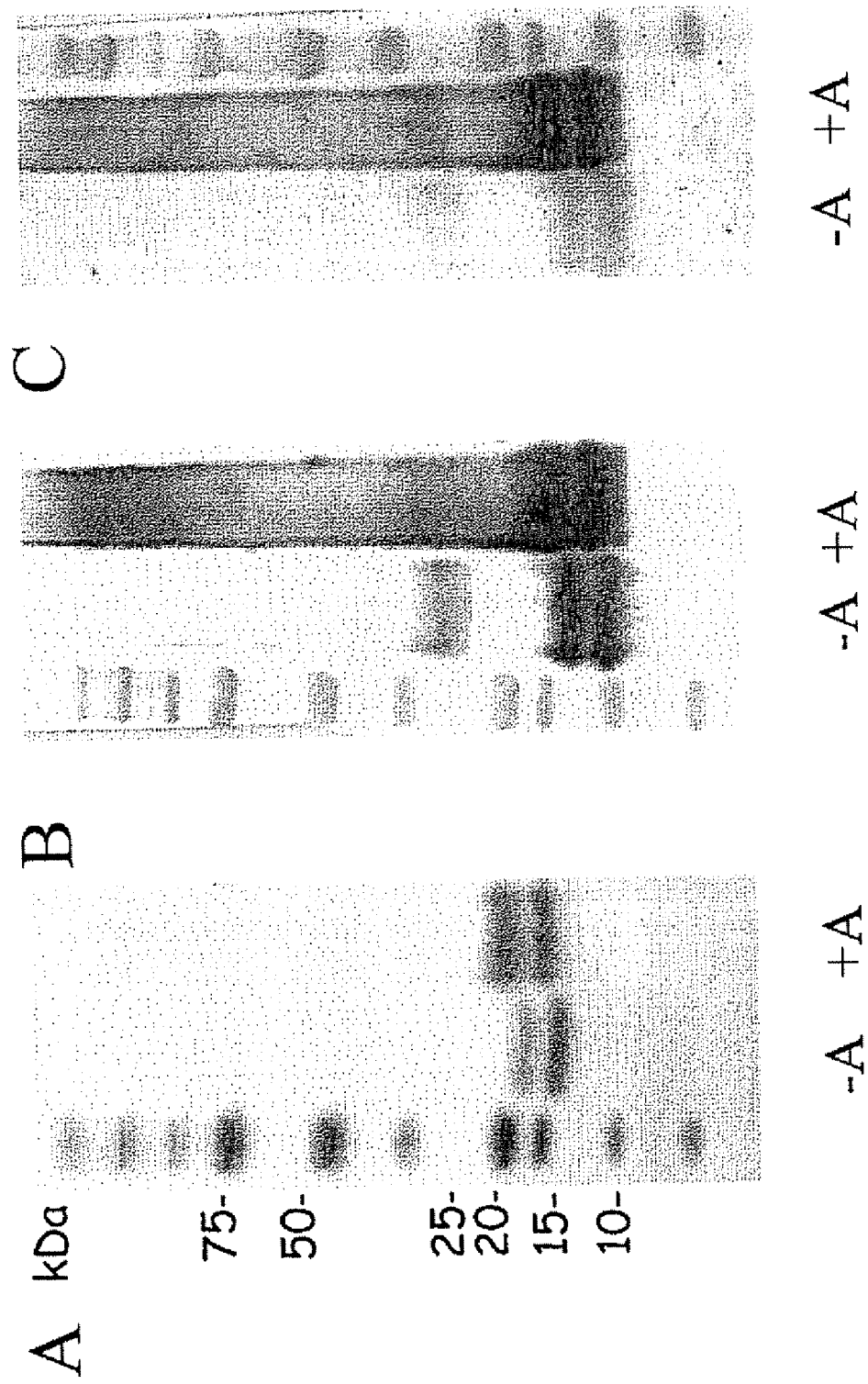
Figure 3A-C

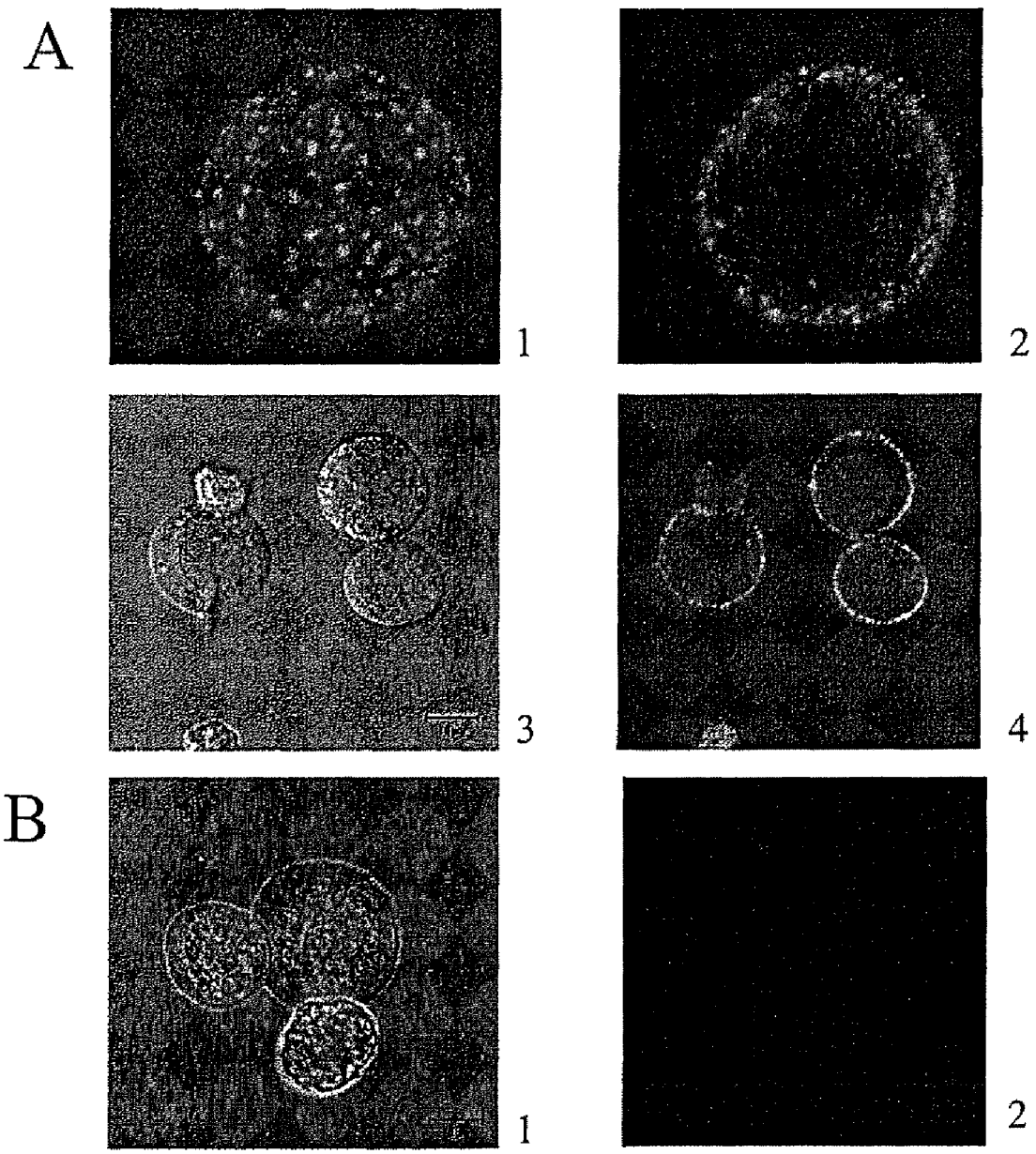
Figure 4A-B

Val Thr His Glu Ser Tyr Gln Glu Leu Val Lys Lys Leu Glu Ala Phe
1               5                   10                  15
Glu Asp Ala Val Leu Thr Gly Tyr Glu Phe Asn Thr Ile Ile Ser Lys
            20                  25                  30
Leu Ile Glu Gly Lys Phe Gln Asp Met Leu Asn Ile Ser Gln His Gln
            35                  40                  45
Cys Val Lys Lys Gln Cys Pro Glu Asn Ser Gly Cys Phe Arg His Leu
    50                  55                  60
Asp Glu Arg Glu Glu Cys Lys Cys Leu Leu Asn Tyr Lys Gln Glu Gly
65                  70                  75                  80
Asp Lys Cys Val Glu Asn Pro Asn Pro Thr Cys Asn Glu Asn Asn Gly
                85                  90                  95
Gly Cys Asp Ala Asp Ala Lys Cys Thr Glu Glu Asp Ser Gly Ser Asn
            100                 105                 110
Gly Lys Lys Ile Thr Cys Glu Cys Thr Lys Pro Asp Ser Tyr Pro Leu
    115                 120                 125
    Phe Asp Gly Ile Phe Cys Ser Gly Ile Phe Ser Ser
    130                 135                 140
                                        SEQ ID NO: 1

Figure 7A

Val Thr His Glu Ser Tyr Gln Glu Leu Val Lys Lys Leu Glu Ala Phe
1               5                   10                  15
Glu Asp Ala Val Leu Thr Gly Tyr Glu Phe Asn Thr Ile Ile Ser Lys
            20                  25                  30
Leu Ile Glu Gly Lys Phe Gln Asp Met Leu Asn Ile Ser Gln His Gln
            35                  40                  45
Cys Val Lys Lys Gln Cys Pro Glu Asn Ser Gly Cys Phe Arg His Leu
    50                  55                  60
Asp Glu Arg Glu Glu Cys Lys Cys Leu Leu Asn Tyr Lys Gln Glu Gly
65                  70                  75                  80
Asp Lys Cys Val Glu Asn Pro Asn Pro Thr Cys Asn Glu Asn Asn Gly
                85                  90                  95
Gly Cys Asp Ala Asp Ala Lys Cys Thr Glu Glu Asp Ser Gly Ser Asn
            100                 105                 110
Gly Lys Lys Ile Thr Cys Glu Cys Thr Lys Pro Asp Ser Tyr Pro Leu
    115                 120                 125
Phe Asp Gly Ile Phe Cys Ser His His His His His His Gly Ile Phe
130                 135                 140
                Ser Ser
                145
                                        SEQ ID NO: 2

Figure 7B

| | | | | | | | | | | | | | | | |
|---|---|---|---|---|---|---|---|---|---|---|---|---|---|---|---|
| atg | aag | atc | ata | ttc | ttt | ttg | tgt | tcg | ttc | ctc | ttc | ttc | atc | atc | aac | 48 |
| Met | Lys | Ile | Ile | Phe | Phe | Leu | Cys | Ser | Phe | Leu | Phe | Phe | Ile | Ile | Asn | |
| 1 | | | | 5 | | | | | 10 | | | | | 15 | | |
| acg | caa | tgt | gtg | acc | cac | gag | agc | tac | caa | gag | ctc | gtc | aag | aaa | ctg | 96 |
| Thr | Gln | Cys | Val | Thr | His | Glu | Ser | Tyr | Gln | Glu | Leu | Val | Lys | Lys | Leu | |
| | | | 20 | | | | | 25 | | | | | 30 | | | |
| gag | gcc | ttc | gag | gac | gcg | gtg | ttg | acc | ggc | tac | gaa | ttc | aac | acg | atc | 144 |
| Glu | Ala | Phe | Glu | Asp | Ala | Val | Leu | Thr | Gly | Tyr | Glu | Phe | Asn | Thr | Ile | |
| | | 35 | | | | | 40 | | | | | 45 | | | | |
| atc | tcg | aaa | ttg | atc | gag | ggc | aaa | ttc | caa | gac | atg | ttg | aac | atc | tcg | 192 |
| Ile | Ser | Lys | Leu | Ile | Glu | Gly | Lys | Phe | Gln | Asp | Met | Leu | Asn | Ile | Ser | |
| | 50 | | | | | 55 | | | | | 60 | | | | | |
| cag | cac | caa | tgc | gtg | aaa | aaa | caa | tgt | ccc | gag | aac | tct | ggc | tgt | ttc | 240 |
| Gln | His | Gln | Cys | Val | Lys | Lys | Gln | Cys | Pro | Glu | Asn | Ser | Gly | Cys | Phe | |
| 65 | | | | | 70 | | | | | 75 | | | | | 80 | |
| aga | cac | ttg | gac | gag | aga | gag | tgt | aaa | tgt | ctg | ctg | aac | tac | aaa | | 288 |
| Arg | His | Leu | Asp | Glu | Arg | Glu | Glu | Cys | Lys | Cys | Leu | Leu | Asn | Tyr | Lys | |
| | | | | 85 | | | | | 90 | | | | | 95 | | |
| cag | gag | ggc | gac | aag | tgc | gtg | gag | aac | ccc | aac | ccg | acc | tgt | aac | gag | 336 |
| Gln | Glu | Gly | Asp | Lys | Cys | Val | Glu | Asn | Pro | Asn | Pro | Thr | Cys | Asn | Glu | |
| | | | 100 | | | | | 105 | | | | | 110 | | | |
| aac | aac | ggc | ggc | tgt | gac | gca | gac | gcc | aaa | tgc | acc | gag | gag | gac | tcg | 384 |
| Asn | Asn | Gly | Gly | Cys | Asp | Ala | Asp | Ala | Lys | Cys | Thr | Glu | Glu | Asp | Ser | |
| | | 115 | | | | | 120 | | | | | 125 | | | | |
| ggc | agc | aac | ggc | aag | aaa | atc | acg | tgt | gag | tgt | acc | aaa | ccc | gac | tcg | 432 |
| Gly | Ser | Asn | Gly | Lys | Lys | Ile | Thr | Cys | Glu | Cys | Thr | Lys | Pro | Asp | Ser | |
| | 130 | | | | | 135 | | | | | 140 | | | | | |
| tac | ccg | ctg | ttc | gac | ggc | atc | ttc | tgc | agc | cac | cat | cac | cat | cac | cat | 480 |
| Tyr | Pro | Leu | Phe | Asp | Gly | Ile | Phe | Cys | Ser | His | His | His | His | His | His | |
| 145 | | | | | 150 | | | | | 155 | | | | | 160 | |
| ggc | atc | ttc | agc | agc | tcc | tct | aac | ttc | ttg | ggc | atc | tcg | ttc | ttg | ttg | 528 |
| Gly | Ile | Phe | Ser | Ser | Ser | Ser | Asn | Phe | Leu | Gly | Ile | Ser | Phe | Leu | Leu | |
| | | | | 165 | | | | | 170 | | | | | 175 | | |
| atc | ctc | atg | ttg | atc | ttg | tac | agc | ttc | att | taa | taa | SEQ ID NO: 5 | | | | 564 |
| Ile | Leu | Met | Leu | Ile | Leu | Tyr | Ser | Phe | Ile | | | SEQ ID NO: 6 | | | | |
| | | | 180 | | | | | 185 | | | | | | | | |

Figure 8

| | | | | | | | | | | | | | | | |
|---|---|---|---|---|---|---|---|---|---|---|---|---|---|---|---|
| atg | aag | gcg | cta | ctc | ttt | ttg | ttc | tct | ttc | att | ttt | ttc | gtt | acc | aaa | 48 |
| Met | Lys | Ala | Leu | Leu | Phe | Leu | Phe | Ser | Phe | Ile | Phe | Phe | Val | Thr | Lys |
| 1 | | | | 5 | | | | | 10 | | | | | 15 | |
| tgt | caa | tgt | gaa | aca | gaa | agt | tat | aag | cag | ctt | gta | gcc | aac | gtg | gac | 96 |
| Cys | Gln | Cys | Glu | Thr | Glu | Ser | Tyr | Lys | Gln | Leu | Val | Ala | Asn | Val | Asp |
| | | | 20 | | | | | 25 | | | | | 30 | | |
| gaa | ttc | ata | tta | tcc | cag | ctg | cta | aat | gtg | caa | act | cag | tta | tta | act | 144 |
| Glu | Phe | Ile | Leu | Ser | Gln | Leu | Leu | Asn | Val | Gln | Thr | Gln | Leu | Leu | Thr |
| | | | | 35 | | | | | 40 | | | | | 45 | |
| atg | agc | tcc | gag | cac | aca | tgt | ata | gac | acc | aat | gtg | cct | gat | aat | gca | 192 |
| Met | Ser | Ser | Glu | His | Thr | Cys | Ile | Asp | Thr | Asn | Val | Pro | Asp | Asn | Ala |
| | 50 | | | | | 55 | | | | | 60 | | | | |
| gcc | tgc | tat | agg | tac | ttg | gac | gga | acg | gaa | gaa | tgg | aga | tgc | ttg | tta | 240 |
| Ala | Cys | Tyr | Arg | Tyr | Leu | Asp | Gly | Thr | Glu | Glu | Trp | Arg | Cys | Leu | Leu |
| 65 | | | | | 70 | | | | | 75 | | | | | 80 |
| acc | ttt | aaa | gaa | gaa | ggc | ggc | aag | tgt | gtg | cca | gca | tcg | aat | gtg | act | 288 |
| Thr | Phe | Lys | Glu | Glu | Gly | Gly | Lys | Cys | Val | Pro | Ala | Ser | Asn | Val | Thr |
| | | | | 85 | | | | | 90 | | | | | 95 | |
| tgt | aag | gat | aac | aat | ggt | ggt | tgt | gcc | cct | gaa | gct | gaa | tgt | aaa | atg | 336 |
| Cys | Lys | Asp | Asn | Asn | Gly | Gly | Cys | Ala | Pro | Glu | Ala | Glu | Cys | Lys | Met |
| | | | | 100 | | | | | 105 | | | | | 110 | |
| acg | gac | agc | aat | aaa | atc | gtc | tgt | aaa | tgt | act | aaa | gaa | ggt | tct | gag | 384 |
| Thr | Asp | Ser | Asn | Lys | Ile | Val | Cys | Lys | Cys | Thr | Lys | Glu | Gly | Ser | Glu |
| | | | 115 | | | | | 120 | | | | | 125 | | |
| cca | ctc | ttt | gag | gga | gtt | ttc | tgt | agc | cac | cat | cac | cat | cac | cat | gga | 432 |
| Pro | Leu | Phe | Glu | Gly | Val | Phe | Cys | Ser | His | His | His | His | His | His | Gly |
| | | | 130 | | | | | 135 | | | | | 140 | | |
| gtt | ttc | tct | agc | tcc | tcc | agc | ttc | cta | agc | ttg | tcc | ttc | ttg | ttg | ctc | 480 |
| Val | Phe | Ser | Ser | Ser | Ser | Ser | Phe | Leu | Ser | Leu | Ser | Phe | Leu | Leu | Leu |
| 145 | | | | | 150 | | | | | 155 | | | | | 160 |
| atg | ttg | ctt | ttc | ctc | ctg | tgc | atg | gag | ctt | taa | taa | SEQ ID NO: 19 | | | | 516 |
| Met | Leu | Leu | Phe | Leu | Leu | Cys | Met | Glu | Leu | | | SEQ ID NO: 20 | | | |
| | | | | 165 | | | | | 170 | | | | | | |

Figure 9

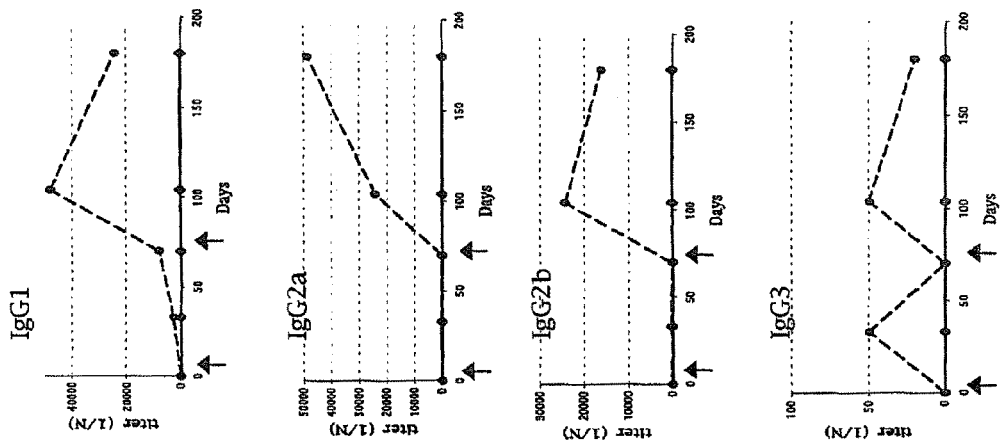
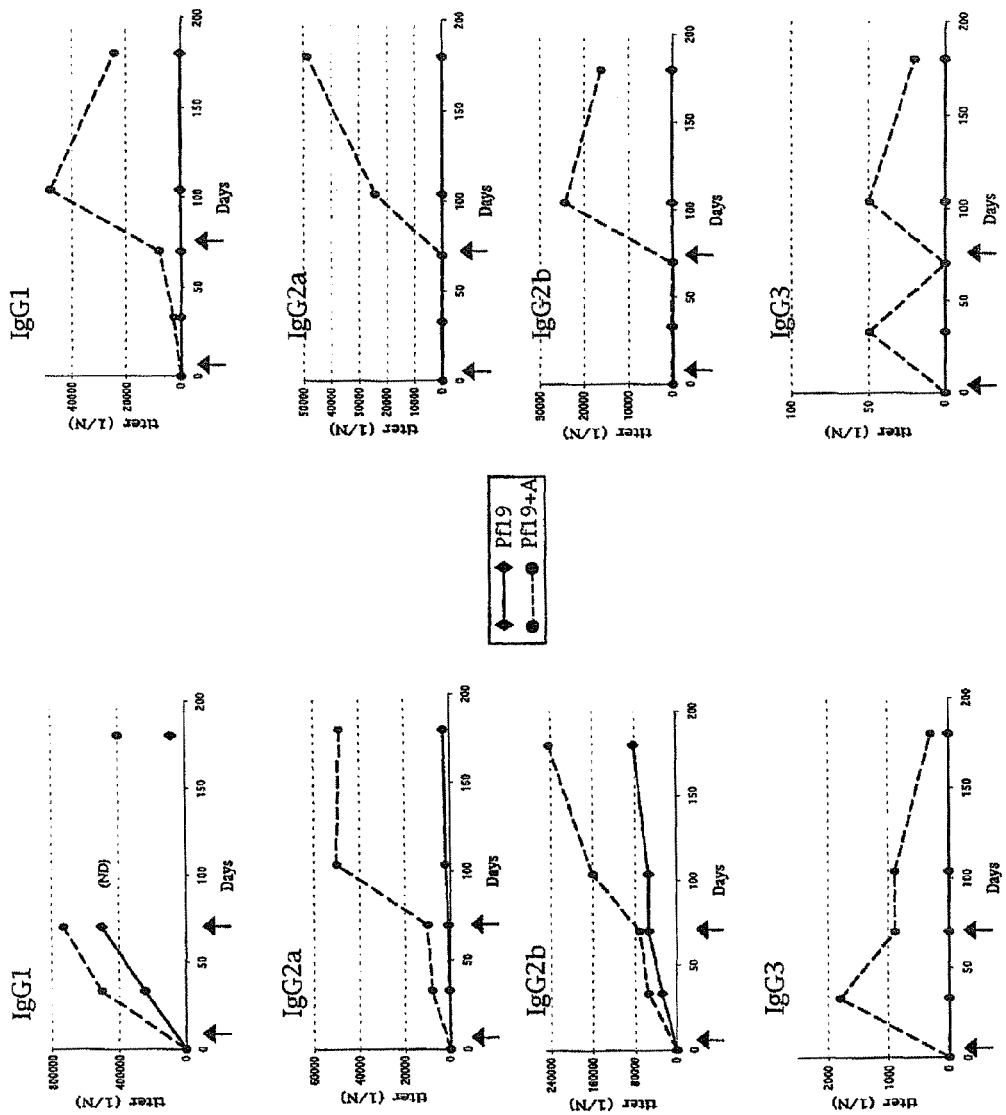
Figure 13A
Figure 13B

```
          E   F   N   I   S   Q   H   Q   C   V   K   K   Q   C   P   E   N
Bac 19   GAA TTC AAC ATC TCG CAG CAC CAA TGC GTG AAA AAA CAA TGT CCC GAG AAC
             ||| ||  ||  ||  ||| ||| ||| ||  ||| ||| ||| ||| ||  ||  ||
PF  19           AAC ATT TCA CAA CAC CAA TGC GTA AAA AAA CAA TGT CCA GAA AAT

S   G   C   F   R   H   L   D   E   R   E   E   C   K   C   L   L
Bac 19   TCT GGC TGT TTC AGA CAC TTG GAC GAG AGA GAG GAG TGT AAA TGT CTG CTG
         ||| ||  ||| ||| ||| ||  ||  ||  ||  ||| ||  ||  ||| ||| ||| |   |
PF  19   TCT GGA TGT TTC AGA CAT TTA GAT GAA AGA GAA GAA TGT AAA TGT TTA TTA

N   Y   K   Q   E   G   D   K   C   V   E   N   P   N   P   T   C
Bac 19   AAC TAC AAA CAG GAG GGC GAC AAG TGC GTG GAG AAC CCC AAC CCG ACC TGT
         ||  ||| ||| ||  ||  ||  ||  ||  ||  ||  ||  ||  ||  ||  ||  ||  |||
PF  19   AAT TAC AAA CAA GAA GGT GAT AAA TGT GTT GAA AAT CCA AAT CCT ACT TGT

N   E   N   N   G   G   C   D   A   D   A   K   C   T   E   E   D
Bac 19   AAC GAG AAC AAC GGC GGC TGT GAC GCA GAC GCC AAA TGC ACC GAG GAG GAC
         ||| ||  ||  ||  ||  ||  ||| ||  ||| ||  ||| ||| ||  ||| ||  ||  ||
PF  19   AAC GAA AAT AAT GGT GGA TGT GAT GCA GAT GCC AAA TGT ACC GAA GAA GAT

S   G   S   N   G   K   K   I   T   C   E   C   T   K   P   D   S
Bac 19   TCG GGC AGC AAC GGC AAG AAA ATC ACG TGT GAG TGT ACC AAA CCC GAC TCG
         ||  ||  ||| ||| ||  ||| ||| ||| ||  ||| ||  ||| ||  ||  |||  ||  ||
PF  19   TCA GGT AGC AAC GGA AAG AAA ATC ACA TGT GAA TGT ACT AAA CCT GAT TCT

Y   P   L   F   D   G   I   F   C   S   *   *           SEQ ID NO: 25
Bac 19   TAC CCG CTG TTC GAC GGC ATC TTC TGC AGC TAA TAA           SEQ ID NO: 24
         ||  ||  ||  ||| ||  ||  ||  ||| ||| ||
PF  19   TAT CCA CTT TTC GAT GGT ATT TTC TGC AGT                   SEQ ID NO: 26
```

Figure 15A

```
              Site Eco RI
              E   F   N   I   S   Q   H   Q   C   V   K   K   Q   C   P   E   N
Bac 19        GAA TTC AAC ATC TCG CAG CAC CAA TGC GTG AAA AAA CAA TGT CCC GAG AAC
                      |||  ||  ||  |||  |||  |||  ||  |||  |||  |||  |||  ||  ||  ||
PF 19             AAC ATT TCA CAA CAC CAA TGC GTA AAA AAA CAA TGT CCA GAA AAT S   G   C   F   R   H   L   D   E   R   E   E   C   K   C   L   L
Bac 19        TCT GGC TGT TTC AGA CAC TTG GAC GAG AGA GAG GAG TGT AAA TGT CTG CTG
              ||| ||  ||| ||| |||  ||  ||  ||  ||  |||  ||  |||  |||  |||  |   |
PF 19         TCT GGA TGT TTC AGA CAT TTA GAT GAA AGA GAA GAA TGT AAA TGT TTA TTA N   Y   K   Q   E   G   D   K   C   V   E   N   P   N   P   T   C
Bac 19        AAC TAC AAA CAG GAG GGC GAC AAG TGC GTG GAG AAC CCC AAC CCG ACC TGT
              ||  ||| ||| ||  ||  ||  ||  ||  ||  ||  ||  ||  ||  ||  ||  |||
PF 19         AAT TAC AAA CAA GAA GGT GAT AAA TGT GTT GAA AAT CCA AAT CCT ACT TGT N   E   N   N   G   G   C   D   A   D   A   K   C   T   E   E   D
Bac 19        AAC GAG AAC AAC GGC GGC TGT GAC GCA GAC GCC AAA TGC ACC GAG GAG GAC
              ||| ||  ||  ||  ||  ||  |||  ||  |||  ||  |||  |||  ||  |||  ||  ||  ||
PF 19         AAC GAA AAT AAT GGT GGA TGT GAT GCA GAT GCC AAA TGT ACC GAA GAA GAT S   G   S   N   G   K   K   I   T   C   E   C   T   K   P   D   S
Bac 19        TCG GGC AGC AAC GGC AAG AAA ATC ACG TGT GAG TGT ACC AAA CCC GAC TCG
              ||  ||  ||| ||| ||  ||| ||| ||| ||  ||| ||  ||| ||  |||  ||  ||
PF 19         TCA GGT AGC AAC GGA AAG AAA ATC ACA TGT GAA TGT ACT AAA CCT GAT TCT Y   P   L   F   D   G   I   F   C   S   S   N   F   L   G   I
Bac 19        TAC CCG CTG TTC GAC GGC ATC TTC TGC AGC TCC TCT AAC TTC TTG GGC ATC
              ||  ||  ||| |||  ||  ||  |||  |||  ||  |||  |||  |||  ||  ||  ||
PF 19         TAT CCA CTT TTC GAT GGT ATT TTC TGC AGT TCC TCT AAC TTC TTA GGA ATA S   F   L   L   I   L   M   L   I   L   Y   S   F   I   *   *       SEQ ID NO: 28
Bac 19        TCG TTC TTG TTG ATC CTC ATG TTG ATC TTG TAC AGC TTC ATT TAA TAA       SEQ ID NO: 27
              ||  ||| ||  ||  ||  |||  |||  ||  ||  ||  |||  ||  |||  |||
PF 19         TCA TTC TTA TTA ATA CTC ATG TTA ATA TTA TAC AGT TTC ATT                SEQ ID NO: 29
```

Figure 15B

```
ATG AAG GCG CTA CTC TTT TTG TTC TCT TTC ATT TTT TTC GTT ACC AAA TGT
 M   K   A   L   L   F   L   F   S   F   I   F   F   V   T   K   C

CAA TGT GAA ACA GAA AGT TAT AAG CAG CTT GTA GCC AAC GTG GAC GAA TTC
 Q   C   E   T   E   S   Y   K   Q   L   V   A   N   V   D   E   F

AAC ATC TCG CAG CAC CAA TGC GTG AAA AAA CAA TGT CCC GAG AAC TCT GGC
 N   I   S   Q   H   Q   C   V   K   K   Q   C   P   E   N   S   G

TGT TTC AGA CAC TTG GAC GAG AGA GAG GAG TGT AAA TGT CTG CTG AAC TAC
 C   F   R   H   L   D   E   R   E   E   C   K   C   L   L   N   Y

AAA CAG GAG GGC GAC AAG TGC GTG GAG AAC CCC AAC CCG ACC TGT AAC GAG
 K   Q   E   G   D   K   C   V   E   N   P   N   P   T   C   N   E

AAC AAC GGC GGC TGT GAC GCA GAC GCC AAA TGC ACC GAG GAG GAC TCG GGC
 N   N   G   G   C   D   A   D   A   K   C   T   E   E   D   S   G

AGC AAC GGC AAG AAA ATC ACG TGT GAG TGT ACC AAA CCC GAC TCG TAC CCG
 S   N   G   K   K   I   T   C   E   C   T   K   P   D   S   Y   P

CTG TTC GAC GGC ATC TTC TGC AGC TAA TAA       SEQ ID NO: 30
 L   F   D   G   I   F   C   S   *   *        SEQ ID NO: 31
```

Figure 15C

```
GAA ACA GAA AGT TAT AAG CAG CTT GTA GCC AAC GTG GAC GAA TTC
 E   T   E   S   Y   K   Q   L   V   A   N   V   D   E   F

AAC ATC TCG CAG CAC CAA TGC GTG AAA AAA CAA TGT CCC GAG AAC TCT GGC
 N   I   S   Q   H   Q   C   V   K   K   Q   C   P   E   N   S   G

TGT TTC AGA CAC TTG GAC GAG AGA GAG GAG TGT AAA TGT CTG CTG AAC TAC
 C   F   R   H   L   D   E   R   E   E   C   K   C   L   L   N   Y

AAA CAG GAG GGC GAC AAG TGC GTG GAG AAC CCC AAC CCG ACC TGT AAC GAG
 K   Q   E   G   D   K   C   V   E   N   P   N   P   T   C   N   E

AAC AAC GGC GGC TGT GAC GCA GAC GCC AAA TGC ACC GAG GAG GAC TCG GGC
 N   N   G   G   C   D   A   D   A   K   C   T   E   E   D   S   G

AGC AAC GGC AAG AAA ATC ACG TGT GAG TGT ACC AAA CCC GAC TCG TAC CCG
 S   N   G   K   K   I   T   C   E   C   T   K   P   D   S   Y   P

CTG TTC GAC GGC ATC TTC TGC AGC TAA TAA           SEQ ID NO: 32
 L   F   D   G   I   F   C   S   *   *            SEQ ID NO: 33
```

Figure 15D

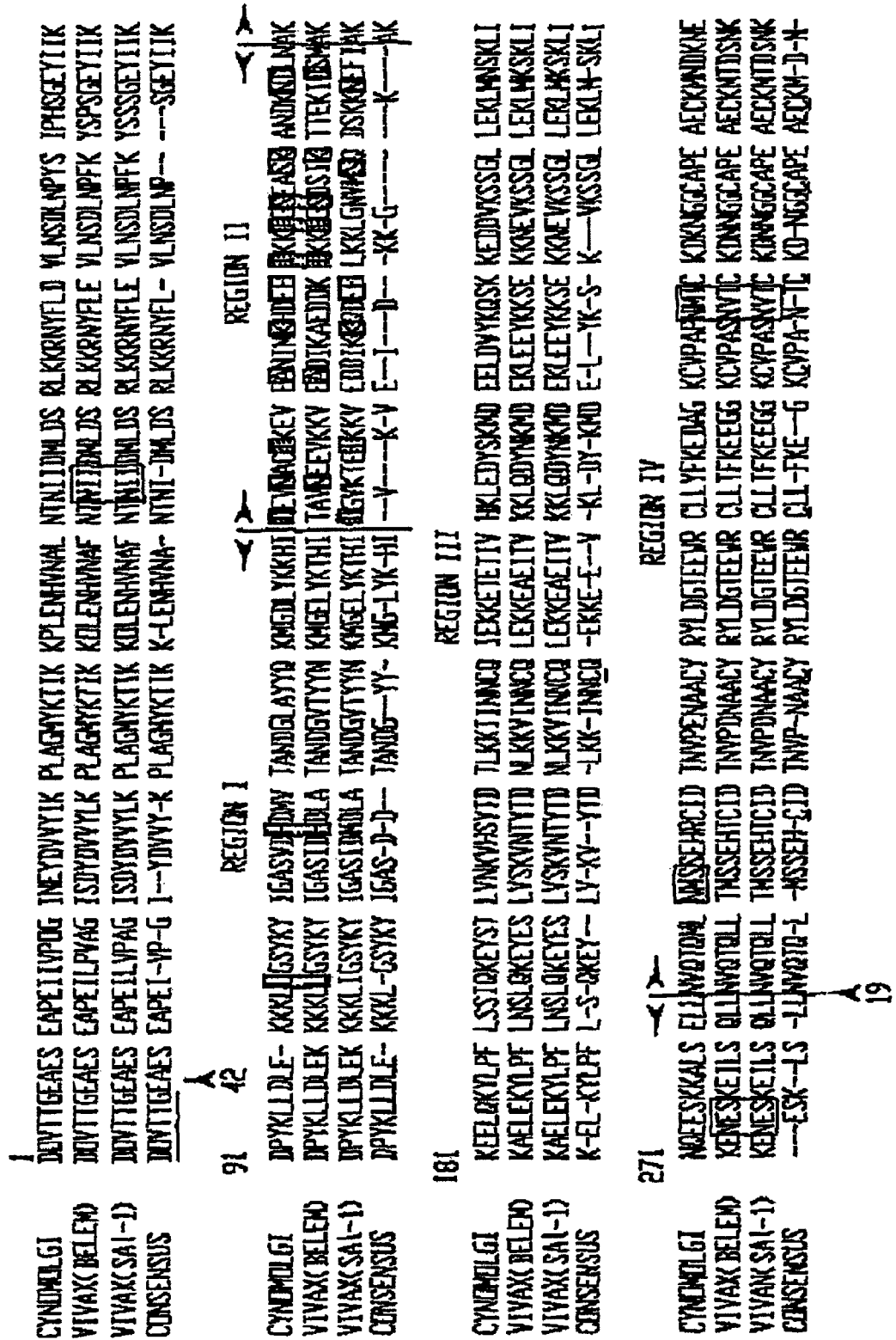
Figure 18A.1

```
            361
CYNOMOLGI     IVCKCTKEGS EPLFEGVFCS     SEQ ID NO: 34
VIVAX(BELEM)  IVCKCTKEGS EPLFEGVFCS     SEQ ID NO: 35
VIVAX(SAL-1)  IVCKCTKEGS EPLFEGVFCS     SEQ ID NO: 36
CONSENSUS     IVCKCTKEGS EPLFEGVFCS     SEQ ID NO: 37
```

Figure 18A.2

PURIFIED POLYPEPTIDE COMPRISING OR CONSISTING OF A C-TERMINUS MSP1 ANTIGEN FROM *PLASMODIUM FALCIPARUM* CARRYING A GLYCOSYL-PHOSPHATIDYL-INOSITOL GROUP (GPI)

CROSS-REFERENCE TO RELATED APPLICATIONS

This application is a Continuation-In-Part of U.S. Ser. No. 11/144,833 filed on Jun. 6, 2005, which issued as U.S. Pat. 7,696,308 B2 on Apr. 14, 2010, which is a Continuation of U.S. Ser. No. 09/125,031 filed on Mar. 10, 1999, which issued as U.S. Pat. No. 6,958,235 B1 on Oct. 25, 2005, which is a national stage of PCT/FR97/00290 filed on Feb. 14, 1997, which claims priority of FR 96/01822 filed on Feb. 14, 1996. This application also claims priority to 06 290 092.3 filed on Jan. 13, 2006.

TECHNICAL FIELD OF THE INVENTION

The invention relates to novel active principles for vaccines derived from the major surface protein in merozoite forms of a *Plasmodium* which is infectious for mammals, especially humans, more generally termed MSP-1.

The present invention relates to a purified polypeptide comprising or consisting of a C-terminus MSP1 antigen from *Plasmodium falciparum* carrying a Glycosyl-phosphatidyl-inositol group (GPI), an immunogenic composition and a vaccine against a *Plasmodium* infection comprising said purified polypeptide.

The present invention also relates to a nucleic acid molecule which encodes the amino acid sequence of said purified polypeptide, an expression vector and an expression system for the expression of said purified polypeptide.

BACKGROUND OF THE INVENTION

Malaria is the world's most important parasitic infectious disease, in terms of the number of exposed and infected individuals. It causes an estimated 2-3 million deaths per year, primarily among children under 5 years old in Africa, and constitutes a heavy economic burden in affected communities. Among the four species of *Plasmodium* responsible for human malaria, *Plasmodium falciparum* causes by far the most morbidity and mortality. The rapidly-increasing incidence of drug-resistant parasite strains, as well as insecticide-resistant mosquito vectors, have drastically increased the urgency of producing an effective vaccine to combat this wide spread plague of poverty. The asexual blood stage of the *Plasmodium* life cycle is responsible for the clinical symptoms and pathology of malaria. The extra-cellular merozoite is the infectious form of the parasite for red blood cells, and its surface proteins are obvious vaccine candidates, since many are likely to play essential roles in the erythrocyte invasion process, and they are accessible targets for humoral immune system effectors (antibodies and complement).

MSP-1 has already been the subject of a number of studies. It is synthesized in the schizont stage of *Plasmodium* type parasites, in particular *Plasmodium falciparum*, and is expressed in the form of one of the major surface constituents of merozoites both in the hepatic stage and in the erythrocytic stage of malaria (1, 2, 3, 4). Because of the protein's predominant character and conservation in all known *Plasmodium* species, it has been suggested that it could be a candidate for constituting anti-malarial vaccines (5, 6).

The same is true for fragments of that protein, particularly the natural cleavage products which are observed to form, for example during invasion by the parasite into erythrocytes of the infected host. Among such cleavage products are the C-terminal fragment with a molecular weight of 42 kDa (7, 8) which is itself cleaved once more into an N-terminal fragment with a conventional apparent molecular weight of 33 kDa and into a C-terminal fragment with a conventional apparent molecular weight of 19 kDa (9) which remains normally fixed to the parasite membrane after the modifications carried out on it, via glycosylphosphatidylinositol (GPI) groups (10, 11).

It is also found at the early ring stage of the intraerythrocytic development cycle (15, 16), whereby the observation was made that the 19 kDa fragment could play a role which is not yet known, but which is doubtless essential in re-invasive processes. This formed the basis for hypotheses formed in the past that that protein could constitute a particularly effective target for possible vaccines.

Among the most promising blood stage vaccine candidates is the major merozoite surface protein 1 (MSP1), which has been studied most extensively in *Plasmodium falciparum*, although homologues exist for all other *Plasmodium* species studied, such as for *Plasmodium vivax* for example. It is synthesized during schizogony as a 185-215 kDa protein (depending on the species), which is attached to the merozoite plasma membrane by a C-terminal glycosyl-phosphatidyl-inositol (GPI) moiety [1]. During merozoite maturation. MSP1 undergoes two successive proteolytic cleavages, giving rise to an 11 kDa C-terminal peptide, known as MSP1p19 due to its migration on SDS-PAGE. MSP1p19 with its GPI anchor is the only part of MSP1 remaining on the merozoite in newly invaded erythrocytes [2] reviewed in [3]. The precise function(s) of MSP1 and/or MSP1p19, although unknown, appear to be essential for erythrocyte invasion and parasite survival, since no viable parasites can be recovered following MSP1 knock-out, although surprisingly. PfMSP1p19 can be complemented by its *P. chabaudi* homologue [4]. Unlike many polymorphic *Plasmodium* merozoite surface proteins [5], PfMSP1p19 is highly conserved in parasites from diverse geographical locations [6]; [7]; [8]; [9], a feature with obvious advantages for a vaccine candidate. MSP1p19 in all species is highly cysteine rich and is composed essentially of two tandem, closely associated epidermal growth factor-like domains. Although the amino acid sequence of MSP1p19 varies considerably among different *Plasmodium* species, its 3-dimentional structure appears to be remarkably conserved [10]; [11]. Indeed its function appears to depend exclusively on its structure than to any given amino acid sequence [4].

It should be understood that the references frequently made below to the p42 and p19 proteins from a certain type of *Plasmodium* are understood to refer to the corresponding C-terminal cleavage products of the MSP-1 protein of that *Plasmodium* or, by extension, to products containing substantially the same amino acid sequences, obtained by genetic recombination or by chemical synthesis using conventional techniques, for example using the "Applied System" synthesizer, or by "Merrifield" type solid phase synthesis. For convenience, references to "recombinant p42" and "recombinant p19" refer to "p42" and "p19" obtained by techniques comprising at least one genetic engineering step.

Faced with the difficulty of obtaining large quantities of parasites for *P. falciparum* and the impossibility of cultivating *P. vivax* in vitro, it has become clear that the only means of producing an anti-malaria vaccine is to resort to techniques which use recombinant proteins or peptides. However. MSP-1 is very difficult to produce whole because of it large size of about 200 kDa, a fact which has led researchers to study the C-terminal portion, the (still unknown) function of which is probably the more important.

Recombinant proteins concerning the C-terminal portion of the *P. falciparum* MSP-1 which have been produced and tested in the monkey (12, 40, 41) are:
- a p19 fused with a glutathione-S-transferase produced in *E. coli* (40);
- a p42 fused with a glutathione-S-transferase produced in *E. coli* (12);
- a p19 fused with a polypeptide from a tetanic anatoxin and carrying auxiliary T cell epitopes produced in *S. cerevisiae* (12);
- a p42 produced in a baculovirus system (41).

A composition containing a p19 protein fused with a glutathione-S-transferase produced in *E. coli* combined with alum or liposomes did not exhibit a protective effect in any of six vaccinated *Aotus nancymai* monkeys (40).

A composition containing a p42 protein fused with a glutathione-S-transferase produced in *E. coli* combined with Freunds complete adjuvant did not exhibit a protective effect in two types of *Aotus* monkeys (*A. nancymai* and *A. vociferans*) when administered to them. The p19 protein produced in *S. cerevisiae* exhibited a protective effect in two *A. nancymai* type *Aotus* monkeys (12). In contrast, there was no protective effect in two *A. vociferans* type *Aotus* monkeys.

Some researchers (18) have also reported immunization tests carried out in the rabbit using a recombinant p42 protein produced in a baculovirus system and containing one amino acid sequence in common with *P. falciparum* (18). Thus these latter authors indicate that in the rabbit that recombinant p42 behaves substantially in the same way as the entire recombinant MSP-1 protein (gp195). This p42 protein in combination with Freunds complete adjuvant has been the subject matter of a vaccination test in a non-human primate susceptible to infection by *P. falciparum, Aotus*, lemurinus grisemembra (40). The results showed that 2 of 3 animals were completely protected and the third, while exhibiting a parasitemia which resembled that of the controls, had a longer latent period. It is nevertheless risky to conclude to a protective nature in man of the antibodies thus induced against the parasites themselves. It should be remembered that there are currently no very satisfactory experimental models in the primate for *P. vivax* and *P. falciparum*. The Saimiri model, developed for *P. falciparum* and *P. vivax*, and the *Aotus* model for *P. falciparum*, are artificial systems requiring the parasite strains to be adapted and often requiring splenectomy of the animals to obtain significant parasitemia. As a result, the vaccination results from such models can only have a limited predictive value for man.

In any event, what the real vaccination rate would be which could possibly be obtained with such recombinant proteins is also questionable, bearing in mind the discovery—reported below—of the presence in p42s from *Plasmodiums* of the same species, and more particularly in the corresponding p33s, of hypervariable regions which would in many cases render uncertain the immunoprotective efficacy of antibodies induced in individuals vaccinated with a p42 from a *Plasmodium* strain against an infection by other strains of the same species (13).

It can even be assumed that the high polymorphism of the N-terminal portion of p42 plays a significant role in immune evasion, often observed for that type of parasite.

The aim of the invention is to produce vaccinating recombinant proteins which can escape these difficulties, the protective effect of which is verifiable in genuinely significant experimental models or is even directly in man.

More particularly, the invention provides vaccinating compositions against a *Plasmodium* type parasite which is infectious for man, containing as an active principle a recombinant protein which may or may not be glycosylated, whose essential constituent polypeptide sequence is:
- either that of a 19 kilodalton (p19) C-terminal fragment of the surface protein 1 of the merozoite form {MSP-1 protein) of a *Plasmodium* type parasite which is infectious for man, said C-terminal fragment remaining normally anchored to the parasite surface at the and of its penetration phase into human erythrocytes in the event of an infectious cycle;
- or that of a portion of that fragment which is also capable of inducing an immune response which can inhibit in vivo parasitemia due to the corresponding parasite;
- or that of an immunologically equivalent peptide of said p19 fragment or said portion of that fragment; and said recombinant protein further comprises conformational epitopes which are unstable in a reducing medium and which constitute the majority of the epitopes recognized by human antiserums formed against the corresponding *Plasmodium*.

The presence of such conformational epitopes plays an important role in the protective efficacy of the active principle of the vaccines. They are particularly found in the active principles which exhibit the other characteristics defined above, when they are produced in a baculovirus system. If need be, it is mentioned below that the expression "baculovirus vector system" means the ensemble constituted by the baculovirus type vector itself and the cell lines, in particular cells of insects transfectable by a baculovirus modified by a sequence to be transferred to these cell lines resulting in expression of that transferred sequence. Preferred examples of these two partners in the baculovirus system have been described in the article by Longacre et al. (14). The same system was used in the examples below. It goes without saying, of course, that variations in the baculovirus and in the cells which can be infected by the baculovirus can be used in place of those selected.

In particular, the recombinant protein is recognized by human antiserums formed against the corresponding *Plasmodium* or against a homologous *Plasmodium* when it is in its non reduced state or in a reduced non irreversible state, but is not recognized or is only recognized to a slight extent by these same antiserums when it is irreversibly reduced.

The unstable character of these conformational epitopes in a reducing medium can be demonstrated by the test described below in the examples, in particular in the presence of β-mercaptoethanol. Similarly, the examples below describe the experimental conditions applicable to obtain irreversible reduction of the proteins of the invention.

From this viewpoint, the recombinant protein produced by Longacre et al. (14) can be used in such compositions. It should be remembered that S. Longacre et al. succeeded in producing a recombinant p19 from the MSP-1 of *P. vivax* in a baculovirus vector system containing a nucleotide sequence coding for the p19 of *Plasmodium vivax*, in particular by transfecting cultures of insect cells [*Spodoptera frugiperda* (Sf9) line] with baculovirus vectors containing, under the control of the polyhedrin promoter, a sequence coding for the peptide sequences defined below, with the sequences being placed in the following order in the baculovirus vector used:
- a 35 base pair 5' terminal fragment of the polyhedrin signal sequence, in which the methionine codon for initiating expression of this protein had been mutated (to ATT);

a 5'-terminal nucleotide fragment coding for a 32 amino acid peptide corresponding to the N-terminal portion of MSP-1, including the MSP-1 signal peptide;

either a nucleotide sequence coding for p19, or a sequence coding for the p42 of the MSP-1 protein of *Plasmodium vivax*, depending on the case, these sequences also being provided with ("anchored" forms) or deprived of (soluble forms) 3' end regions of these nucleotide sequences, whose end C-terminal expression products are reputed to play an essential role in anchoring the final p19 protein to the parasite membrane;

2 TAA stop codons.

For p42, the sequences derived from the C-terminal region of MSP-1 extend consequently from amino acid Asp 1325 to amino acid Leu 1726 (anchored form) or to amino acid Ser 1705 (soluble form) and for p19, the sequences extend from amino acid Ile 1602 to amino acid Leu 1726 (anchored form) or to amino acid Ser 1705 (soluble form) it being understood that the complete amino acid sequences of p42 and p19, whose initial and terminal amino acids have been indicated above follow from the gene of the Belem isolate of *P. vivax* which has been sequenced (20).

In studies carried out in endemic regions, PfMSP1p19 specific antibodies in the sera of exposed individuals have been associated with protection against high levels of parasitemia and clinical episodes [12]; [13]; [14]; [15]; [16]; [17]. In addition, anti-MSP1 antibodies in human immune sera have been shown to inhibit parasite growth in vitro [18]. More importantly, using transfected *P. falciparum* and *P. chabaudi* parasite lines with reciprocal allelic replacements of their divergent MSP1p19 gene sequences (43% homology), O'Donnell et al. [19] could show that antibodies specific for this domain in *P. falciparum* immune human sera or *P. chabaudi* immune mice, represented a major component of the growth inhibition, or invasion inhibitory responses in parasite cultures.

Several vaccination trials have been carried out in primate models using varying recombinant versions of C-terminal MSP1 (p42 and/or p19) in association with a number of different adjuvants, which have provided some indication of parameters that may be important for protective efficacy. None of the C-terminal PfMSP1 recombinant proteins expressed in *E. coli* have shown evidence of protective efficacy in primates [20]; [21]; [22]). Protective efficacy conferred by yeast recombinant versions of PfMSP1p19 has been highly inconsistent, depending on the subspecies of *Aotus* used [20], the challenge dose of infected red blood cells [23], and the exact nature of the recombinant construct [22]; [24]. (In contrast, recombinant C-terminal MSP1 proteins produced in the baculovirus expression system have consistently shown good protective efficacy in primates [25]; [26]; [27].)

Many parasitic protozoa with extra-cellular phases in their life cycles, such as *Plasmodium*, appear to express a majority of their surface proteins such that a C-terminal hydrophobic signalling sequence has been replaced with GPI moieties [28]. The primary function of GPI structures is to mediate a stable association of surface proteins to the plasma membrane, such that the functional ectoplasmic domain faces the external environment, in relative isolation with intracellular components. In particular, several *P. falciparum* merozoite surface proteins have GPI anchors, including MSP1, MSP2, MSP4 and MSP5 [28], the structure of which has been determined for MSP1 and MSP2 [1]. Recently *P. falciparum* GPIs have been implicated in the pathology of clinical malaria disease by inducing TNFα secretion, leading to fever and the up-regulation of capillary epithelial adhesion molecules that can bind infected erythrocytes causing capillary obstruction and associated pathologies [29]; [30]; [31]; [32, 33]; [34]. Indeed, individuals who live in malaria endemic areas can develop a specific anti-*P. falciparum* GPI antibody response, which is correlated with age and, in some cases, protection against disease [34]; [35]; [36]. In addition, mice immunized with synthetic *P. falciparum* GPI showed enhanced survival and reduced *P. berghei* induced symptoms of malaria. Moreover, antibody directed against this synthetic GPI could neutralize in vitro pro-inflammatory activity by *P. falciparum [*37].

In humans, immune responses to MSP1p19 as well as to *P. falciparum* GPIs have been associated with protection against clinical malaria [12]; [13]; [34]. The inventors were interested in developing means that can be encompassed in a vaccine candidate, which could permit to elicit an anti-toxic as well as an antiparasitic immunity, which could have an improved efficiency with respect to the immune response observed in various models, against soluble baculovirus MSP1p19.

Martinez et al [53] expressed a "recombinant ookinete surface antigen Pbs21 of *Plasmodium berghei* when prepared in a baculovirus SP21 insect cell expression system>>. The Pbs21 antigen expressed in the baculovirus system was disclosed by Martinez et al, to be produced in the cytoplasm of Sf21 cells, on their surface and in the extracellular medium. The expressed antigen was affinity purified starting from Sf21 cells resuspended in a solubilization buffer. Immunogenicity of the purified recombinant antigen was tested in mice and compared with immunogenicity of the native Pbs21 protein. The recombinant antigen was found to be less immunogenic than the native Pbs21. When discussing the obtained results. Martinez et al reported that recombinant Pbs21 (1-213) bearing the *Spodoptera* GPI anchor was less immunogenic but that the data obtained would suggest that the conformation and the presence of a GPI anchor is critical to the immunogenicity. It is furthermore disclosed that the majority of the response induced is to the folded polypeptide and not its post-translational additions.

However, although, several GPI-anchored proteins have already been expressed in an expression system, the capacity of expression systems to reproduce this anchor for the *Plasmodium* merozoite surface protein MSP1 remains controversial.

The invention relates to the objects defined in the claims, and more particularly to:

- purified polypeptides comprising or essentially consisting of a C-terminus MSP1 antigen from *Plasmodium* carrying a Glycosyl-phosphatidyl-inositol group (GPI),
- purified variants having at least 80% identity with such polypeptides,
- immunogenic compositions, wherein said composition comprises or essentially consists of at least one purified polypeptide or variant of the invention, and a pharmaceutically acceptable vehicule,
- vaccines against *Plasmodium* infection, wherein said vaccine comprises or essentially consists of at least one active principle, which is a purified polypeptide or variant of the invention,
- nucleic acid molecules, which encode the amino acid sequence of a purified polypeptide of the invention, or the amino acid sequence of a variant of the invention,
- nucleic acid molecules, which encode the amino acid sequence of a purified polypeptide of the invention, or the amino acid sequence of a variant of the invention, which is linked to at least one nucleic acid molecule, which encodes a signal peptide essentially consisting of, or comprising, the following sequence MKIIFFLCSFLFFIINTQC (SEQ ID NO: 3) and at least one nucleic acid molecule, which encodes at least one anchor peptide, which signals for GPI addition, said anchor peptide essentially consisting of or comprising the following sequence SSNFLGISFLLILMLILYSFI (SEQ ID NO: 4), nucleic acid molecules, which encode a purified polypeptide of the invention or a variant of the invention, which has a nucleotide sequence, which is optimised for codon usage appropriate in baculovirus expression vector, expression vectors for the expression of at least one purified polypeptide the invention, comprising at least of said nucleic acid molecules of the invention, expression system for the expression of at least one purified polypeptide of the invention, or of a variant of the invention, wherein said expression system comprises a baculovirus expression vector of the invention and insect cells, the recombinant baculovirus PfMSP1p19/His/GPI deposited at the C.N.C.M. on Nov. 10, 2005 under the accession number CNCM I-3515, the recombinant baculovirus PvMSP1p19/His/GPI deposited at the C.N.C.M. on Nov. 10, 2005 under the accession number CNCM I-3516, a polynucleotide, which essentially consists of the nucleic acid fragment of MSP1p19 contained in PfMSP1p19/His/GPI (CNCM I-3515) or in PvMSP1p19/His/GPI (CNCM I-3516).

BRIEF DESCRIPTION OF THE DRAWINGS:

FIG. 2. Structure of the baculovirus constructs expressed in insect cells. A) Pf19: construction used for the expression of the secreted form of the peptide MSP1-19. Pf19+A: construction used for the expression of the anchored form of the protein MSP1-19. Amino acids were numbered according to Chang et al., 1988 [39]. B) Amino acids sequence of SEQ ID NO 6 used to express pf19+A. The peptide signal is in bold, the sequence signal coding for the GPI attachment is in bold and underlined, glycosilation sites are underlined and the arrow indicates the beginning of the C-terminal part sequence of MSP1-19.

FIG. 3. Analysis of purified anchored pf19+A (+A) and secreted pf19 (−A) forms of MSP1-p19 recombinant proteins by A) coomassie blue staining in reduced conditions; B) immunobloting with a monoclonal antibody G17-12 in non-reduced conditions and C) immunobloting with a hyperimmune sera in non-reduced conditions. Molecular weights are given in kDa.

FIG. 4. Confocal micrographs of Pf 19+A (A) and pf19 (B) localization in HF (A.1,A.2) or Sf9 (A.3, A.4, B.1, B.2) non-fixed cells infected with recombinant baculovirus for 36 h. A.1 represents a three-dimentional composite of florescence from a whole cell, when A.2 and A.4 represents the central sections of the cells. Similar localization at the surface of the cells was observed in sf9 cells or HF cells for pf19+A when no fluorescent signal was recovered for pf19, either for Sf9 or HF cells.

FIG. 7: FIG. 7A) is the amino acid sequence of the peptide MSP1-19 of SEQ ID NO 1 originating from *Plasmodium falciparum*. Numbering of the amino acids is indicated under amino acid residues.

FIG. 7B) is the amino acid sequence of the peptide MSP1-19 of SEQ ID NO 2 originating from *Plasmodium falciparum* wherein an Histidine Tag has been inserted. Numbering of the amino acids is indicated under amino acid residues.

FIG. 8 displays the nucleic acid sequence (of SEQ ID NO 5) encoding the polypeptide of SEQ ID NO 6, which constitutes the insert of the Baculovirus PfMSP1p19/His/GPI deposited at the CNCM on Nov. 10, 2005 under the accession number I-3515. Said polypeptide originates from the *Plasmodium falciparum* MSP1p19 protein, that was modified by the insertion of an Histidine Tag, by the addition of a signal peptide of SE ID NO 3 at its N-terminal end, and by the addition of an anchor peptide of SEQ ID NO 4 at its C-terminal end. The first line indicates the nucleotide sequence, grouped by codons; the second line indicates the amino acid sequence corresponding to the above codons with the three-letter code. Numbering of the nucleic acids is at the right end of the first line, whereas numbering of the amino acids is indicated under amino acid residue (third line).

FIG. 9 displays the nucleic acid sequence (of SEQ ID NO 19) encoding the polypeptide of SEQ ID NO 20, which constitutes the insert of the Baculovirus PvMSP119/His/GPI deposited at the CNCM on Nov. 10, 2005 under the accession number I-3516. Said polypeptide originates from the *Plasmodium vivax* MSP1p19 protein The first line indicates the nucleotide sequence, grouped by codons; the second line indicates the amino acid sequence corresponding to the above codons with the three-letter code. Numbering of the nucleic acids is at the right end of the first line, whereas numbering of the amino acids is indicated under amino acid residue (third line).

FIG. 13A-B Course of the anti-MSP1-19 antibodies titer in mice sera. Mice sera immunized (↑) either with anchored form of MSP1-19 (pf19+A, broken curve) or secreted form of MSP1-19 (pf19, thin curve) diluted in 5 mM The pH8, 0.006% TRITON® X -100 and in the presence of MONTANIDE™ ISA 51(A) or PBS (B). Titers of each IgG isotype were evaluated 33 days and 70 days after the immunization, and at day 104 and 180, respectively 33 and 109 days after a second injection performed at day 71. No IgM was recovered at any bleed of the trial. Data are shown as mean of titer of each group (n=5) estimated as the highest dilution for a minimum absorbance of 0.5;

FIG. 15A illustrates the nucleotide and amino acid sequences of the synthetic gene (Bac 19) and the "native gene" (PF19) of *P. falciparum* described by Chang et al;

FIG. 15B illustrates the nucleotide and amino and sequences of the synthetic gene (Bac 19) and the "native gene" (PF19) of the Uganda Palo Alto isolate of *P. falciparum*;

FIG. 15C illustrates the PfMSP1$_{p19}$A recombinant protein sequence before cutting out the signal;

FIG. 15D illustrates the PfMSP1$_{p19}$A recombinant protein after cutting out the signal sequence;

DETAILED DESCRIPTION OF THE INVENTION

Figure 1:
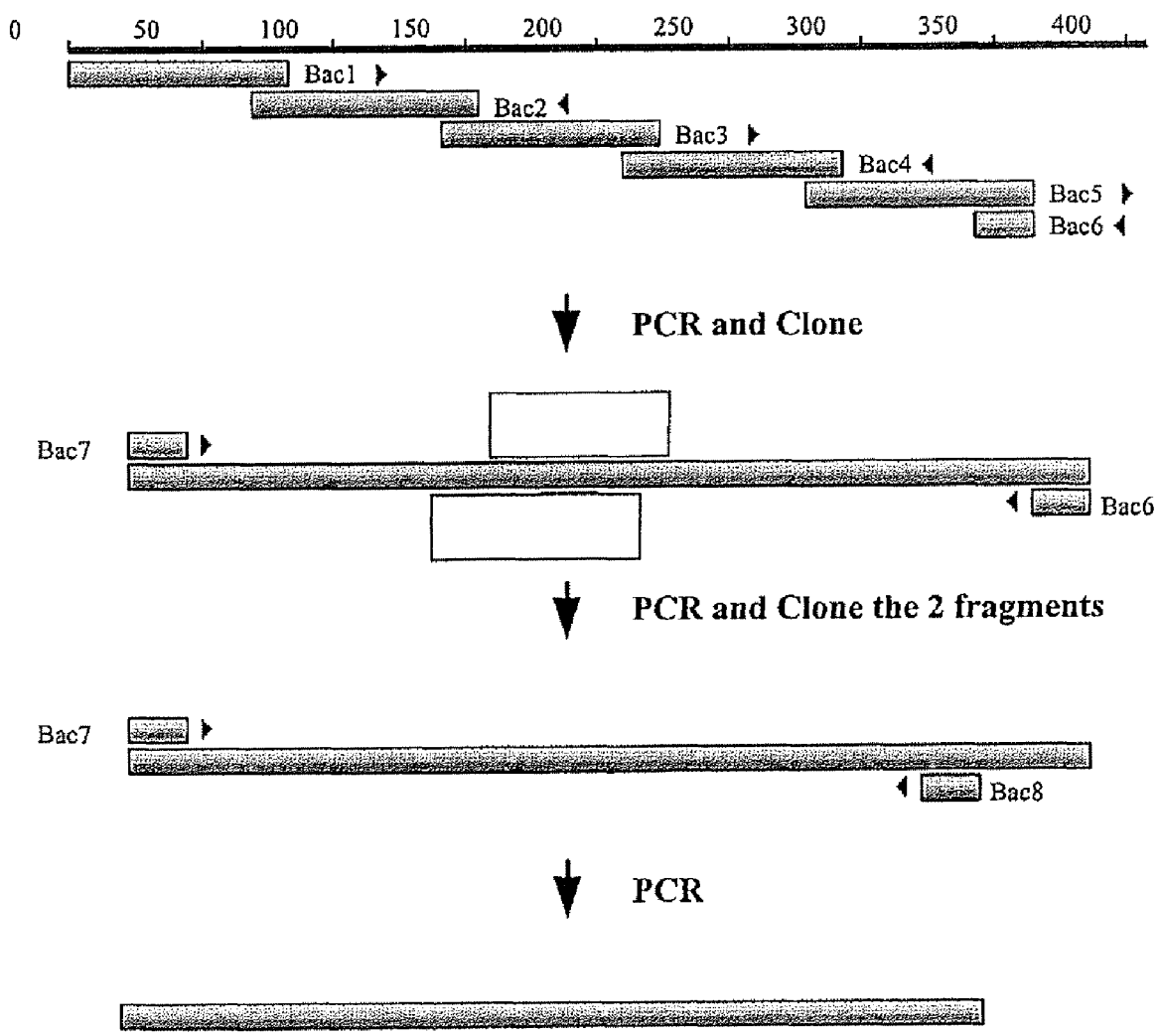
FIG. 1. Strategy used for recoding the C-terminal PfMSP1 sequence in a synthetic gene for the constructions used for the expression of the secreted and the anchored form of the protein MSP1-19.

The inventors have been able to express a polypeptide from the MSP1 antigen of *Plasmodium*, especially of *P. falciparum*, in eucaryotic cells, and have been able to purify it in conditions enabling the GPI anchor brought by the expression cells to be retained on the polypeptide, hence allowing its use in immunogenic assays.

The 19 kDa C-terminal fragment, the sequence of which is present in the active principle of the vaccine, can be limited to the sequence for the p19 itself, in the absence of any polypeptide sequence normally upstream of the p19 sequence in the corresponding MSP-1 protein. Clearly, though, the essential constituent polypeptide sequence of the active principle can also comprise a polypeptide sequence for the C-terminal side belonging to the 33 kDa (p33) N-termina) fragment still associated with the p19 in the corresponding p42, before natural cleavage of the latter, if the presence of this fragment does not modify the immunological properties of the active principle of the vaccine. As will be seen below, in particular in the description of the examples, the C-terminal sequences of the p33 in various strains of the same species of *Plasmodium* (see the C-terminal portion of the peptide sequences of "region III" in FIG. 18; SEQ ID NO: 34-37) also have a degree of homology or substantial conservation of the sequence, for example on the order of at least 80%, in different varieties of *Plasmodiums* which are infectious for man, such that they do not fundamentally modify the vaccinating properties of the active principle (the sequence of which corresponds to region IV in FIG. 4), in particular using the hypothesis which follows from this figure; that the presumed cleavage site between the p19 and region 111 of the p33 is located between the leucine and asparagine residues in a particularly well conserved region (LNVQTQ; SEQ ID NO: 38).

Normally the C-terminal polypeptide sequence of the p33, when it is present, comprises less than 50 amino acid residues, or even less than 35, preferably less than 10 amino acid residues.

The essential constituent polypeptide sequence of the active principle of the vaccine need not comprise all of the sequence coding for p19, naturally providing that the latter retains the ability to induce antibodies which protect against the parasite. In particular, the molecular weight of the "fragment portion" is 10 to 25 kDa, in particular 10 to 15 kDa. Preferably, this polypeptide fragment portion contains the two EGF (Epidermal Growth Factor) regions.

Clearly, the skilled person could distinguish between active fragments and those which would no longer be so, in particular experimentally by producing modified vectors containing inserts with different lengths originating from the p19, respectively isolated from the fragments obtained from the sequence coding for p19, by reaction with appropriate restriction enzymes, or by exonucleolytic enzymes which would be kept in contact with the fragment coding for p19 for differing periods; the capacity of the expression products from these inserts in the corresponding eukaryotic cells, in particular in insect cells, transformed by the corresponding modified vectors, to exert a protective effect can then be tested, in particular under the experimental conditions which are described below in the examples. In particular, the expression products of these inserts must be able to inhibit a parasitemia induced in vivo by the corresponding whole parasite.

Thus, the invention includes all vaccinating compositions in which the essential constituent polypeptide sequence of the active principle is constituted by a peptide which can induce a cellular and/or humoral type immunological response equivalent to that produced by p19 or a fragment as defined above, provided that the addition, deletion or substitution in the sequence of certain amino acids by others would not cause a large modification of the capacity of the modified peptide—hereinafter termed the "immunologically equivalent peptide"—to inhibit said parasitemia.

The p19 fragment can naturally also be associated at the N-terminal side or the C-terminal side or via a peptide bond to a further plasmoidal protein fragment having a vaccinating potential (such as Duffy binding protein from *P. vivax* (29) or EBA-175 from *P. falciparum* (30) and (31), one region of which is specifically rich in cysteine), provided that its capacity to inhibit parasitemia normally introduced in vivo by the corresponding parasite is not altered but is amplified.

Upstream of the N-terminal end of p19, the fragment coding for p19 or a portion thereof can also contain a peptide sequence which is different again, for example a C-terminal fragment of the signal peptide used, such as that for the MSP-1 protein. This sequence preferably comprises less than 50 amino acids, for example 10 to 40 amino acids.

These observations pertain in similar fashion to the p19 from other *Plasmodia*, in particular *P. falciparum*, the dominant species of the parasite, responsible for the most serious forms of malaria.

However, the techniques summarized above for producing a recombinant p19 from *P. vivax* or *P. cynomolgi* in a baculovirus system are difficult to transpose unchanged to producing a recombinant p19 of *P. falciparum* in a satisfactory yield, if only to obtain appreciable quantities which will allow immunoprotective tests to be carried out.

The invention also provides a process which overcomes this problem to a large extent. It also becomes possible to obtain much higher yields of *P. falciparum* p19—and other *Plasmodiums* where similar difficulties are encountered—using a synthetic nucleotide sequence substituting the natural nucleotide sequence coding for the p19 of *Plasmodium falciparum* in an expression vector of a baculovirus system, this synthetic nucleotide sequence coding for the same p19, but being characterized by a higher proportion of G and C nucleotides than in the natural nucleotide sequence. In other words, the invention follows from the discovery that expression of a nucleotide sequence coding for a p19 in a baculovirus system is apparently linked to an improved compatibility of successive codons in the nucleotide sequence to express with the "cellular machinery" of the host cells transformable by the baculovirus, in the manner of that observed for the natural nucleotide sequences normally contained in these baculovirus and expressed in the infected host cells; hence the poor expression, or even total absence of expression of a native *P. falciparum* nucleotide sequence; hence also a possible explanation of the more effective expression observed by Longacre et al. (14) for the p19 of *P. vivax* in a baculovirus system and, as the inventors have also shown, of the *P. cynomolgi* sequence from corresponding native p19 nucleotide sequences, because of their relatively much higher amounts of G and C nucleotides than those of the native nucleotide sequences coding for the p19 of *P. falciparum*.

The invention thus more generally provides a recombinant baculovirus type modified vector containing, under the control of a promoter contained in said vector and able to be recognized by cells transfectable by said vector, a first nucleotide sequence coding for a signal peptide exploitable by a baculovirus system, characterized by a second nucleotide sequence downstream of the first, also under the control of the promoter sequence and coding for the peptide sequence:

either of a 19 kilodalton (p19) C-terminal fragment of the surface protein 1 of the merozoite form (MSP-1 protein) of a *Plasmodium* type parasite other than *Plasmodium vivax* which is infectious for man, said C-terminal fragment remaining normally anchored to the parasite surface at the end of its penetration phase into human erythrocytes in the event of an infectious cycle;

or of a portion of that peptide fragment provided that the expression product from the second sequence in a baculovirus system is also capable of inducing an immune response which can inhibit in vivo parasitemia due to the corresponding parasite;

or of an immunologically equivalent peptide of said C-terminal peptide fragment (p19) or said peptide fragment portion by addition, deletion or substitution of amino acids not resulting in a large modification of the capacity of said immunologically equivalent peptide to induce a cellular and/or humoral type immunological response similar to that produced by said p19 peptide fragment or said portion of said fragment; and said nucleotide sequence having, if necessary, a G and C nucleotide content in the range 40% to 60%, preferably at least 50%, of the totality of the nucleotides from which it is constituted. This sequence can be obtained by constructing a synthetic gene in which the natural codons have been changed for codons which are rich in G/C without modifying their translation (maintaining the peptide sequence).

The nucleotide sequence, provided by a synthetic DNA, may have at least 10% of modified codons with respect to the natural gene sequence or cDNA while retaining the characteristics of the natural translated sequence, i.e., maintaining the amino acid sequence.

It is not excluded that this G and C nucleotide content could be further increased provided that the modifications resulting therefrom as to the amino acid sequence of the recombinant peptide—or immunologically equivalent peptide—produced do not result in a loss of immunological properties, or protective properties, of the recombinant proteins formed, in particular in the tests which will be described below.

These observations naturally apply to other *Plasmodium* which are infectious for man, in particular those where the native nucleotide sequences coding for corresponding p19s would have T and A nucleotide contents which are poorly compatible with effective expression in a baculovirus system.

The sequence coding for the signal used can be that normally associated with the native sequence of the *Plasmodium* concerned. But it can also originate from another *Plasmodium*, for example *P. vivax* or *P. cynomolgi* or another organism if it can be recognized as a signal in a baculovirus system.

The sequence coding for p19 or a fragment thereof in the vector under consideration is, in one case, deprived of the anchoring sequence of the native protein to the parasite from which it originates, in which case the expressed protein is generally excreted into the culture medium (soluble form). It is also remarkable in this respect that under the conditions of the invention, the soluble and anchored forms of the recombinant proteins produced, in particular when they are from *P. falciparum* or *P. cynomolgi* or *P. vivax*, tend to form oligomers, this property possibly being at the origin of the increased immunogenicity of the recombinant proteins formed.

The invention also concerns vectors in which the coding sequence contains the terminal 3' end sequence coding for the hydrophobic C'-terminal end sequence of the p19 which is normally implicated in the induction of anchoring the native protein to the cell membrane of the host in which it is expressed. This 3'-terminal end region can also be heterologous as regards the sequence coding for the soluble p19 portion, for example corresponding to the 3'-terminal sequence from *P. vivax* or from another organism when it codes for a sequence which anchors the whole of the recombinant protein produced to the cell membrane of the host of the baculovirus system used. An example of such anchoring sequences is the GPI of the CD59 antigen which can be expressed in the cells of 10 *Spodoptera frugiperda* (32) type insects or the GPI of a CD14 human protein (33).

The invention also, naturally, concerns recombinant proteins, these proteins comprising conformational epitopes recognized by human serums formed against the corresponding *Plasmodium*.

In general, the invention also concerns any recombinant protein of the type indicated above, provided that it comprises conformational epitopes such as those produced in the baculovirus system, in particular those which are unstable in a reducing medium.

The invention also, naturally, concerns said recombinant proteins, whether they are in their soluble form or in the form provided with an anchoring region, in particular to cellular hosts used in the baculovirus system.

The invention also encompasses oligomers spontaneously produced in the baculovirus systems used or produced a posteriori, using conventional protein oligomerisation techniques. The most commonly used technique involves glutaraldehyde. However, any conventional system for bridging between the respective amine and carboxyl functions in proteins can be used. As an example, any of the techniques described in European patent application EP-A-0 602 079 can be used.

The term "oligomer" means a molecule containing 2 to 50 monomer units, each of the monomer units containing p19 or a fragment thereof, as defined above, capable of forming an aggregate. The invention also encompasses any conjugation product between a p19 or a p19 fragment as defined above, and a carrier molecule—for example a polylysine-alanine— for use in producing vaccines, via bonds which are covalent or otherwise. The vaccinating compositions using them also form part of the invention.

The invention still further concerns vaccine compositions using these oligomeric or conjugated recombinant proteins, including proteins from *Plasmodium vivax*, these observations also extending to oligomers of these recombinant proteins.

The invention also encompasses compositions in which the recombinant proteins defined above are associated with an adjuvant, for example an alum. Recombinant proteins containing the C-terminal and region allowing them to anchor to the membrane of the cells in which they are produced are advantageously used in combination with lipids which can form liposomes appropriate to the production of vaccines. Without being limiting, lipids described, for example, in the publication entitled "Les liposomes aspects technologique, biologique et pharmacologique" [Liposomes: technological, biological and pharmacological aspects] by J. Delattre et al., INSERM, 1993, can be used.

The presence of the anchoring region in the recombinant protein, whether it is a homologous or heterologous anchoring region as regards the vaccinating portion proper, encourages the production of cytophilic antibodies, in particular $IgG_{2a}$ and $IgG_{2b}$ type in the mouse which could have a particularly high protective activity, so that associating the active principles of the vaccines so constituted with adjuvants other than the lipids used to constitute the liposome forms could be dispensed with. This amounts to a major advantage, since liposomes can be lyophilized under conditions which enable them to be stored and transported, without the need for chains of cold storage means.

Other characteristics of the invention will become clear from the following description of examples of recombinant proteins of the invention and the conditions under which they can be produced. These examples are not intended to limit the scope of the invention.

Description of the Construction of $PfMSP1_{p19}S$ (Soluble) (Soluble p19 from *P. falciparum*)

The recombinant construction $PfMSP1_{p19}S$ contains the DNA corresponding to 8 base pairs of the leader sequence and the first 32 amino acids of the MSP-1 of *Plasmodium vivax* from $Met_1$ to $Asp_{32}$ (Belem isolate; Del Portillo et al., 1991, P.N.A.S., 88, 4030) followed by GluPhe due to the EcoR1 site connecting the two fragments. This is followed by the synthetic gene described in FIG. 1, coding the *Plasmodium falciparum* $MSP1_{p19}$ from $Asn_{1613}$ to $Ser_{1705}$ (Uganda-Palo Alto isolate; Chang et al., 1988, Exp. Parasitol., 67, 1). The construction is terminated by two TAA stop codons. This construction gave rise to a recombinant protein which was secreted in the culture supernatant from infected cells.

In the same manner and for comparison, a recombinant construction was produced under conditions which were similar to those used to produce the p19 above, but working with a coding sequence consisting of a direct copy of the corresponding DNA of the *P. falciparum* strain (FUP) described by Chang et al., Exp. Parasit. 67,1; 1989. The natural gene copy (from asparagine 1613 to serine 1705) was formed from the native gene by PCR.

FIG. 15A shows the sequences of both the synthetic gene (Bac19; SEQ ID NO: 24) and the "native gene" (PF19; SEQ ID NO: 26).

It can be seen that 57 codons of the 93 codons of the native sequence coding for the p19 from *P. falciparum* were modified (the third nucleotide in 55 of them and the first and third nucleotides in the other 2 codons). New codons were added to the 5' end to introduce the peptide signal under the conditions indicated above and to introduce an EcoRI site for cloning, and similarly two stop codons were added which were not present in the *P. falciparum* p19 to obtain expression termination signals. The individual letters placed above successive codons correspond to the respective successive amino acids.

Asterisks (*) show the stop codons. Vertical lines indicate the nucleotides which are the same in the two sequences Description of the PfMSP1$_{p19}$A Construction (Anchored GPI) (Anchored p19 of *P. falciparum*)

The PfMSP1$_{p19}$A construction had the characteristics of that above except that the synthetic sequence (FIG. 15B) codes for the MSP1$_{p19}$ of *Plasmodium falciparum* (Uganda-Palo Alto isolate) from Asn$_{1613}$ to ILe$_{1726}$ followed by two TAA stop codons. This construction gave rise to a recombinant protein which was anchored in the plasma membrane of infected cells by a glycosyl phosphatidyl inositol (GPI) type structure.

FIG. 15C represents the PfMSP1$_{p19}$S recombinant protein sequence before cutting out the signal sequence (SEQ ID NO: 30).

FIG. 15D represents the PfMSP1$_{p19}$S recombinant protein sequence after cutting out the signal sequence (SEQ ID NO: 32).

The amino acids underlined in FIGS. 15C and 15D originate from the EcoR1 site used to join the nucleotide sequences derived from the N-terminal portion of the MSP-1 of *P. vivax* (with signal sequence) and the MSP-1 $_{p19}$ of *P. falciparum*.

Figure 16A:
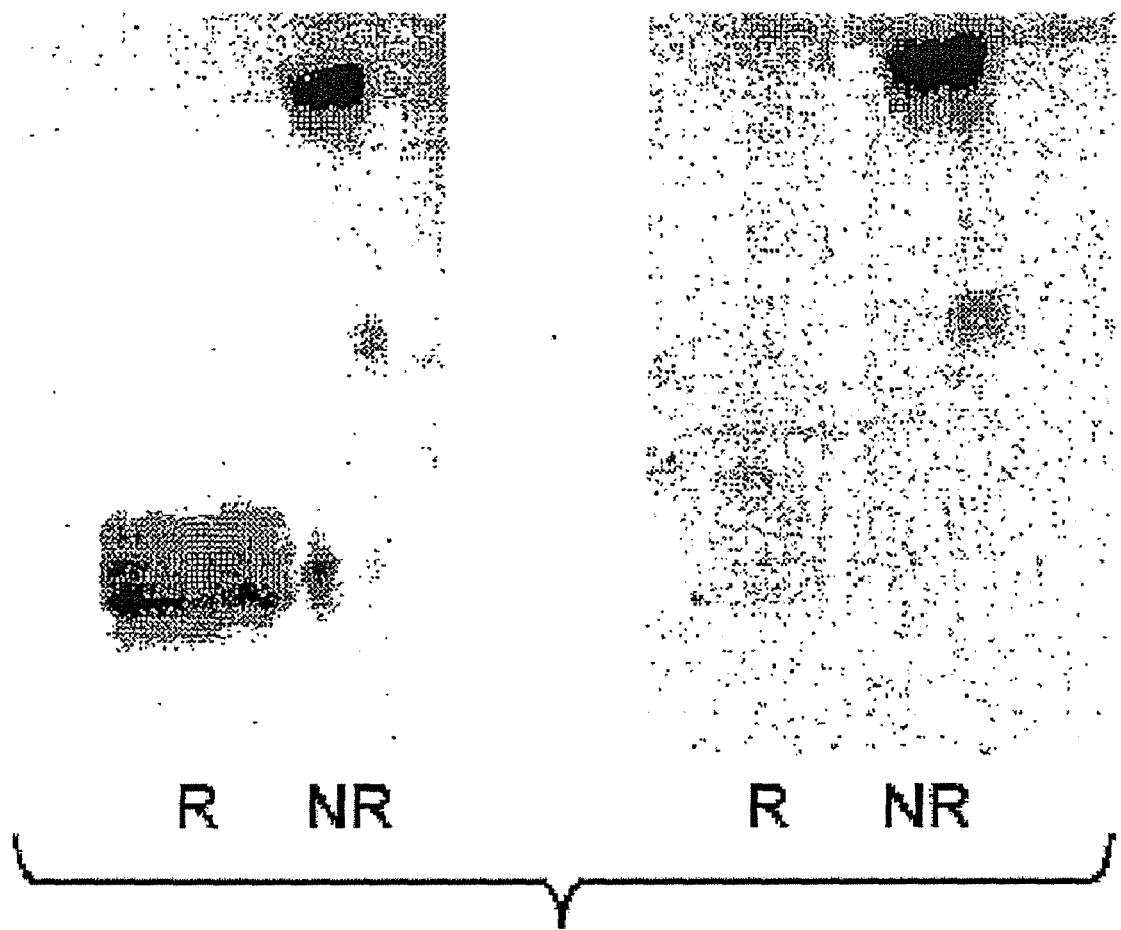
FIG. 16A is an immunoblot using SDS-PAGE of the soluble recombinant PfMSP1$_{p19}$ antigen purified by immunoaffinity of the presence (reduced) or absence (non-reduced) of β-mercaptoethanol.

FIG. 16—The soluble recombinant PfMSP1$_{p19}$ antigen purified by immunoaffinity was analyzed by immunoblot using SDS-PAGE in the presence (reduced) or absence (non reduced) of β-mercaptoethanol. Samples were charged onto gel after heating to 95° C. in the presence of 2% SDS. Under these conditions only covalent type bonds (disulphide bridges) can resist disaggregation. The left hand blot was revealed with a monoclonal antibody which reacted with a linear epitope of natural p19. The right hand blot was revealed with a mixture of 13 human antisera originating from subjects with acquired immunity to malaria due to *Plasmodium falciparum*. These results show that the recombinant baculovirus molecule can reproduce conformational epitopes in the form of a polymer the majority of which are recognized by human antiserum.

Figure 16B:
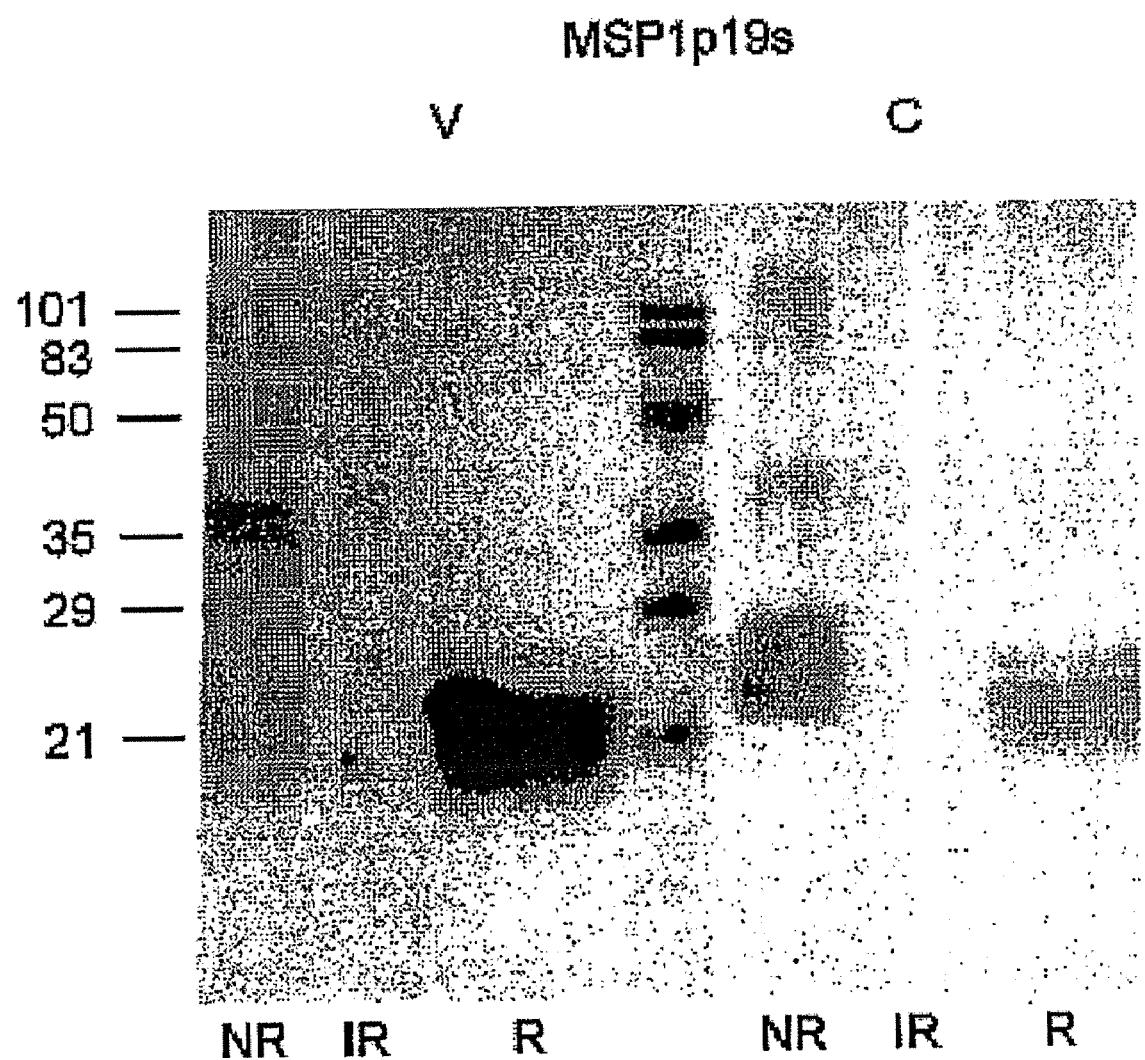
FIG. 16B is an immunoblot with human antiserum of recombinant purified MSP-1 P19 from *P. vivax* and *P. cynomoigi* under non-reduced (NR), reduced only in the charging medium (R) and irreversibly reduced (IR) conditions.

FIG. 16B: Immunoblot Analysis with Human Antiserum of Recombinant Purified MSP-1 p19 from *P. vivax* and *P. cynomolgi* Under Non Reduced (NR), Reduced Only in the Charging Medium (R) and Irreversibly Reduced (IR) Conditions:

This work was based on the idea that the baculovirus expression system correctly reproduced the conformational epitopes present in vivo on the C-terminal portion of MSP-1 in large amounts. The best means of measuring this property (which may be the only possible means in the absence of native purified proteins corresponding to p19) was to study the reactivity of the recombinant proteins with the antiserum of individuals exposed to malaria, this reflecting the native proteins as "seen" by the human immune system.

Thus soluble recombinant PvMSP-1 p19 and PcMSP-1 p19 antigens purified by immunoaffinity were analyzed by immunoblot using SDS-PAGE (15%) in the presence (reduced) or absence (non reduced) of DTT. Samples were loaded onto the gel after heating to 95° C. in the presence of 2% SDS. The irreversible reduction was carried out as follows: the protein was resuspended in 0.2 M Tris-HCl, pH 8.4, 100 mM DTT, 1.0% SDS and heated for 30 minutes at 70° C. After diluting with water, acrylamide was added to a final concentration of 2 M and the mixture was incubated under nitrogen in the dark for 1 hour at 37° C. The immunoblot was revealed with a mixture of 25 human antisera originating from subjects with an acquired immunity to malaria due to Plasmodium vivax. V and C respectively designate proteins derived from the MSP-1 of *P. vivax* and *P. cynomolgi*. It should be noted that irreversibly reduced recombinant proteins exhibited no reactivity with human antiserum while non irreversibly reduced proteins or non reduced proteins exhibited good reactivity. (The non reduced Pv MSP-1 p19 was a little weak since in its glycosylated state it does not bind well to nitro-cellulose paper). These results show that recognition of baculovirus MSP-1 p19 molecules by human antiserum is largely if not completely dependent on conformational epitopes sensitive to reduction which are reproduced in this system.

Figure 17A:
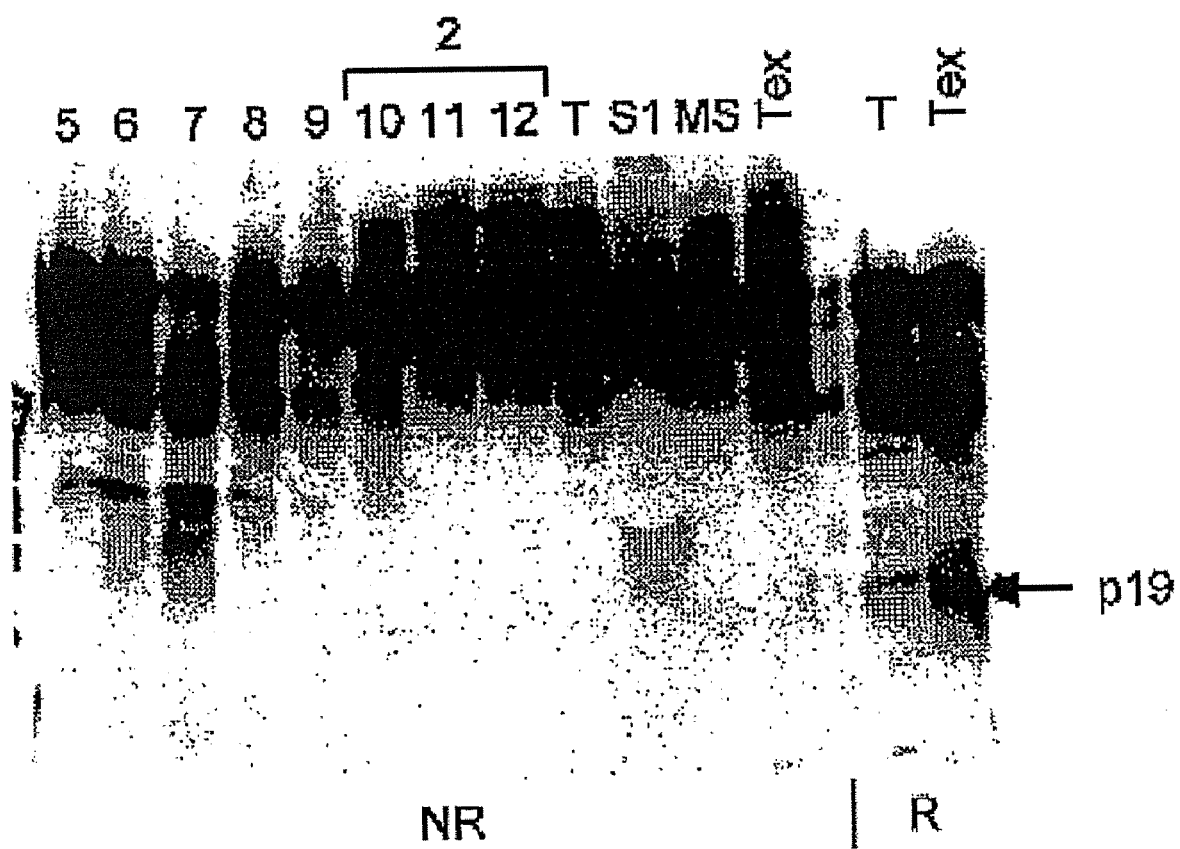
FIG. 17A is an immunoblot of the soluble PvMSP1$_{p42}$ recombinant antigen in the presence of protein fractions derived from merzoites of *P. falciparum* and separately isoelectric focusing in the presence (reduced) or absence (non reduced) of β-mercaptoethanol.

FIG. 17—The soluble PvMSP1$_{P42}$ recombinant antigen (Longacre et al., 1994, op. Cit.) was incubated for 5 hours at 37° C. in the presence of protein fractions derived from merozoites of *P. falciparum* and separated by isolectrofocussing. The samples were then analyzed by immunoblot in the presence (reduced) or absence (non reduced) of β-mercaptoethanol. isolectrofocussing fractions 5 to 12, and two total merozoite extracts made in the presence (Tex) or absence (T) of detergent, were analyzed. The immunoblot was revealed with monoclonal antibodies specific for MSP1$_{p42}$ and $_{p19}$ of *P. vivax*. The results suggest that there is a proteolytic activity in the *P. falciparum* merozoites which can be extracted with detergent. Digestion of p42 in certain fractions appear to cause polymerization of the digestion products (p19); this polymerization is probably linked to the formation of disulphide bridges since in the presence of β-mercaptoethanol, the high molecular weight forms disappear in favor of a molecule of about 19 kDa (Tex-R). The p19 polymerization observed in these experiments could thus be an intrinsic property of this molecule in vivo.

Figure 17B:
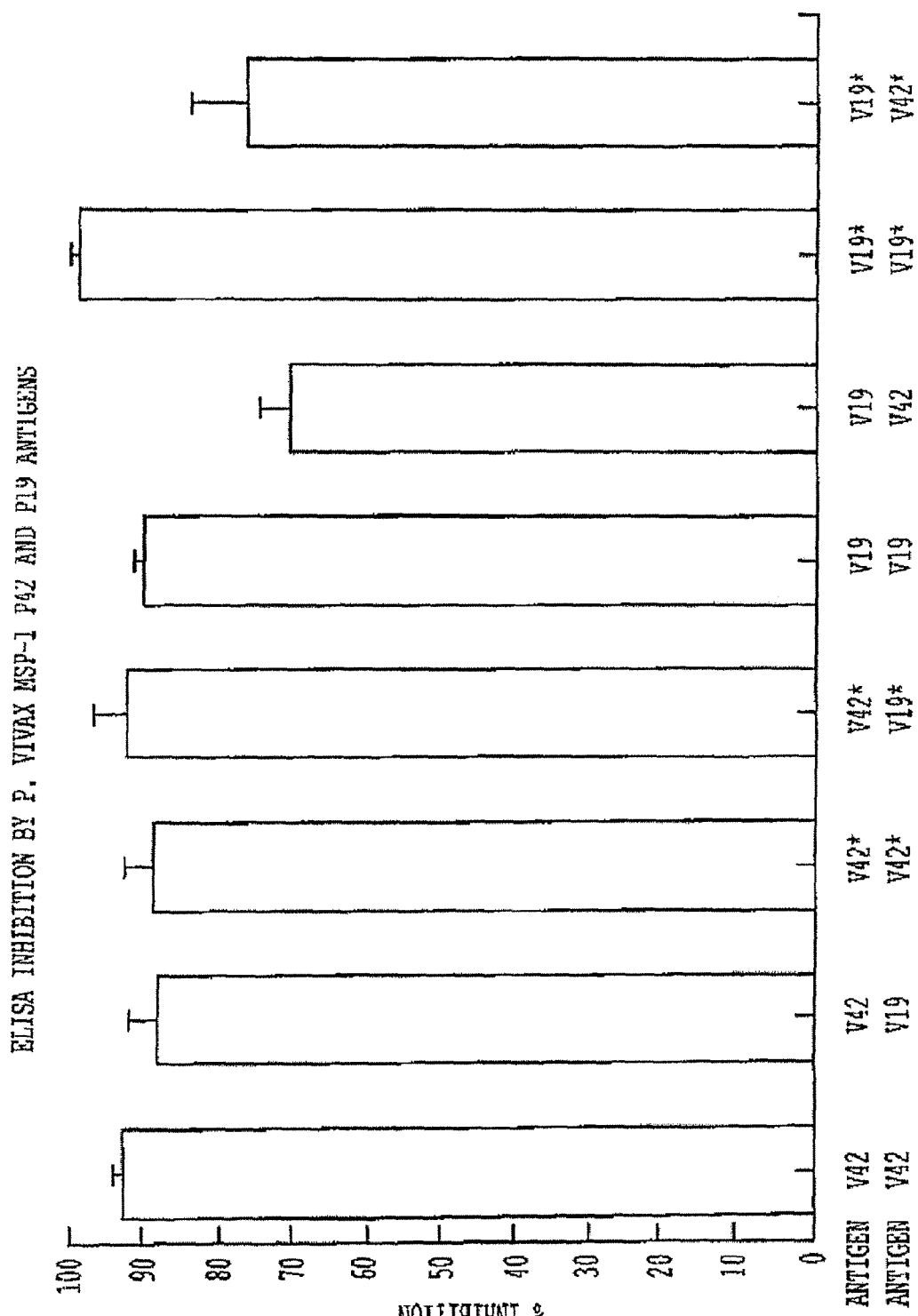
FIG. 17B is a graph illustrating the results of an ELISA inhibition technique of *P. vivax* MPS-1 P42 and P12 antigens by the antiserum of individuals with an acquired immunity to *P. vivax*.

FIG. 17B: The Differential Contribution of p42 and p19 Antigens to the *P. vivax* anti-MSP-1 Human Response.

Recognition of *P. vivax* MSP-1 p42 and p19 antigens by the antiserum of individuals with an acquired immunity to *P. vivax* was compared using the ELISA inhibition technique as follows: a mixture of 25 human antisera originating from subjects with an acquired immunity to malaria due to *P. vivax* was diluted to 1:5000 and incubated for 4 hours at ambient temperature either alone, or in the presence of a 1 mM purified *P. vivax* recombinant p42 or p19. This mixture was transferred to a microtiter well which had been coated for 18 hours at 4° C. with 500 ng.ml$^{-1}$ of purified absorbed recombinant p42 or p19, and incubated for 30 minutes at ambient temperature. After washing with PBS containing 0.1% of Tween 20, a goat anti-mouse IgG conjugated with peroxidase was added and the mixture was incubated for 1 hour at 37° C. The enzymatic activity was revealed by reading the optical density at 492 nm. The percentage inhibition was calculated based on values of 100% of antiserum activity with the coated antiserum on the microtiter plate in the absence of a competing antigen. Statistical data were calculated using a Statview program. Each bar represents the average percentage inhibition of a pair of competing/absorbed antigens based on 4 to 12 determinations; the vertical lines correspond to a 95% confidence interval. Asterisks (*) designate the antigens produced in the presence of tunicamycin, thus with no N-glycosylation. The important parameters of these measurements were the dilution of the antiserum by 1:5000 which is in the region which is sensitive to ELISA curves and the competing antigen concentrations of 1 mM which includes competition by low affinity epitopes. Thus these data reflect the maximum resemblance between the two compared antigens. The results show that the majority, if not all of the p42 epitopes recognized by the human antiserum are present on the p19 since in the presence of the latter, the reactivity of the human antiserum against p42 is inhibited as much as by the p42 antigen itself. In contrast, however, about 20% of the p19 epitopes recognized by human antiserum were not or were not accessible on the p42, since the reactivity of the human antiserum against the p19 was much less inhibited by p42 than by p19 itself. Such specific epitopes of p19 could be constituted or revealed only after cleaving the p42 into p19 and p33. These results were not affected by glycosylation showing that the effect is really due to a difference between the peptide components of p19 and p42 and not to a difference in glycosylation. These results underline the fact that p19 has a distinct immunobgical identity compared to p42.

Description of the PcMSP1$_{p19}$S (Soluble) Construction (Soluble p19 of *P. cynomolgi*)

The DNA used for the above construction was obtained from a clone of the *Plasmodium cynomolgi ceylonesis* strain (22-23). This strain had been maintained by successive passages through its natural host (*Macaca sinica*) and cyclic transmissions via mosquitoes (27).

Blood parasites in the mature schizont stage were obtained from infected monkeys when the parasitemia had attained a level of 5%. They were then purified using the methods described in (25). The DNA was then extracted as described in (26).

Figure 18B:
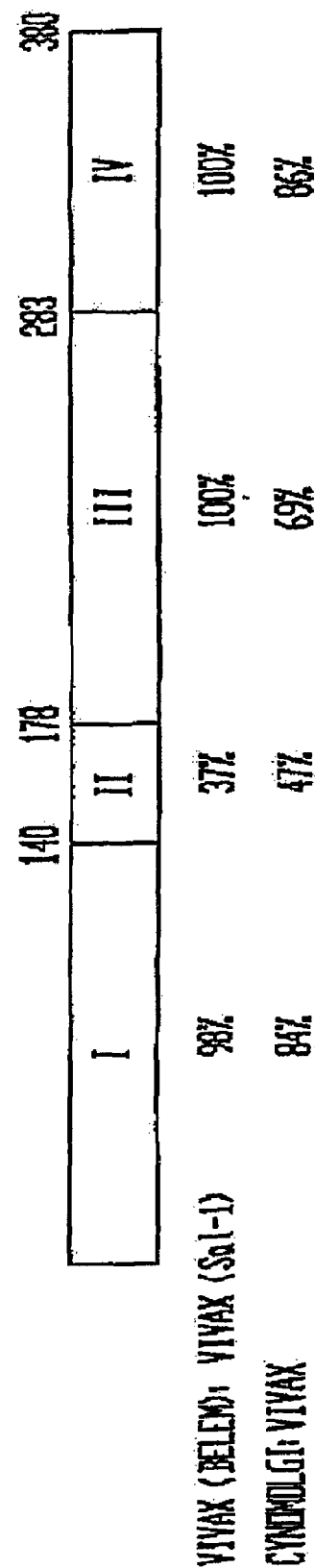
FIG. 18A.1 and 18A.2 are nucleotide sequences. The underlines oligonucleotides originate from *P. vivax* and are used as primers in a PCR reaction. The lower portion of FIG. 18 (18B) illustrates the percent identity between two isolates of *P. vivax* and *P. cynomoigi*.

A 1200 base pair fragment was produced using a PCR reaction using the oligonucleotides underlined in FIG. 18 originating from *P. vivax*. The 5' oligonucleotide comprised an EcoRI restriction site and the 3' oligonucleotide comprised two synthetic TAA stop codons followed by a BgIII restriction site. This fragment was introduced by ligation and via these EcoRI and BgIII sites into the pVLSV$_{200}$ plasmid already containing the signal sequence for the MSP-1 protein of *P. vivax* (19). The new plasmid (pVLSV$_{200}$C$_{42}$) was used to analyze the DNA sequences.

The *P cynomolgi* and the corresponding *P. vivax* sequences were aligned (SEQ ID NO: 34-37). The black arrows designate the presumed primary and secondary cleavage sites. They were determined by analogy with known sites in *P. falciparum* (27, 28). The vertical lines and horizontal arrows localize the limits of the four regions which were studied. Region 4 corresponded to the sequence coding for the *P. cynomolgi* p19. Glycosylation sites are boxed and the preserved cysteines are underlined. The lower portion of FIG. 18 shows the percentage identity between the two isolates of *P. vivax* and *P. cynomolgi*.

The recombinant construction PcMSP1$_{p19}$S contains the DNA corresponding to 8 base pairs of the leader sequence and the first 32 amino acids of the MSP-1 of *Plasmodium vivax* from Met$_1$ to Asp$_{32}$ (Belem isolate; Del Portillo et al., 1991, P.N.A.S., 88, 4030) followed by GluPhe, due to the EcoR1 site, connecting the two fragments. This is followed by the sequence coding for the *Plasmodium cynomolgi* MSP1$_{p19}$ from Lys$_{276}$ to Ser$_{380}$ (Ceylon strain). The construction was terminated by two TAA stop codons. This construction gave rise to a recombinant protein which was secreted in the culture supernatant of infected cells.

Purification of Recombinant PfMSP1p19 Protein by Immunoaffinity Chromatography with a Monoclonal Antibody Specifically Recognizing the p19 of *Plasmodium falciparum*

The chromatographic resin was prepared by binding 70 mg of a monoclonal antibody (obtained from a G17.12 hybridoma deposited at the CNCM [National Collection of Microorganism Cultures] (Paris, France) on the 14$^{th}$ February 1997, registration number 1 -1846; this G17.12 hybridoma was constructed from X63 Ag8 653 myeloma producing IgG 2a/k recognizing the *P. falciparum* p19) to 3 g of activated CNBr-SEPHAROSE® 4B (Pharmacia) using standard methods detailed in the procedure employed by Pharmacia. The culture supernatants containing the soluble PfMSP1p19 were batch incubated with the chromatographic resin for 16 hours at 4° C. The column was washed once with 20 volumes of 0.05% NP40, 0.5 M of NaCl, PBS; once with 5 volumes of PBS and once with 2 volumes of 10 mM of sodium phosphate, pH 6.8. Elution was carried out with 30 ml of 0.2 M glycine, pH 2.2. The eluate was neutralized with 1 M sodium phosphate, pH 7.7 then concentrated by ultrafiltration and dialyzed against PBS. To purify the anchored PfMSP1p19, all of the washing and elution solutions contained a supplemental 0.1% of 3-(dimethyl-dodecylammonio)-propane sulphonate (Fluka).

FIG. 20: Vaccination Test with a Recombinant *Plasmodium falciparum* p19 in the Squirrel Monkey Twenty *Saimiri sciureus guyanensis* (squirrel monkeys) of about 3 years old raised in captivity were used as follows: (1) 4 animals injected with 50 µg of soluble Pf MSP-1 p19 in the presence of Freunds adjuvant as follows: 1st injection: 1:1 FCA/FIA; 2nd injection: 1:4 FCA/FIA; 3rd injection: FIA. These adjuvant compositions were then mixed with 1:1 antigen in PBS; (2) 2 control animals received Freunds adjuvant as described for (1) with only PBS; (3) 4 animals injected with 50 µg of soluble Pf MSP-1 p19 in the presence of 10 mg of alum (Alu-Gel-S, Serva); (4) 2 control animals received 10 mg of alum with only PBS; (5) 4 animals injected with about 50-100 mg of GPI anchored Pf MSP-1 p19 reconstituted into liposomes as follows: 300 mmoles of cholesterol and 300 mmoles of phosphatidyl choline were vacuum dried and resuspended in 330 mM of N-octylglucoside in PBS with 1.4 mg of Pf MSP-1 p19, GPI. This solution had been dialyzed against PBS with adsorbent Bio-Beads SM-2 (Bio-Rad) and the liposomes formed were concentrated by centrifuging and resuspended in PBS The 1st injection was made with fresh liposomes kept at 4° C. and the 2nd and 3rd injections were made with liposomes which had been frozen for preservation; (6) 2 animals injected with control liposomes made in the same way, in the absence of the p19. GPI antigen as described for (5); (7) 2 animals injected with physiological water. Three intramuscular injections were made at 4 week intervals. The challenge infection was made by injecting 1×106 red blood cells infected with *Plasmodium falciparum*. Protection was evaluated by determining parasitemia daily in all animals by examining the Giemsa smears. Parasitemia were expressed as the percentage of parasitised red blood cells. The results of this vaccination test are shown in FIGS. 20, A-G.

The groups immunized with p19 in Freunds adjuvant or liposome demonstrated similar parasitemia to the control groups after a challenge infection (one animal (number 29) vaccinated with p19 in Freunds adjuvant died several days after challenge infection for reasons independent of vaccination (cardiac arrest). Irregularities in administration of the antigen in these 2 groups (poor Freunds emulsion, congealed liposomes) did not allow the significance of these results to be completely evaluated. In the alum group, 2 animals showed total parasitemia for the duration of the infection about 8 times less than the controls, 1 animal about 3 times less and 1 animal was similar to the controls. This experiment was a little difficult to interpret due to the variability in the controls, probably due to the strain of parasite used for the challenge infection which would not have been quite adapted to the non splenectomized Saimiri model developed only recently in Cayenne. However, the real effect with alum, although imperfect, is encouraging in that our antigens seem to be the only recombinant *P. falciparum* MSP-1 versions which currently have shown a certain effectiveness in combination with alum.

Figure 19A:
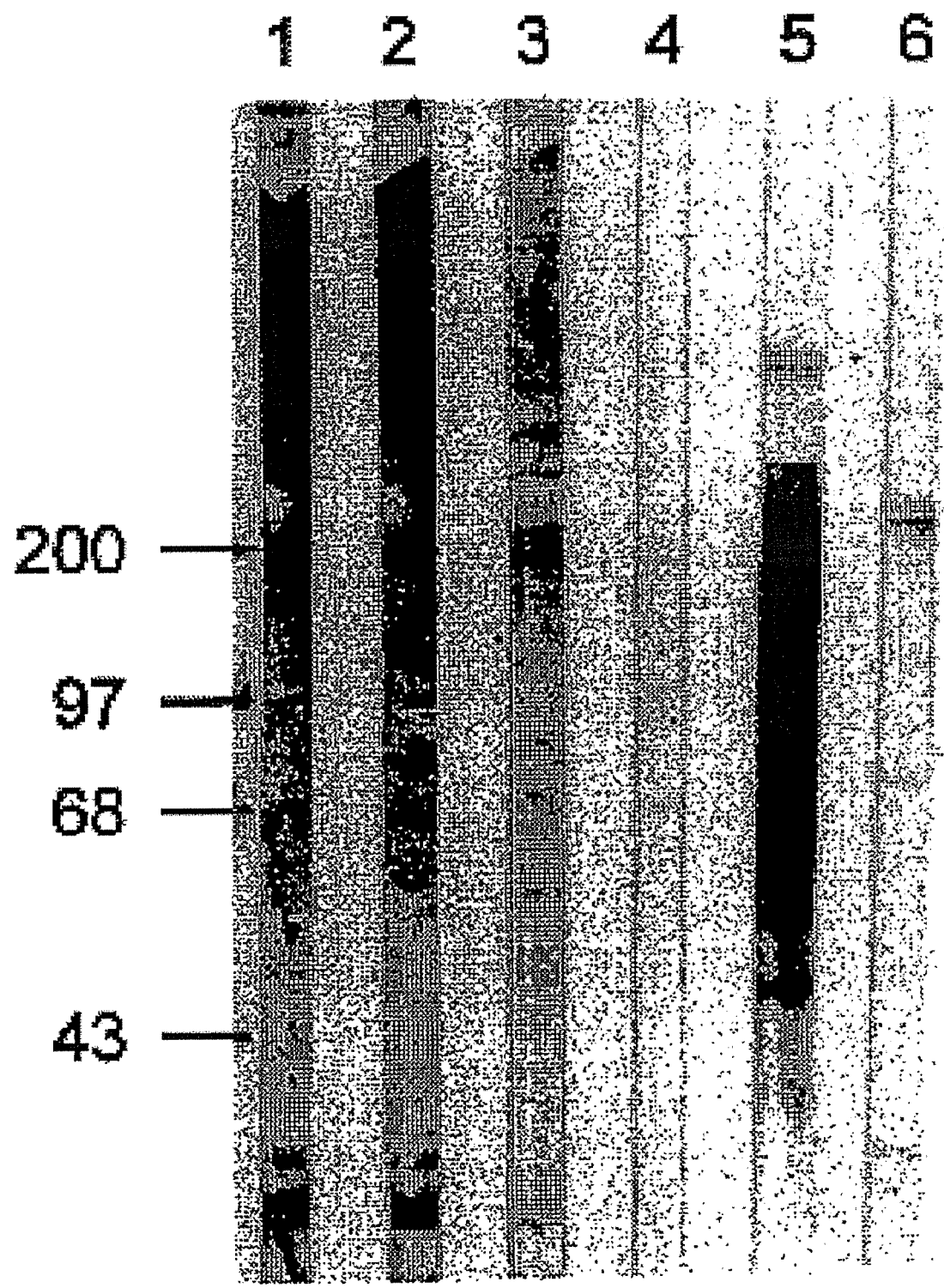
FIG. 19A is an immunoblot illustrating the in vivo response of monkeys to injections of p19 with Freunds adjuvant (1), with alum (2) and in the form of liposomes (3)

FIG. 19: Specific Reactivity with *P. falciparum* MSP1 p19 Monkey Anti-Sera with High Molecular Weight Aggregates (Same Antisera as for FIG. 20)

Monkeys bred in captivity were injected intramuscularly with 1 ml of inoculum twice at 4 week intervals as follows: (1) 4 animals injected with 50 μg of soluble PfMSP1p19 in the presence of Freunds adjuvant as follows: 1st injection: 1:1 FCA/FIA; 2nd injection: 1:4 FCA/FIA; and mixed then 1:1 with the antigen in PBS; (2) 4 animals injected with 50 μg of soluble PfMSPp19 in the presence of 10 mg of alum; (3) 4 animals injected with about 50 μg of GPI anchored PfMSP1p19 reconstituted into liposomes composed of 1:1 molar cholesterol and phosphatidyl choline. The animals were bled 17 days after the second injection.

Red cells from a squirrel monkey with 30% parasitemia due to *P. falciparum* (with the mature forms in the majority) were washed with PBS and the residue was diluted 8 times in the presence of 2% SDS and 2% dithiothreitol and heated to 95° before being charged onto a polyacrylamide gel of 7.5% (separation gel) and 4% (stacking gel). After transfer to nitrocellulose, immunoblot analysis was carried out with antisera as follows: (1) pool of antisera of 4 monkeys vaccinated with soluble PfMSP1p19 in Freunds adjuvant, 1:20; dilution; (2) pool of antisera of 4 monkeys vaccinated with soluble PfMSP1p19 in alum adjuvant, 1:20 dilution; (3) pool of antisera of 4 monkeys vaccinated with anchored PfMSP1p19 in liposomes, 1:20 dilution; (4) monoclonal antibody, which reacts with a linear epitope of PfMSP1p19, 50 μg/ml; (5) SHI90 antisera pool originating from about twenty monkeys repeatedly infected with *P. falciparum* and which had become resistant to any subsequent infection with *P. falciparum*, 1:500 dilution; (6) antiserum pool of unaffected monkeys (never exposed to *P. falciparum*), twentieth dilution.

The results in FIG. 19 show that the 3 antisera pools of monkeys vaccinated with PfMSP1p19 reacted strongly and specifically with very high molecular weight complexes (diffuse in the stacking gel) and present in parasite extracts containing more mature forms. These results support the hypothesis that a specific aggregate of PfMSP1p19 is present in vivo comprising epitopes which are reproduced in recombinant PfMSP1p19 molecules synthesized in the baculovirus system, in particular oligomeric forms thereof.

FIG. 19 also illustrated these results. It shows immunoblots produced on gel. The first three gel tracks illustrate the in vivo response of monkeys to injections of p19 [(1) with Freund adjuvant, (2) with alum, (3) in the form of a liposome] and in particular the existence of high molecular weight complexes supporting the hypothesis of in vivo aggregation of p19 in the form of an oligomer, specific to the maturation stage (when p42 is out into p19 and p33).

This vaccination test also comprises a third injection identical to the previous injections. The injection with Freund adjuvant contained only FIA.

There were two animal controls for each group, namely: 2 control animals injected with PBS and Freunds adjuvant; 2 control animals injected with PBS and alum; 2 control animals injected with liposomes without protein; and two control animals injected with PBS without adjuvant Protection was evaluated as described above.

Figure 19B:
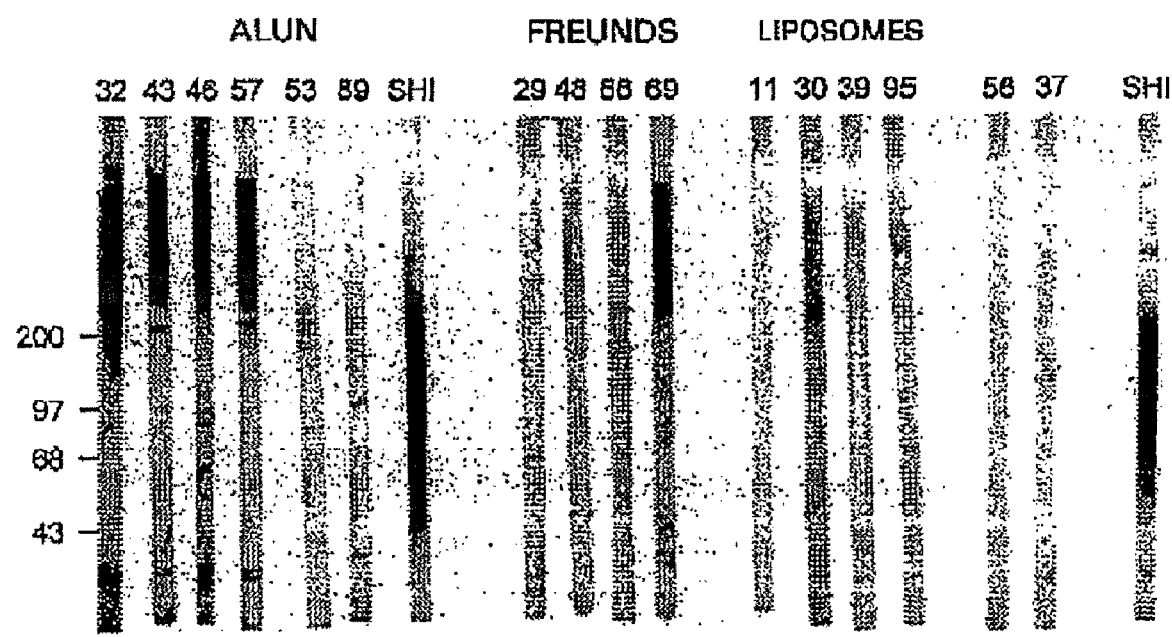
FIG. 19B is an immunoblot illustrating the in vitro responses of a squirrel monkey after three injections with p19 with Freunds Adjuvant, with alum and in the form of liposomes.
Figure 20A:
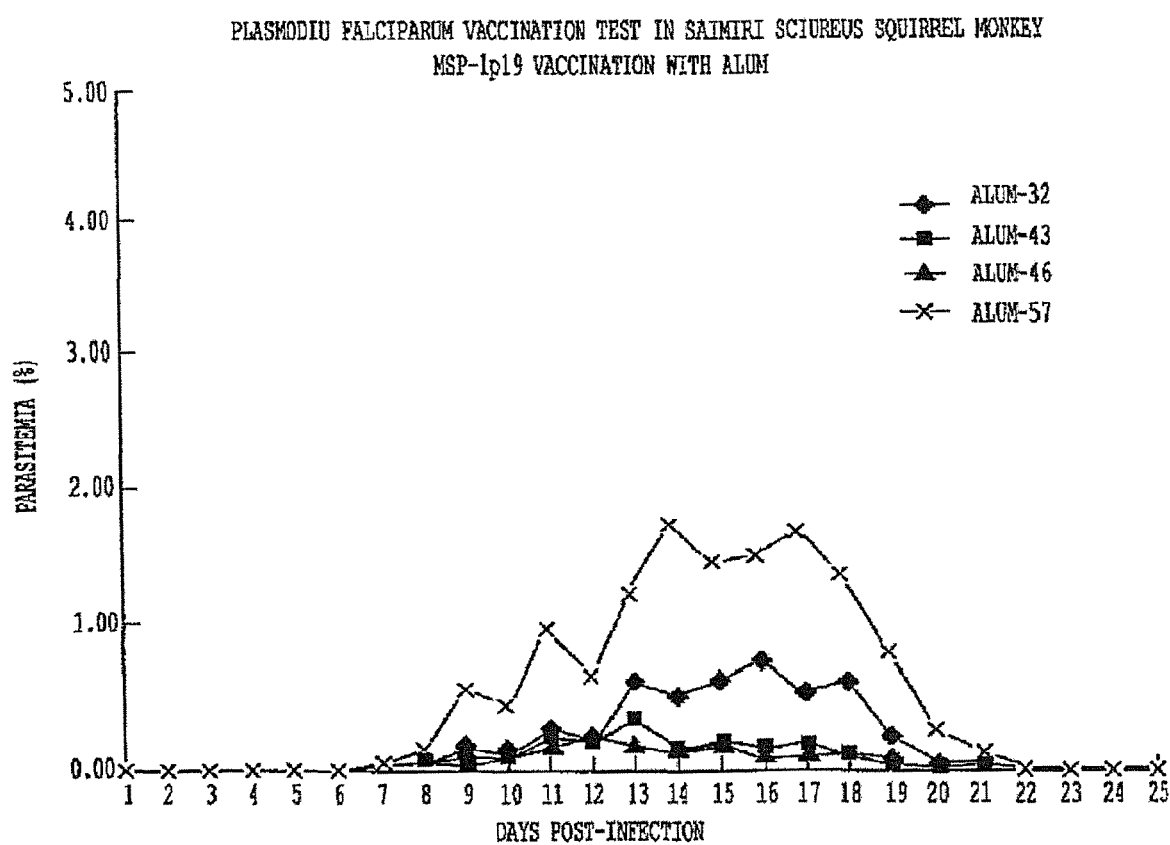
FIG. 20A is a graph illustrating the percent parasitemia versus days post infection in a squirrel monkey immunized with MPS-1 p19 and alum.
Figure 20B:
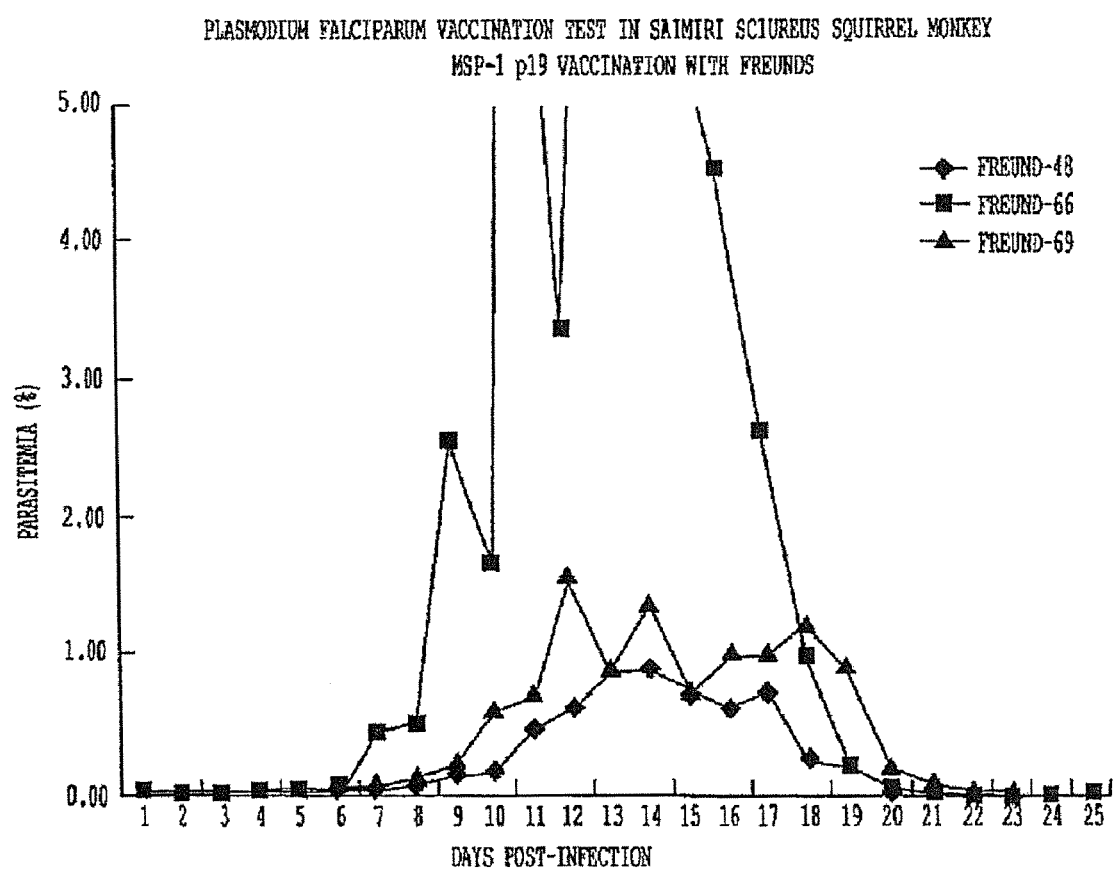
FIG. 20B is a graph illustrating the percent parasitemia versus days post infection in a squirrel monkey immunized with MPS-1 p19 and Freunds.
Figure 20C:
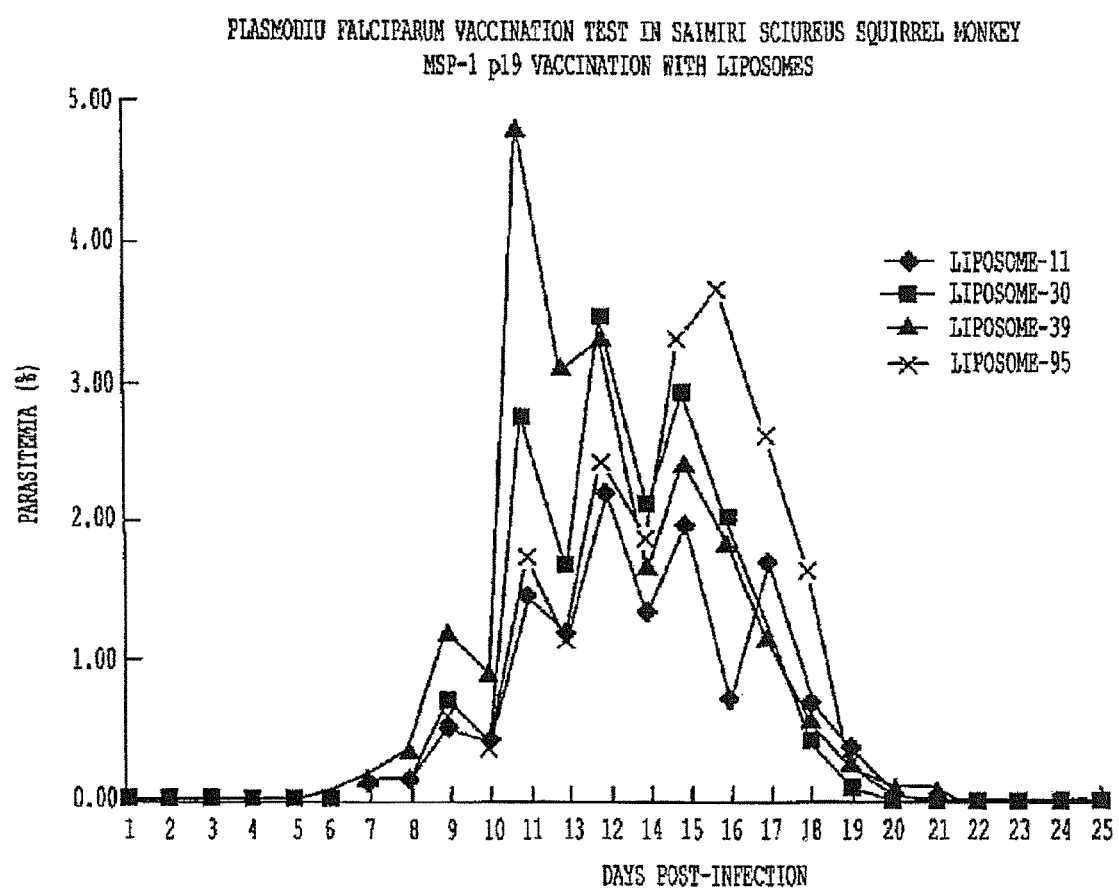
FIG. 20C is a graph illustrating the percent parasitemia versus days post infection in a squirrel monkey immunized with MPS-1 p19 with liposomes.
Figure 20D:
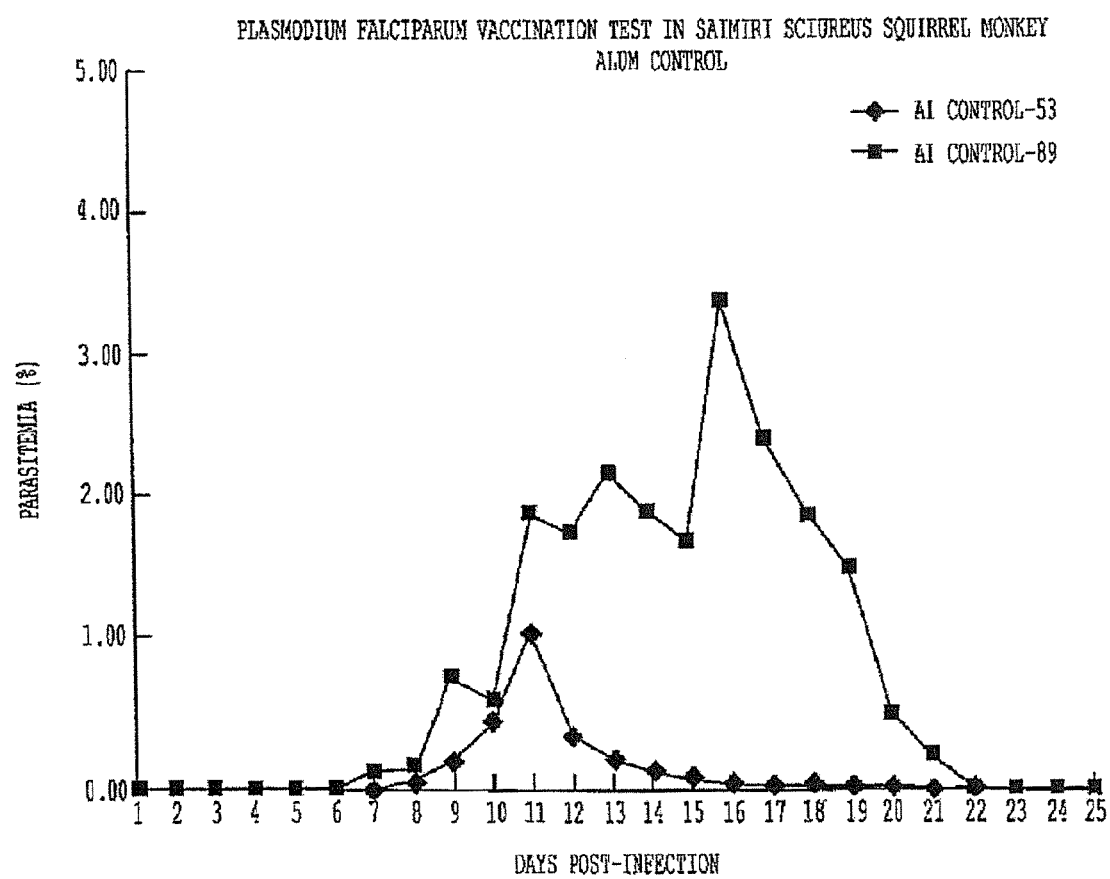
FIG. 20D is a graph illustrating the percent parasitemia versus days post infection in a squirrel monkey immunized with alum as the control.
Figure 20E:
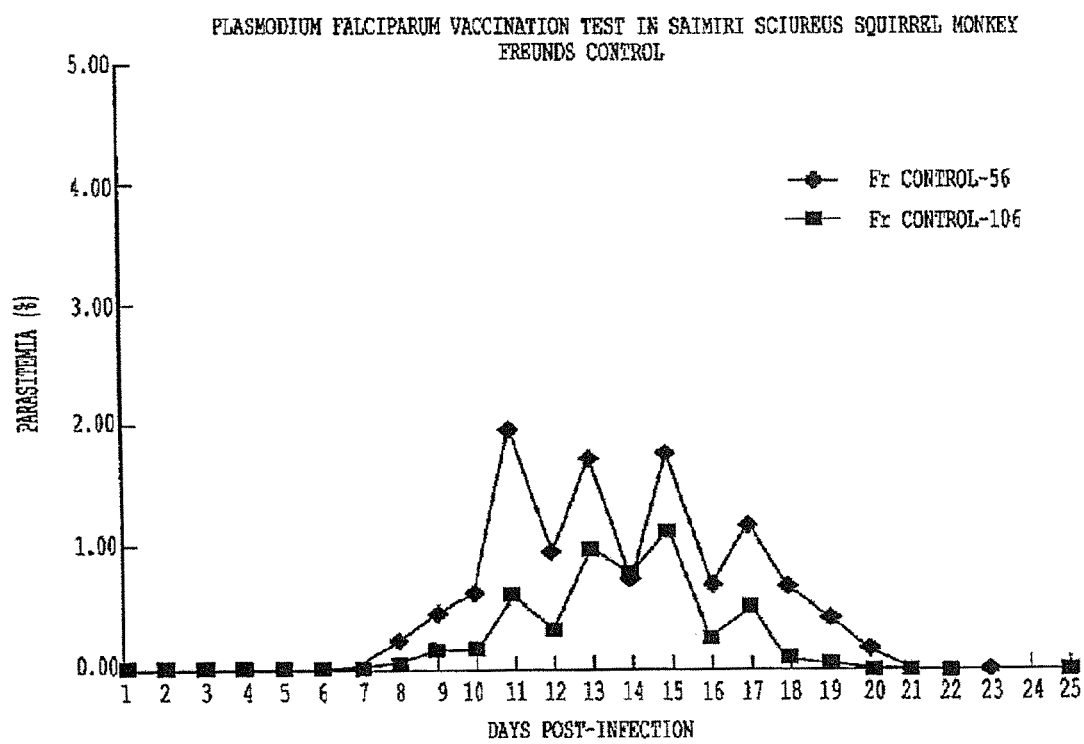
FIG. 20E is a graph illustrating the percent parasitemia versus days post infection in a squirrel monkey immunized with Freunds as the control.
Figure 20F:
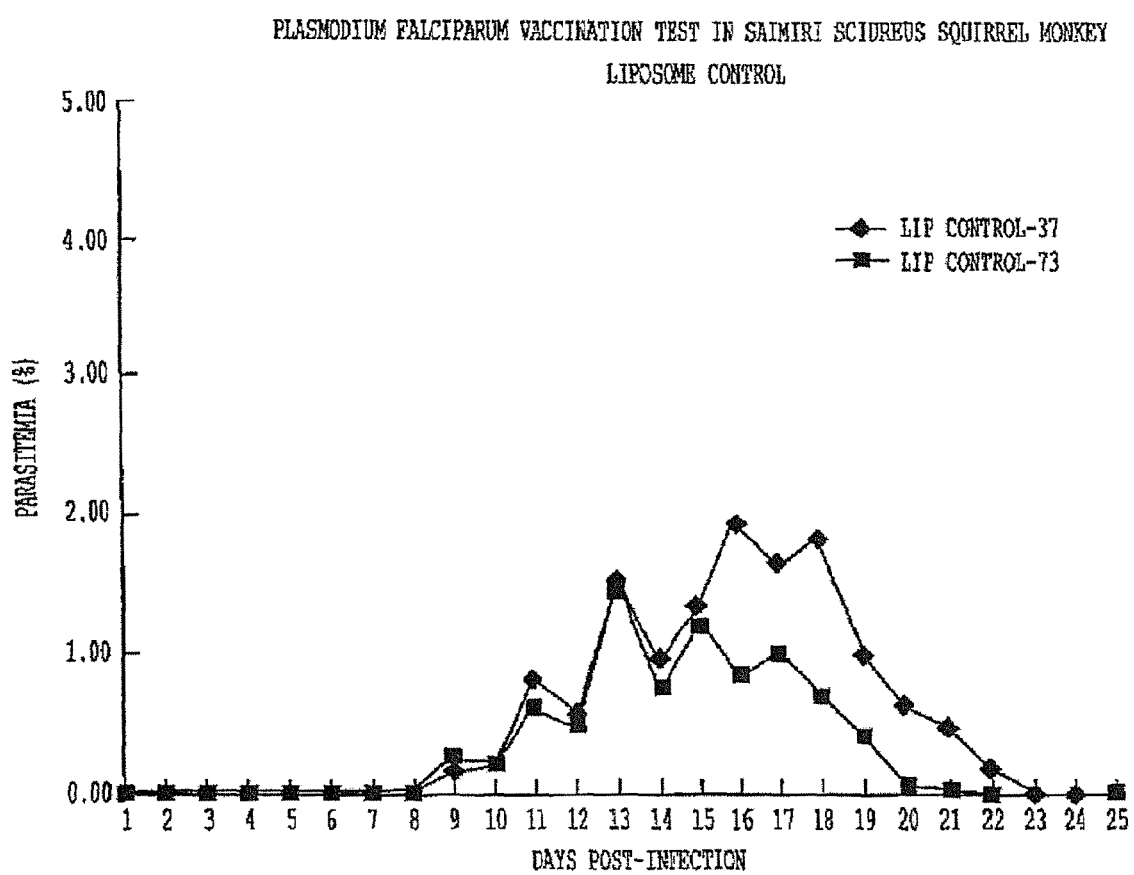
FIG. 20F is a graph illustrating the percent parasitemia versus days post infection in a squirrel monkey immunized with liposomes as the control.
Figure 20G:
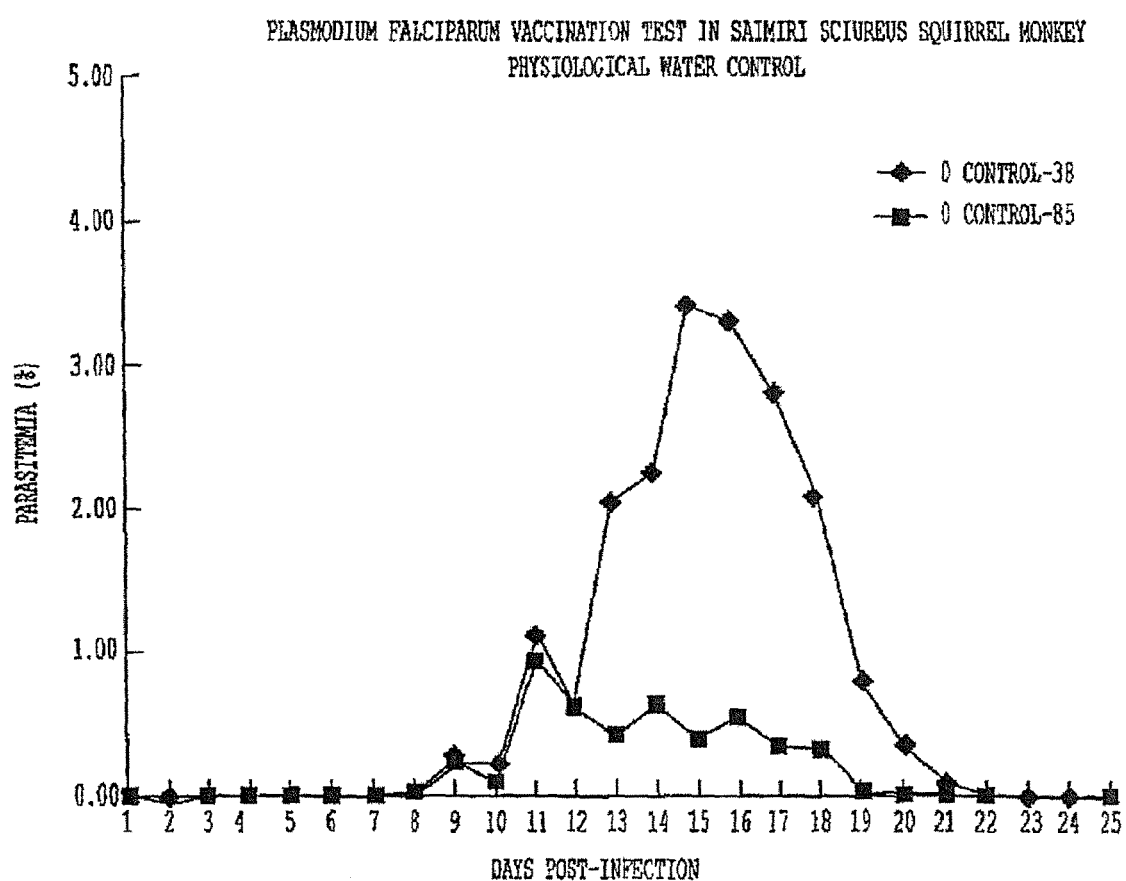
FIG. 20G is a graph illustrating the percent parasitemia versus days post infection in a squirrel monkey immunized with physiological water as the control.

FIG. 19B. The data for this Figure were derived from the squirrel monkey *P. falciparum* I vaccination test (FIG. 20 below). The numbers correspond to the individual monkeys noted in FIG. 20. The techniques and methods for this Figure were the same as for FIG. 19 except that the individual antiserum for each monkey was tested after three injections the day of the proof injection and the SHI antiserum was diluted by 1:250.

The results show that the antiserum for 4 monkeys vaccinated with p19 and alum reacted strongly and specifically with very high molecular weight complexes while the monkeys of other groups vaccinated with p19 and Freunds adjuvant or liposomes showed only a little reactivity as in the control reactivity with these complexes. Since the monkeys vaccinated with p19 and alum were also the best protected, this reactivity with the high molecular weight complexes appeared to indicate a protective effect, despite one monkey in the group not being protected with respect to the controls and that another was only partially protected.

The invention also, of course, concerns other applications, for example those described below with respect to certain of the examples, although these are not limiting in character.

The present invention relates to a purified polypeptide comprising or consisting essentially of a C-terminus MSP1 antigen from *Plasmodium* carrying a Glycosyl-phosphatidyl-inositol group (GPI).

By "consisting essentially of" means that other elements that are not necessary or material to the invention can be included in the immunogenic compositions, vaccines, and vectors.

With respect to the purified polypeptide "consisting essentially of" means that the amino acid sequence is limited to the exact sequence but the purified polypeptide can contain other elements that are not necessary or material to the invention.

The term "C-terminus MSP1 antigen" is used to describe a portion of the known MSP1 protein of *Plasmodium*, which is at the carboxy-terminus of said protein and has less than 200 amino acids, preferably less than 150 amino acids. In a particular embodiment of the present invention, said purified polypeptide from the MSP1 antigen is MSP1-19 peptide from *Plasmodium*. The MSP1-19 polypeptide (also designated as peptide) has been described in a specific example; the C-terminus MSP1 antigen from *Plasmodium* carries (or anchors) a Glycosyl-phosphatidyl-inositol group (GPI) which is linked by covalent bonding.

When, the purified polypeptide comprises said C-terminus MSP1 antigen, it is nevertheless a portion of the native MSP1 antigen, i.e. it has an amino acid sequence which is a fragment of the complete sequence of the MSP1 antigen.

In a particular embodiment of the present invention, the "C-terminus MSP1 antigen" is a fragment of the MSP1 C-terminal polypeptide, comprising or consisting from 10 to 200 amino acids and preferably from 10 to 150 amino acids.

In another particular embodiment of the present invention, the MSP1 antigen is a *Plasmodium falciparum* antigen or a *Plasmodium vivax* antigen.

Optionally, this C-terminus MSP1 antigen is recombined with a different peptide or polypeptide, e.g. a peptide or polypeptide originating from another antigen.

In a particular embodiment of the present invention, the purified polypeptide is a recombinant polypeptide expressed in a eukaryotic cell where it is anchored in the plasma membrane through a GPI group synthesized by said eucaryotic cell. The polypeptide of the invention carries the GPI group.

In yet a particular embodiment of the present invention. MSP1-19 peptide has the following amino-acid sequence:

```
                                             (SEQ ID NO 1)
VTHESYQELVKKLEAFEDAVLTGYEFNTIISKLIEGKFQDMLNISQHQCV

KKQCPENSGCFRHLDEREECKCLLNYKQEGDKCVENPNPTCNENNGGCDA

DAKCTEEDSGSNGKKITCECTKPDSYPLFDGIFCSGIFSS.
```

In a specific example, the purified polypeptide of the present invention is recognized by conformation-dependent antibodies directed against the MSP1-19 peptide. Conformation-dependent antibodies have been described in [11] and can be obtained after intraperitoneal immunization of BALB/c mice with Sf9 cells infected with a recombinant baculovirus coding for PfMSP1p19, or PvMSP1p19.

In a specific example, the MSP1-19 peptide reproduces the disulphide bonded double EGF-like domain structure of native MSP1p19. Said EGF-like domain, when folded correctly, possesses six disulphite bridges and appears extremely stable and highly resistant to proteolysis. Although this domain is shown to present considerable sequence variation in different *Plasmodium* species, its 3-dimensional structure and function nonetheless appear to be remarkably conserved [10]; [11]; [19]. EGF-like domains could particularly be involved in maintaining the characteristic properties of PfMSP1p19 protein as well as the immunological potency thereof.

MSP1p19 structural integrity is of critical importance in an immunogenic context because most, if not all, MSP1p19 B-cell epitopes appear to be non-linear and reduction sensitive, since irreversible reduction abolishes antibody recognition.

The purified polypeptide of the present invention can be expressed in insect cells, and purified from the plasma membrane of said cells, in conditions enabling the GPI anchor to be retained on expressed polypeptide.

In a particular embodiment of the invention the polypeptide can be produced in a baculovirus/insect cell expression system.

Insect cells such as *Spodoptera frugiperda* (Sf9) or *Trichoplusia ni* (High Five, H5) insect cells can be used for the expression of the polypeptide.

In a particular embodiment, the polypeptide of the invention has glycosylation groups. Glycosylation is discussed in examples.

The purification of the polypeptide is achieved having recourse to any known technique such as those described in the examples involving the use of detergents e.g. octyl β-glucoside and if required octyl RP-FPLC purification step.

Other eucaryotic cells can be used for the expression of the polypeptide of the invention, including yeast cells, mammalian cells.

In another aspect of the invention, the MSP1-19 peptide of the present invention is expressed with a His-tag and has the following sequence:

```
                                              (SEQ ID NO 2)
VTHESYQELVKKLEAFEDAVLTGYEFNTIISKLIEGKFQDMLNISQHQCV

KKQCPENSGCFRHLDEREECKCLLNYKQEGDKCVENPNPTCNENNGGCDA

DAKCTEEDSGSNGKKITCECTKPDSYPLFDGIFCSHHHHHHGIFSS.
```

A hexa-histidine tag near the C-terminus is useful for purification of the polypeptide using metalloaffinity chromatography. The GIFCS and GIFSS sequences are repeated immediately before and after the hexa-histidine tag to assure the GPI modification signal function.

The invention also relates to a purified variant of the polypeptide defined above, having at least 80% identity with the purified polypeptide of the present invention and modified with respect to said polypeptide as a result of amino acid substitution deletion or addition of a least one amino acid residue, with the proviso that the expressed variant retains the GPI group and the immunogenic properties of said purified polypeptide.

In a specific example, said variant has less than 200 amino acids, preferably less than 50 amino acids.

Such a variant can have the same length as the purified polypeptide of the invention, especially when it comprises substituted amino acid residues only. It can be shorter that the purified polypeptide of the invention, especially when amino acid residues are deleted, for instance it can have up to 10% deleted residues. It can also be longer, especially as a result of added residues, to the extent that it remains shorter than the MSP1 antigen, for example having at most 10% added residues with respect to the purified polypeptide of the invention.

Substitutions in the purified polypeptide of the invention, giving rise to a variant are preferably conservative substitutions.

The variant polypeptide is especially expressed from a polynucleotide which has a modified nucleotide sequence with respect to the nucleic acid molecule encoding the polypeptide of the invention.

The disclosure which is made in the present application, with respect to the so-called purified polypeptide of the invention, applies in the same way to the variant polypeptide.

Hence, to the exception of the above description of the variant polypeptide with respect to this defined purified polypeptide, when reference is made to the purified polypeptide it also concerns the variant.

The invention also relates to an immunogenic composition comprising the purified polypeptide of the present invention, and a pharmaceutically acceptable vehicle.

The present immunogenic composition can be injected as is, or for convenience of administration, can be added to a pharmaceutically acceptable carrier. Suitable pharmaceutically acceptable carriers will be apparent to those skilled in the art, and include water and other polar substances, including lower molecular weight alkanols, polyalkanols such as ethylene glycol, polyethylene glycol, and propylene glycol as well as non-polar carriers.

The inventors have observed that the GPI group which is present on the purified polypeptide of the invention has an impact on the immunogenicity of the polypeptidic part of the polypeptide, especially provides an adjuvant effect to the immunogenic amino acid sequence.

Accordingly, the purified polypeptide of the invention can be used without adding substances usually added in vaccine compositions to increase the immune response.

In a specific example, the immunogenic composition is thus devoid of additional compounds known as adjuvant of the immune response.

The invention also relates to a vaccine against a *Plasmodium* infection comprising or consisting of an active principle which is the purified polypeptide of the present invention.

The term "vaccine" is used throughout the specification to describe a preparation intended for active immunological prophylaxis, i.e. capable of eliciting an immune response e.g. a cellular and/or humoral response which protects against infection by *Plasmodium falciparum* or its consequences.

The method of administering the vaccine(s) according to the present invention may vary and include intravenous, buccal, oral, transdermal and nasal, among others, but intramuscular or subcutaneous administration is the most common route of administration.

Vaccine compositions of the invention are intended for administration to human.

The present vaccine can be injected as is, or for convenience of administration, can be added to a pharmaceutically acceptable carrier. Suitable pharmaceutically acceptable carriers will be apparent to those skilled in the art, and include water and other polar substances, including lower molecular weight alkanols, polyalkanols such as ethylene glycol, polyethylene glycol, and propylene glycol as well as non-polar carriers.

The active principle which is the purified polypeptide of the present invention should be in an effective amount. The term "effective amount" refers to an amount or concentration of active principle effective to produce a protective immune with respect to the disease malaria. One or several doses may be necessary to achieve the protection sought.

In general, an effective amount of the immunogenic purified polypeptide which is administered to a human patient will vary depending upon a number of factors associated with that patient, including whether the patient previously has been exposed to *Plasmodium falciparum* before. An effective amount of the immunogenic purified polypeptide can be determined by varying the dosage of the product and measuring the resulting cellular and humoral immune and/or therapeutic responses, prior to administration.

In a specific example, said vaccine is devoid of additional compounds known as adjuvant of the immune response.

In a specific example, said vaccine further comprises polymer additives.

One or several further antigens of *Plasmodium* can be added as active principle in said vaccine. Such additional antigens include LSA antigens (including either LSA1, LSA3, LSA5 or combinations thereof), MSP-3, or GLURP.

Said vaccine can be used against infection by *Plasmodium falciparum*.

The invention also relates to a nucleic acid molecule which encodes the amino acid sequence of the purified polypeptide of the present invention.

In a particular embodiment of the invention, the nucleic acid molecule, encodes the amino acid sequence of the purified polypeptide, having the following amino acid sequence:

(SEQ ID NO 2)
VTHESYQELVKKLEAFEDAVLTGYEFNTIISKLIEGKFQDMLNISQHQCV

KKQCPENSGCFRHLDEREECKCLLNYKQEGDKCVENPNPTCNENNGGCDA

DAKCTEEDSGSNGKKITCECTKPDSYPLFDGIFCSHHHHHHGIFSS.

In order to produce the polypeptide of the invention, the amino acid sequence of MSP1-19 expressed in the recombinant cells is transported to the cell membrane and processed to enable GPI binding. Therefore the nucleic acid molecule encoding the polypeptide of the invention comprises a nucleic acid molecule which encodes a signal peptide having the following amino acid sequence: MKIIFFLCSFLFFIINTQC (SEQ ID NO 3), and a nucleic acid molecule which encodes an anchor peptide, that signal for GPI addition having the following amino acid sequence: SSNFLGISFLLILMLILYSFI (SEQ ID NO 4).

According to this aspect of the invention, the nucleic acid molecule of the present invention therefore encodes the following amino acid sequence:

(SEQ ID NO 6)
MKIIFFLCSFLFFIINTQCVTHESYQELVKKLEAFEDAVLTGYEFNTIIS

KLIEGKFQDMLNISQHQCVKKQCPENSGCFRHLDEREECKCLLNYKQEGD

KCVENPNPTCNENNGGCDADAKCTEEDSGSNGKKITCECTKPDSYPLFDG

IFCSHHHHHHGIFSSSSNFLGISFLLILMLILYSFI.

In another embodiment of the invention, the nucleic acid molecule (polynucleotide) of the present invention encodes the amino acid sequence of SEQ ID NO 20.

The sequences which are underlined correspond to putative N-glycosylation sites.

In the present invention, an "anchor peptide" comprises a peptide sequence, for example of about 10 to 35 residues in length which is generally expressed at the carboxy-terminus of the C-terminus MSP1 antigen of the present invention.

The term "signal peptide" is used to describe a 7-30 unit amino acid peptide sequence, preferably about a 15-26 unit amino acid peptide sequence.

The signal peptide is generally expressed at the N-terminus of the C-terminus MSP1 antigen of the present invention.

The nucleic acid molecule of the invention encompasses DNA, either double-stranded or single-stranded DNA depending on the use, cDNA or even RNA.

In a specific example, the nucleic acid molecule of the present invention is optimised for codon usage appropriate in baculovirus expression vector.

The invention also relates to a nucleic acid molecule which can have a nucleotide sequence selected from the sequences presented in the table 1 below:

TABLE 1

Primers used for the constructions of recombinant PfMSP1p19 and PfMSP1p19 + A expressing sequences

| name | Sequence |
|---|---|
| Sig1 SEQ ID No. 7 | CCCGGATCCGAAAATGAAGATCATATTCTTTT TGTGTTCGTTCCTCTTC |
| Sig2 SEQ ID No. 8 | TCTCGTGGGTCACACATTGCGTGTTGATGATG AAGAAGAGGAACGAAC |
| Sig3 SEQ ID No. 9 | GTGTGACCCACGAGAGCTACCAAGAGCTCGTC AAGAAACTGGAGGCCTTC |
| Sig4 SEQ ID No. 10 | CCCGAATTCGTAGCCGGTCAACACCGCGTCCT CGAAAGGCCTCCAGTTTC |
| Bac1 SEQ ID No. 11 | GGGGAATTCAACATCTCGCAGCACCAATGCGT GAAAAAACAATGTCCCGAGAACTCTGGCTGTT TCAGACACTTGGACGAGAGA |
| Bac2 SEQ ID No. 12 | ACAGGTCGGGTTGGGGTTCTCCACGCACTTGT CGCCCTCCTGTTTGTAGTTCAGCAGACATTTA CACTCCTCTCTCGTCCAAGTG |
| Bac3 SEQ ID No. 13 | CCCAACCCGACCTGTAACGAGAACAACGGCGG CTGTGACGCCGACGCCAAATGCACCGAGGAGG ACTCGGGCAGCAACGGCAAG |
| Bac4 SEQ ID No. 14 | AGAGGAGCTGCAGAAGATGCCGTCGAACAGCG GGTACGAGTCGGGTTTGGTACACTCACACGTG ATTTTCTTGCCGTTGCTGCC |
| Bac5 SEQ ID No. 15 | TTCTGCAGCTCCTCTAACTTCTTGGGCATCTC GTTCTTGTTGATCCTCATGTTGATCTTGTACA GCTTCATTTAATAAAGATCTCCC |
| Bac6 SEQ ID No. 16 | GGGAGATCTTTATTAAATGAAGC |
| Bac7 SEQ ID No. 17 | GGGGAATTCAACATCTCGCAGC |
| Bac8 SEQ ID No. 18 | GCCCAAAGATCTTTATTAGCTGCAGAAGATGC CGTCGAACAGCGG |

The invention further relates to the polynucleotides corresponding to the amplification products obtained with the primers of Table 1.

The invention also concerns the polypeptides expressed from said amplification products.

The invention also relates to an expression vector for the expression of a purified polypeptide of the present invention comprising one of the nucleic acid molecules described above.

The term "expression vector" is used to describe the means by which nucleic acid, including DNA, cDNA, RNA or variants thereof, more preferably DNA fragments, encoding for a specific peptide or protein, may be introduced into a cell, especially an eucaryotic cell to express or produce the desired protein. Such vectors include any vectors into which a nucleic acid sequence insert encoding for polypeptide of the present invention, is inserted, under the control of sequences necessary for replication of the vector and expression of the insert nucleic acid molecule.

In the present invention, the vector is for example a baculovirus vector, and, in a specific embodiment, a baculovirus vector of the type "BACULOGOLD™ viral DNA" commercialized by PHARMINGEN™.

In order to express the desired protein or peptide sequence, the expression vector should contain at least one promoter, at least one operator, at least one terminator codon, and any other sequences which are necessary or useful for the efficient transcription and subsequent translation of the nucleic acid from the vector. These operational elements are well known to those of ordinary skill in the art.

In a specific example, said expression vector is a baculovirus expression vector.

The invention also relates to an expression system for the expression of the purified polypeptide of the present invention comprising said baculovirus expression vector and insect cells.

In a specific example, said cells are *Spodoptera frugiperda* (Sf9) or *Trichoplusia ni* (High Five, INVITROGEN®) insect cells.

The invention also relates to the recombinant baculovirus PfMSP1p19/His/GPI deposited on November 10, 2005 under the accession number CNCM I-3515 at the Collection Nationale de Cultures de Microorganismes (C.N.C.M.) INSTITUT PASTEUR, 25 rue du Docteur Roux, F-75724 PARIS CEDEX 15, and containing the nucleic acid sequence encoding the polypeptide of SEQ ID NO 6. The nucleic acid sequence encoding the polypeptide of the recombinant baculovirus PfMSP1p19/His/GPI was constructed from the nucleotide sequence encoding the native MSP1p19 protein of *Plasmodium falciparum*.

The invention also relates to the recombinant baculovirus PvMSP1p19/His/GPI deposited on Nov. 10, 2005 under the accession number CNCM I-3516 at the Collection Nationale de Cultures de Microorganismes (C.N.C.M.) INSTITUT PASTEUR, 25 rue du Docteur Roux, F-75724 PARIS CEDEX 15, and containing the nucleic acid sequence encoding the polypeptide of SEQ ID NO 20. The nucleic acid sequence encoding the polypeptide of the recombinant baculovirus PvMSP1p19/His/GPI was constructed from the nucleotide sequence encoding the native MSP1p19 protein of *Plasmodium vivax*.

Therapy

The recombinant molecule PfMSP1p19 can be used to produce specific antibodies which can possibly be used by passive transfer for therapeutics for severe malaria due to *P. falciparum* when there is a risk of death.

Diagnostics

The recombinant molecules PvMSP1p42. PvMSP1p19 and PfMSPp19 derived from baculovirus can and have been used to produce specific murine monoclonal antibodies. These antibodies, in combination with polyclonal anti-MSP1p19 antisera originating from another species such as the rabbit or goat can form the basis of a semi-quantitative diagnostic test for malaria which can distinguish between malaria due to *P. falciparum*, which can be fatal, and malaria due to *P vivax*, which is generally not fatal. The principle of this test is to trap and quantify any MSP-1 molecule containing the p19 portion in the blood.

In this context, the advantages of the MSP1p19 molecule are as follows:
(i) it is both extremely well conserved in the same species and sufficiently divergent between different species to enable specific species reactants to be produced. No cross reaction has been observed between antibodies derived from PfMSP1p19 and PvMSP1p19;
(ii) the function of MSP1p19, while not known with precision, seems to be sufficiently important that this molecule does not vary significantly or is deleted without lethal effect for the parasite;
(iii) it is a major antigen found in all merozoites and thus it must in principle be detectable even at low paras)temia and proportionally to the parasitemia;
(iv) since the recombinant MSP1p19 molecules derived from baculovirus appear to reproduce more of the native structure of MSP1p19, the antibodies produced against these proteins will be well adapted to diagnostic use.

The microorganisms identified below have been deposited at the Collection Nationale de Culture de Microorganisms de L'Institut Pasteur (CNCM) under Rule 6.1 of the Treaty of Budapest on 1 Feb. 1996. under the following registration numbers:

| Identification reference | Registration numbers |
| --- | --- |
| PvMSP1p19A | 1-1659 |
| PvMSP1p19S | 1-1660 |
| PfMSP1p19A | 1-1661 |
| PfMSP1p19S | 1-1662 |
| PcMSP1p19S | 1-1663 |

The invention also concerns the use of these antibodies, preferably fixed to a solid support (for example for affinity chromatography) for the purification of type p19 peptides initially contained in a mixture.

Purification means bringing this mixture into contact with an antibody, dissociating the antigen-antibody complex and recovering the purified p19 type peptide.

The invention also concerns vaccine compositions, also comprising mixtures of proteins or fragment, in particular mixtures of the type:
  *P. falciparum* p19 and *P. vivax* p19;
  *P. falciparum* p19 and *P. falciparum* p42, the latter if necessary being deprived of its most hypervariable regions;
  *P. vivax* p19 and *P. vivax* p42, the latter if necessary being deprived of its most hypervariable regions;
  *P. falciparum* p19 and *P. falciparum* p42, the latter if necessary being deprived of its most hypervariable regions, and *P. vivax* p19 and *P. vivax* p42, the latter if necessary being deprived of its most hypervariable regions.

In the present case, the most hypervariable regions are defined as region II or region II and all or part of region III, the portion of region III which is preferably deleted being that which is juxtaposed to region II (the conserved portion being located to the side of the C-terminal of p33, close to the p19). Regions II and III are illustrated in FIG. 4.

The invention is not limited to the production of human vaccine, it is also applicable to the production of veterinary vaccine compositions using the corresponding proteins or antigens derived from parasites which are infectious for mammals and products under the same conditions. It is known that infections of the same type, babesiosis, also appear in cattle, dogs and horses. One of the antigens of the Babesia species has a high conformational homology (in particular in the two EFG-like and cysteine-rich domains) and functional homology with a protein portion of MSP-1 [(36), (37) and (38)].

Examples of veterinary vaccines using a soluble antigen against such parasites have been described (39).

It goes without saying that the p19s used in these mixtures can also be modified as described in the foregoing when considered in isolation.

The invention also concerns hybridomas secreting specific antibodies selectively recognizing the p19 of a MSP-1 protein in the merozoite form of a Plasmodium type parasite which is infectious for man other than Plasmodium vivax and which does not recognize Plasmodium vivax.

In particular, these hybridomas secrete monoclonal antibodies which do not recognize Plasmodium vivax and which specifically recognize Plasmodium falciparum p19.

The invention also concerns hybridomas secreting specific antibodies selectively recognising the p19 of a MSP-1 protein in the merozoite form of a Plasmodium type parasite which is infectious for man other than Plasmodium vivax and which does not recognise Plasmodium vivax.

In particular, these hybridomas secrete monoclonal antibodies which do not recognise Plasmodium vivax and which specifically recognise Plasmodium falciparum p19.

The invention also concerns a hybridoma characterized in that it produces a specific antibody which specifically recognizes the p19 of P. vivax and the p19 of P. cynomolgi. AF10-3 hybridoma has been constructed from the X63 Ag8653 myeloma producing IgG 2b/k recognising the p42 glycoprotein of Plasmodium vivax.

EXAMPLES

Example 1

Characterization of Secreted and GPI-modified Baculovirus Recombinant Plasmodium falciparum C-terminal Merozoite Surface Protein 1 (PfMSP1p19), a Leading Malaria Vaccine Candidate Here we have focused on the baculovirus/insect cell expression system for the production of two recombinant analogs of PfMSP1p19 to use in preclinical validation studies that would justify undertaking human clinical trials for this promising malaria vaccine candidate. In this context the baculovirus expression system has two major advantages. First, and most importantly, it appears to reproduce accurately and quantitatively the highly complex disulphide bonded double EGF domain structure of native MSP1p19. Indeed, the crystal structures of both P. cynomolgi and P. falciparum MSP1p19 were solved using soluble baculovirus produced proteins lacking the extreme C-terminal hydrophobic amino acid sequence, and consequently were secreted into the culture supernatants [38]; [10]; [11]. MSP1p19 structural integrity is of critical importance in a vaccine context because most, if not all, MSP1p19 B-cell epitopes appear to be non-linear and reduction sensitive, since irreversible reduction abolishes antibody recognition. Secondly, we show unambiguously here that in Sf9 or Hi5 insect cells infected with recombinant baculovirus containing the entire C-terminal PfMSP1 coding sequence. PfMSP1p19 is found exclusively on the cell surface or in an intracellular location, rather than secreted into cell culture supernatants. PfMSP1p19 expressed on the cell surface can be at least partially solubilized by phospho-inositol phospho-lipase C (PIPLC), which specifically cleaves GPI structures. PfMSP1p19-GPI has been purified and characterized prior to use in comparative immunogenicity studies (Example 2). The soluble baculovirus PfMSP1p19 described here is currently undergoing cGMP process development for use in human clinical trials.

1-1-Materials and Methods

Insect Cell and Baculovirus Culture

Spodoptera frugiperda (Sf9) and Trichoplusia ni (High Five, INVITROGEN®) insect cells were grown in monolayer or suspension cultures at 27° C., respectively in SF-900 ™ serum-free medium (GIBCO®-BRL) or INSECT-XPRESS™protein-free medium (BIOWHITTAKER®) supplemented with 4 mM glutamine (GIBCO®-BRL). High titer viral stocks ($10^8$ pfu/ml) were produced in Sf9 cells cultured in SF-900 ™ medium supplemented with 5% foetal calf serum (Eurobio; decomplemented 30 min at 56° C.) and stored at 4° C.

Construction of Recombinant Baculovirus

To optimize PfMSP1p19 expression in the baculovirus system, analogs of the P. falciparum genome sequences used (Uganda-Palo-alto isolate, [39]) for the constructions described below (28% G-C), were synthesized with a codon usage corresponding more closely to that of the baculovirus polyhedrin gene (57% G-C), which is replaced by recombinant sequences. Table 2 shows a comparison of parasite genome codons and those used in the synthetic sequences derived from PfMSP1 (50% G-C).

First, a recodoned fragment corresponding to the PfMSP1 signal sequence (19 residues) as well as the 24 conserved N-terminal amino acid residues of processed PfMSP1 (VTH—TGY) was synthesized using 4 overlapping oligos:

```
Pfsig1 of SEQ ID NO 7 (49 mer) =
CCCGGATCCGAAAATGAAGATCATATTCTTTTTGTGTTCGTTCCTCTTC;

Pfsig2 of SEQ ID NO 8 (48 mer) =
TCTCGTGGGTCACACATTGCGTGTTGATGATGAAGAAGAGGAACGAAC;

Pfsig3 of SEQ ID NO 9 (50 mer) =
GTGTGACCCACGAGAGCTACCAAGAGCTCGTCAAGAAACTGGAGGCCTTC;

Pfsig4 of SEQ ID NO 10 (50 mer) =
CCCGAATTCGTAGCCGGTCAACACCGCGTCCTCGAAAGGCCTCCAGTTTC.
```

Constructions were assembled as previously described [38] based on restriction sites included in the oligos used to construct the synthetic gene, such that the sequence coding for PfMSP1 signal and the 43 N-terminal amino acids of MSP1 of Plasmodium Falciparum were inserted into the Bam HI-Eco RI site on the pVL1393 tansfer vector (INVITROGEN®), creating Pfsig-pVL1393. The 43 N-terminal amino acids inserted in Pfsig-pVL1393 correspond to the fragment of MSP1 ranging from $Met_1$ to $Tyr_{43}$, with a substitution of Leu to Phe in position 35. Additionally, the 43 N-terminal amino acids are followed by GluPhe, due to the EcoRI site that constitutes the bond with a sequence coding for a MSP1 fragment of *P. falciparum* between $Asn_{1597}$ and $Ser_{1705}$.

In a second step, the synthetic gene corresponding to the PfMSP1p19 naturally processed C-terminal fragment (NISQH on N-terminus) was constructed using a combination of long overlapping oligonucleotides and PCR as shown in FIG. 1. The sequences of the oligo nucleotides were as follows:

```
Bac1 of SEQ ID NO 11 (84 mer) =
5'GGGGAATTCAACATCTCGCAGCACCAATGCGTGAAAAAACAATGTCC

CGAGAACTCTGGCTGTTTCAGACACTTGGACGAGAGA 3';

Bac2 of SEQ ID NO 12 (87 mer) =
5'ACAGGTCGGGTTGGGGTTCTCCACGCACTTGTCGCCCTCCTGTTTG

TAGTTCAGCAGACATTTACACTCCTCTCTCGTCCAAGTG 3';

Bac3 of SEQ ID NO 13 (84 mer) =
5'CCCAACCCGACCTGTAACGAGAACAACGGCGGCTGTGACGCCGAC

GCCAAATGCACCGAGGAGGACTCGGGCAGCAACGGCAAG 3';

Bac4 of SEQ ID NO 14 (84 mer) =
5'AGAGGAGCTGCAGAAGATGCCGTCGAACAGCGGGTACGAGTCGGG

TTTGGTACACTCACACGTGATTTTCTTGCCGTTGCTGCC 3';

Bac5 of SEQ ID NO 15 (87 mer) =
5'TTCTGCAGCTCCTCTAACTTCTTGGGCATCTCGTTCTTGTTGATCCTC

ATGTTGATCTTGTACAGCTTCATTTAATAAAGATCTCCC 3';

Bac6 of SEQ ID NO 16 (23 mer) =
5'GGGAGATCTTTATTAAATGAAGC 3';

Bac7 of SEQ ID NO 17 (22 mer) =
5' GGGGAATTCAACATCTCGCAGC 3';

Bac8 of SEQ ID NO 18 (45 mer) =
GCCCAAAGATCTTTATTAGCTGCAGAAGATGCCGTCGAACAGCGG.
```

The product obtained using Bac6 and Bac7 for PCR corresponded to the complete C-terminal MSP1 sequence including the 21 hydrophobic amino acids that signal for GPI addition followed by 2 consecutive TAA stop codons. A construction designed to carry both a hexa-histidine tag near the C-terminus for purification using metalloaffinity chromatography, and the PfMSP1 hydrophobic sequence signaling for GPI modification, was then produced using a 127mer long

```
oligo
(GCCGTAGAAGACGTCGGTGGTAGTGGTAGTGGTACCGTAGAAGTCGTCG

AGGAGATTGAAGAACCCGTAGAGCAAGAACAACTAGGAGTACAACTAGAA

CATGTCGAAGTAAATTATTTCTAGACCC) of SEQ ID NO 21
``` and PCR to place the recodoned hydrophobic PfMSP1 C-terminal sequence after the hexa-histidine codons (FIG. 2). The GIFCS and GIFSS codons were repeated immediately before and after the hexa-his tag to assure the GPI modification signal function, while retaining the cys necessary for EGF domain structure in the former, and changing cys to ser in the latter to avoid undesirable S—S bonding (FIG. 2). This construct included, in addition, an extension of 16 amino acid residues upstream from the NISQH processed p19 fragment (Palo Alto allele=NTIISKLIEGKFQDML), which was made using a <<forward extension>> oligo (73mer) of SEQ ID NO 22: 5'CCGGAATTCAACACGATCATCTCGAAAT-TGATCGAGGGCAAATTCCA AGACATGTTGAA-CATCTCGCAGCACC 3'. After amplification, the resulting DNA fragment was then cloned into the EcoRI/BglII site of Pfsig-pVL1393 containing the signal peptide of *P. falciparum*, creating GPI-PfMSP1p19-pVL1393 coding for the anchored form of MSP1-p19. The product obtained using Bac7 and Bac8 corresponded to the C-terminus of the soluble secreted form of PfMSP1p19, lacking the C-terminal 21 hydrophobic residues, also with 2 TAA stop codons. PfMSP1p19 constructs designed to be secreted with a C-terminal hexa-histidine tag were produced by PCR from the synthetic gene using a <<reverse>> oligo encoding the soluble FCS PfMSP1p19 C-terminus followed by 6 histidine codons and the double TAA stop codons (57mer) of SEQ ID NO 23: 5' GGGAGATCTTTATTAATGGTGATGGT-GATGGTGGCTGCAGAAGATGCC GTCGAACAG 3'. This constructs including also the extension of 16 amino acid residues upstream from the NISQH processed p19 fragment made as described above. The final plasmid, coding for the secreted form of MSP1-p19 and called PfMSP1p19-pVL1393, was then obtained by cloning this fragment into EcoRI/BGLII cut Pfsig-pVL1393.

The only non-PfMSP1 sequences in these constructs are the EF residues coded by the EcoRI restriction site joining the N-terminal and C-terminal portions of the MSP1 gene, and the hexa-his purification tag. The both sequences, verified by PCR amplification and sequencing, are then similar except that the one coding for the anchored form pf19+A include the glycosylphosphatidylinositol (GPI) anchor signal sequence at the C terminal end, after the His-tag. Recombinant virus were obtained by gently mixing 15 µg of each transfert vector with 50 ng of BACULOGOLD™ viral DNA (PHARMINGEN™) in 1.5 ml of TC100 medium (GIBCO®) supplemented with 4 mM glutamine (GIBCO®) and 50 µg/ml of gentamycine (GIBCO®) with 50 µl of DOTAP (Liposomal Transfection Reagent, Roche) in 1.5 ml of the same medium. After a 10 min. incubation step, this mix was then added to 2.5 $10^6$ Sf9 cells in T-25 culture flasks and cultured for 6 days with one change of medium after 24 h. Recombinant virus was then isolated from the culture supernatant by plaque assay using standard methods [40] and amplified as described above.

The recombinant virus PvMSP1p19/His/GPI was constructed in accordance with the method described above for PfMSP1p19/His/GPI construction. Similary, PvMSP1p19/His/GPI was constructed from the BACULOGOLD™ vector (PHARMINGEN™) and a transfer vector pVL1393 (INVITROGEN®), coding for the first amino acids of MSP1 of *Plasmodium vivax* (Belem isolate [121]) from $Met_1$ to $Asp_{32}$. These amino acids are followed by GluPhe, due to the EcoRI site which constitutes bond with a sequence coding for a MSP1 fragment of *P. vivax* between $Ile_{1602}$ and $Ser_{1704}$.

The resulting sequence is followed by a sequence encoding six Histidine residues (hexa histidine) and by a sequence coding for the fragment GVFSSSSSFLSLSFLLLMLL-FLLCMEL, containing the C. terminus of PvMSP1 carrying the signal sequence for the addition of a GPI moiety. Finally, the above construction is ended by two TAA stop codons.

The construct encoding the secreted form of the protein PfMSP1p19 is available at the Collection Nationale de Cultures de Microorganismes (C.N.C.M.), INSTITUT PAS- TEUR, 25 rue du Docteur Roux, F-75724 PARIS CEDEX 15, under the accession number I-2041, which was deposited on Jun. 18, 1998.

The construct PfMSP1p19/His/GPI, encoding the *Plasmodium falciparum* protein PfMSP1p19+A (including the anchor GPI), is available at the Collection Nationale de Cultures de Microorganismes (C.N.C.M.), INSTITUT PASTEUR, 25 rue du Docteur Roux, F-75724 PARIS CEDEX 15, and was deposited on Nov. 10, 2005, under the accession number I-3515.

The construct PvMSP1SP1p19/His/GPI, encoding the *Plasmodium vivax* protein PfMSP1p19+A (including the anchor GPI), is available at the Collection Nationale de Cultures de Microorganismes (C.N.C.M.), INSTITUT PASTEUR, 25 rue du Docteur Roux, F-75724 PARIS CEDEX 15, and was deposited on Nov. 10, 2005, under the accession number I-3516.

PfMSP1p19/His/GPI and PvMSP1p19/His/GPI constructs are grown in a SF-900 ™ II culture medium comprising L-Glutamine (GIBCO®, INVITROGEN® Corp.), with 2 mM L-Glutamine (GIBCO®, INVITROGEN® Corp.), 50 µg/ml Gentamicin (GIBCO®, INVITROGEN® Corp.), 5% Foetal Calf Serum, Sodium Bicarbonate, at pH 6.2, at a temperature of 27-28° C.

Virus suspensions are prepared from monolayers of *Spodoptera frugiperda* (SP9) cells cultures grown in complete medium, with 5% Foetal Calf serum. Cells cultures are inoculated with a small amount of viral suspension, or with a plaque or with the content of a microtiter plate well originating from a limiting dilution cloning procedure.

Cultures are incubated at 27-28° C. until the cells lysis i.e., until about 5 to 6 days. Infection is ascertained by the following criteria of evidence: enlarged cells and nuclei, granular appearance and cells lysis after a few days. Culture supernatants are then centrifuged 10 minutes at 4000× g to remove cells fragments.

Finally, titration of the viruses is achieved by the limiting dilution method. The expected titer is about $10^7$ to $10^8$ pfu/ml, and about 6 days are required to allow reading of the results.

Expression of Recombinant Proteins

Around $1.6 \cdot 10^6$ insect cells/ml (either HF or Sf9 cells) were infected with recombinant virus (moi=10) and allowed to grow in monolayer or in suspension cultures, at 27° C. for 2 or 3 days for pf19 and pf19+A, respectively. Infections were performed in the same medium as non-infected cells in the presence of 50 µg/ml gentamycine.

Purification of Recombinant Proteins

Secreted proteins. Culture media were centrifuged 15 min. at 3000 rpm to remove cells and cellular debris and dialysed against 20 mM tris-HCl (pH8)/500 mM NaCl before purification on an AKTA™ purifier system (AMERSHAM PHARMACIA BIOTECH™), with passage over a 1 ml Hitrap™ chelating HP column (AMERSHAM PHARMACIA BIOTECH™) loaded with CaCl2 0.1 M and equilibrated in the same buffer. The column was extensively washed and bound protein eluted with a linear gradient from 0 to 100% of 20 mM tris-HCL (pH8)/300 mM NaCl containing 200 mM imidazole. Fractions (1 ml) were than collected and 13 µl samples analysed by electrophoresis and western blotting.

Anchored protein. Cells were removed from culture by centrifugation (15 min. at 3000 rpm), washed twice in Phosphate buffered saline (PBS) and frozen at −20° C. in the presence of 1× protease inhibitors (Complete EDTA-free, Roche). Membrane-proteins were solubilised in 4 volumes of 60 mM octyl β-glucopyranoside in 20 mM Tris-HCl pH8 in presence of 1× Complete EDTA-free proteases inhibitors (Roche) for 2-3 hours at room temperature. After a centrifugation step of 45 min. at 15000 rpm, the supernatant was incubated over night with TALON® Metal Affinity at 4° C. After an extensive wash of the resin, proteins were eluted with 50 mM Imidazole buffer and the fractions containing the MSP1-p19 protein were precipitated with 1 M ammonium sulphate during one night at 4° C. After a centrifugation step at 3000 rpm for 15 min., the supernatant as submitted to a second purification step, on a HITRAP™ Octyl SEPHAROSE® FF column (AMERSHAM PHARMACIA BIOTECH198 ) with an AKTA™ purifier system (AMERSHAM PHARMACIA BIOTECH™). The sample was applied in 20 mM tris HCl, pH8 containing 1M ammonium sulphate and eluted with a linear gradient from 0 to 100% of 0.05% TRITON® X-100 and 20 mM Tris Hcl pH8 in 30% propanol-1 performed at a flow rate of 1.5 ml/min.

N-Terminal Sequencing Analysis and Mass Spectrometry

Purified proteins were resolved by 4-12% NUPAGE® gels (INVITROGENE®), transferred to a polyvinylidene difluoride (PVDF) membrane, and sequenced using the Edman degradation method. Soluble protein samples (pf19) were analysed by matrix-assisted laser desorption ionization-time of flight (MALDI-TOF) mass spectrometry using Sinapinic acid matrix. The measurements were carried out on a VOYAGER-DE™ STR spectrometer (APPLIED BIOSYSTEMS™ Inc., Framingham, USA) equipped with a nitrogen laser (337 nm).

Antibodies and Immune Serum

The monoclonal antibody G17-12, which is specific for a conformational epitope of PfMSP1p19 [11] was obtained after intraperitoneal immunization of BALB/c mice with Sf9 cells infected with a recombinant baculovirus coding for PfMSP1p19. Fluorescein isothiocyanate (FITC)-conjugated goat anti-mouse IgG (IMMUNOTECH™) and goat anti-mouse and anti-human IgG (H+L) alkaline phosphatase conjugated antibodies (PROMEGA™). The irrelevant antibodies used as control in the cytometric assays were mouse anti-SV40 ones purchased by CALBIOCHEM®.

The hyperimmune human serum used for immunoblots, from an individual donor living in Libreville (Gabon), was kindly provided by Odile Puijalon.

Electrophoresis and Western Blot Analysis

Samples were analysed on 4-12% acrylamide NUPAGE® gels (INVITROGEN®), under reducing (with DDT, for Coomassie blue staining) or non-reducing (without DDT, for western blotting) conditions. Protein bands were visualised by Coomassie Blue staining or electrophoretically transferred to nitrocellulose (Schleicher & Schuell). After transfer, blots were blocked with 5% milk powder in Tris-buffered saline (TBS) for 30 min. at room temperature (RT) and incubated for 1 h at RT in 50 µg/ml of MAb G17-12 diluted in TBS. Blots were then washed 3 times for 10 min. in 5% milk in TBS, and incubated 1 h at RT with goat anti mouse alkalin phosphatase conjugated antibodies (PROMEGA™) diluted 1:7500 in TBS. After washes in TBS, antibody binding was detected with the ProtoBlot NBT/BCIP Color Development System (PROMEGA™).

Same procedure was applied for western blots using human hyperimmune serum as the primary antibodies diluted at 1:200 and revealed by goat anti-human alkalin phosphatase conjugated antibodies (PROMEGA™) diluted 1:7500 in TBS.

Confocal Microscopy

Infected Sf9 or H5 cells expressing either the anchored or the secreted form of MSP1-p19 were harvested 1, 2 or 3 days post infection. After washing with culture medium and 5% FCS (Foetal Cow Serum) the cells were incubated in 50 µg/ml of MAb G17-12 and 0,01% Na-azide for 45 min. at 4° C. Cells were then washed 2 times and incubated for 45 min. at 4° C. in the dark with goat-anti mouse FITC conjugated antibodies diluted 1:7500 with TBS. After three washes, cell pellets were suspended in 15 µl of Mowiol and cover-slips mounted on glass slides for an incubation of 3 hours in the dark at 4° C. The confocal analysis of the localisation of MSP1-p19 was then performed with a ZEISS™ LSM-510 ™ microscope and optical sections were performed at 0.5 µm increment. The three-dimensional reconstitutions were carried out using the LSM-510 ™ software.

Flow Cytometry

About $5.10^6$ infected HF or Sf9 cells expressing either pf19 or pf19+A were harvested 1, 2 or 3 days after infection and washed in culture medium with 5% FCS. Cells were then incubated in 50 µg/ml of MAb G17-12 or anti-SV40 mAb (control) and 0.01% Na-azide for 45 min. at 4° C. and washed twice in medium with FCS as above. After an incubation of 45 min. at 4° C. in the dark with goat anti-mouse FITC conjugated antibodies diluted 1:7500 with TBS, cells were washed 3 times in medium with FCS, and the pellets were resuspended in 1 ml of PBS with 1 µg/ml propidium iodide (SIGMA™). Surface MSP1-p19 levels of each cell samples were then monitored on a FACScan analyser (BECKTON DICKINSON™, Abingdon, Oxford, U.K.).

PI-PLC Treatment of Cells

About $5.10^6$ infected cells expressing the protein of pf19+A were washed in PBS and incubated for 1 hour at 37° C. with 0.3 unit of PI-PLC (Phosphatidylinositol phospholipase C., SIGMA™) in 300 µl of PBS. Cells were then washed twice in culture medium with FCS, and stained for flow cytometric analysis as described in the above section. Controls were performed in the same way but without addition of the PI-PLC.

Inositol and Monosaccharide Analysis

Prior to the GC-MS analysis, salts and detergents were removed by TCA/cold acetone precipitation. The pellet was resuspended in water and the protein amount was estimated by the BCA™ protein Assay (PIERCE™), using Bovine serum albumine as standard. Inositol residue was identified and quantified by GC-MS according to Fergusson et al. [41]. Monosaccharide was analysed by GC-MS after methanolysis, re-N-acetylation and trimethylsilylation according to Kemerling et al. [42].

GC-MS was performed on a CARLO ERBA™ 8000 Top GC apparatus coupled to a FINNIGAN™ Automass II mas spectrometer, using a capillary column (30 mm*0.25 mm) filled with EC-1 (ALLTECH®), gas vector: helium, 2 ml/min., column temperature for Inositol analysis: 40 to 150° C. at 15° C./min., 150° C. to 200° C. at 10° C./min., 200° C. to 240° C. at 5° C./min. and 240° C. for 7 min. Column temperature for monosaccharide analysis: 40 to 100° C. at 15° C./min., 100° C. to 200° C. at 7° C./min., 200° C. to 240° C. at 15° C./min. and 240° C. for 10 min. Electron ionization (E1) spectra were recorded using an ionization energy of 70 CV and an ionization current of 0.2 mA.

1-2-Results

Expression and Purification of the Membrane Bound and Secreted form of Recombinant MSP1-p19 Proteins Expression and Purification HF and Sf9 cells were infected with the corresponding recombinant virus and MSP1-p19 was produced and purified both as anchored and secreted forms from cell detergent extract and culture medium, respectively. Several detergents were used in order to optimize the solubilization of the recombinant anchored protein and thus the octyl β-glucoside appeared to be the more appropriate one, as previously observed for other proteins anchored to the cell membrane via a GPI moiety, either for insect cells [43] or other cell species [44]; [45]. The purification of the secreted protein form is achieved with the chromatographic metallo-affinity, while, for the cell surface form, an additional octyl RP-FPLC purification step was needed. The yield of purified protein was evaluated at 3.2 mg/liter of culture medium (around $1.6\ 10^9$ cells) and 11.2 mg/I for pf19+A and pf19, respectively.

N-Terminal Sequencing and Mass Spectrometry Analysis

N-terminal sequence analysis showed that, after purification, only pfMSP1-19 derived sequences are detected, either for Pf19+A or Pf19 preparations. For Pf19+A, results obtained have revealed the presence of at least 2 forms of recombinant MSP1-p19, i.e., 90% with VTH and 10% with MKI at N-terminal ends (see FIG. 2). The first one is a processing form of the protein which could be located at the cell surface but also in the endoplasmic reticulum, and the second one, which retains the signal peptide sequence, is apparently not processed and remains intracellular. This result is likely due to the fact that protein extraction was done on whole cells and that infected cells may have difficulty in processing an excess of recombinant proteins. When the 2 predominant protein bands (20 and 25 KD, see FIG. 3) were analysed separately, we showed that both of them are processed with 100% of protein containing the sequence VTH at the N-terminal end. Concerning the secreted form of the protein, Pf19. N-terminal sequencing showed that there is only the VTH sequence at the N-terminal end, implicating that all recombinant purified proteins are processed and lost their signal peptide.

MALDI-TOF mass spectrometry performed on the purified Pf19 protein preparations showed one major ion at m/z=16016 and several minor ions including m/z=17054, 17204, 17403 and 17606. The main ion corresponded to non-glycosylated soluble PfMSP1p19 with a VTHES N-terminus. The ion mass increases of 1038, 1184, 1387 and 1590 were in agreement with the detected presence of glycosylated structures, as described below.

Electrophoresis and Western Blot Analysis

The MAb G17-12 used is specific for PfMSP1-19 as it didn't recognize baculovirus-recombinant PvMSP1-19 of *P. vivax*, while MAb F10-3 specific to PvMSP1-p19 did not react with Pf19+A or Pf19-A (data not shown). Culture supernatants of the secreted form of Pf19 protein exhibited protein bands in electrophoresis after immunoblotting under non reducing conditions, while no reactive band was observed for culture supernatant of pf19+A infected cells. On the contrary, both cells lysates reacted with MAb G17-12 (data not shown).

As shown in FIG. 3, the electrophoretic mobility of the purified proteins was lightly greater under non-reducing conditions (FIG. 3B, 3C) than in reducing conditions (FIG. 3A). This result is expected since the products are very rich in cystein and probably have a more compact conformation under the non-reduced conditions. Under reducing conditions, purified proteins from the Pf19+A infected SF9 or HF cells exhibited two major bands migrating at 20 and 25 KD, at a higher apparent molecular mass than for the secreted form Pf19 (2 protein bands of around 18-22 KD) (FIG. 3A). Results obtained after Western immunoblotting in non-reduced conditions suggested that all these protein bands correspond to MSP1-p19 and that higher molecular weight bands correspond to MSP1-19 aggregated forms (FIG. 3B, 3C). The reactivity with monoclonal antibodies or immune serum was considerably decreased by disulphide reduction, indicating the predominance of non-linear epitopes (not shown). Western blots performed with human hyperimmune serum showed that both proteins (anchored and secreted forms) are recognised by naturally occurring antibodies (FIG.

3C). This is strong evidence that the conformation of the recombinant proteins is closely related to that of the native MSP1-19.

MSP1-p19 Recombinant Protein can be Expressed as a GPI-Anchored Form at the Surface of Insect Cells.

Fluorescent Microscopy

HF and Sf9 cells expressing the pf19+A form of the protein exhibited clearly surface fluorescence either by confocal microscopy (FIG. 4) or IFA (Data not shown) analysis being performed with the monoclonal G17-12 antibody. No surface fluorescent signal was recovered for the cells expressing the pf19 secreted protein form, either in Sf9 or HF cells. As shown in FIG. 4, the Pf19+A protein seemed to be expressed in a "ponctiform" manner at the surface of the cells, especially in HF cells, while the expression appeared to be more homogenous for the Sf9 cells.

Flow Cytometric Analysis

Figure 5A:
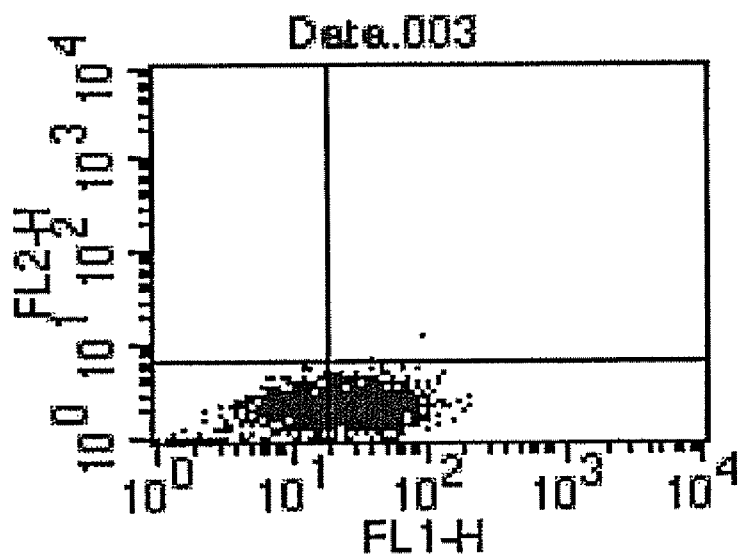
FIG. 5. Flow cytometry analysis of the surface expression of of pf19+A (A) and Pf19 (B) on live sf9 cells infected for 48 h with recombinant baculovirus pfsig19hisext+A and pfsig19hisext, respectively, and first gated for low propidium iodide staining. The Same result was recovered for HF cells.
Figure 5B:
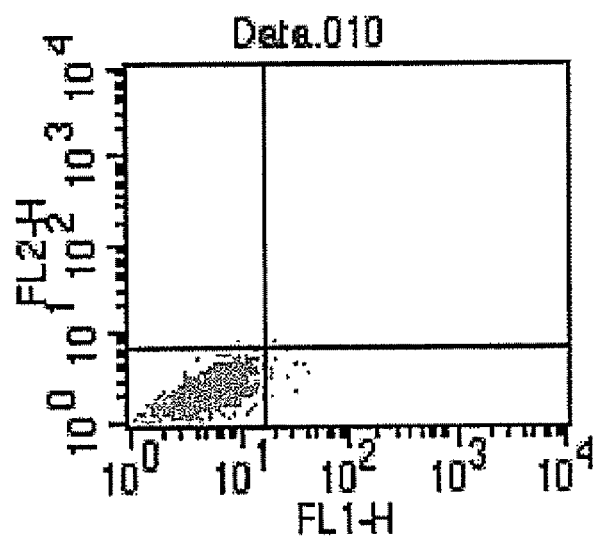

Flow cytometric analysis was carried out on live cells since dead cells absorb non specifically either the antibodies or proteins present in the medium. Thus, cells were then gated for low propidium iodide before analysis. A surface fluorescent signal was detected for cells expressing the Pf19+A protein, whereas no signal was detected for the cells expressing the secreted protein Pf19 (FIG. 5).

Figure 6A:
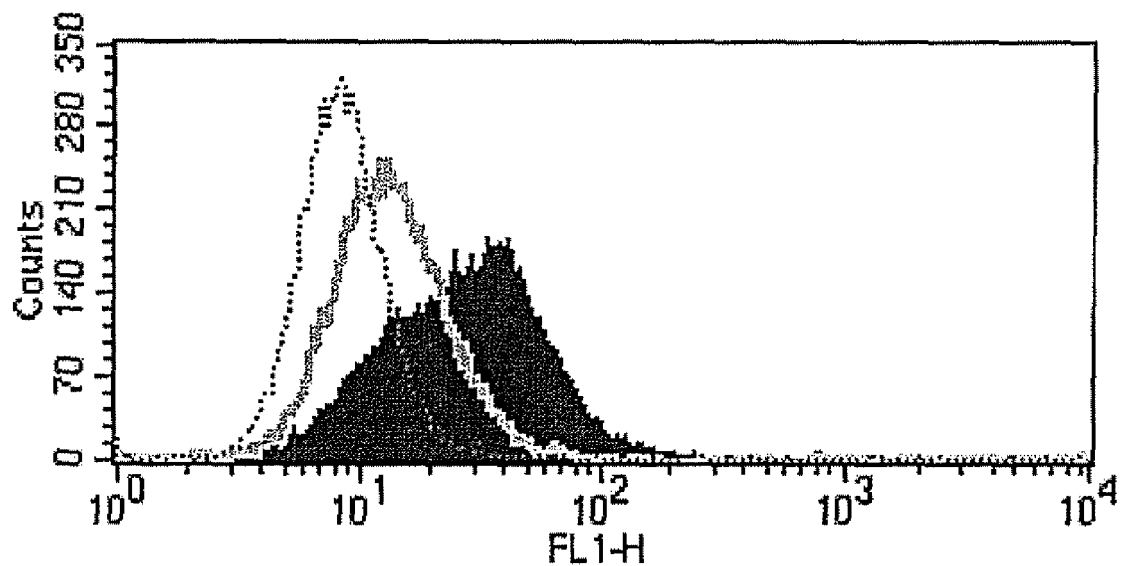
FIG. 6. Flow cytometry analysis of surface level of MSP1-p19 on sf9 cells (A) and HF cells (B) infected with recombinant baculovirus pfsig19hisext+A for 48 h. Expression of Pf19+A was evaluated with the monoclonal antibodies G17-12 with (thin curve) and without (filled area) treatment by PIPLC. The broken curve represents negative control with a primary irrelevant antibody.
Figure 6B:
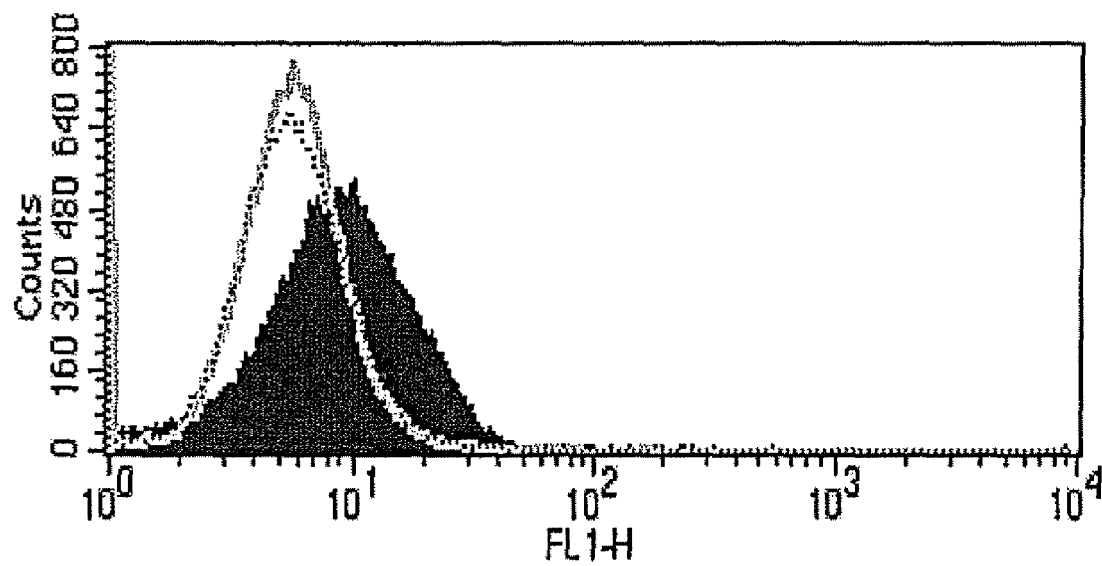

Recombinant full length C-terminal MSP1, MSP1-p19, produced in insect cells/baculovirus system was designed to be attached to the cell membrane via a GPI anchor. To verify this, the intact infected Sf9 and HF cells were incubated with a PI-Phospholipase C, a phospholipase, which specifically hydrolyses the GPI link and thus releases GPI-anchored protein from the cell surface. Cell surface staining was then checked by flow cytometric analysis using the G17-12 antibody. After 48 h of infection. PI-PLC treatment of the pf19+A expressing cells leads to a decrease of the Sf9 cells surface staining (FIG. 6A) and to a complete elimination of the surface protein for HF cells (FIG. 6B). This result confirms the surface localisation of the recombinant protein and demonstrates that at least a part of it is anchored to the insect's cell membrane via a GPI anchor.

Inositol and Carbohydrates Analysis

The PfMSP1p19 construct contains two potential N-glycosylation sites, at N162IS and N107PT. Monosaccharide analysis revealed the presence of N-acetyl glucosamine (GlcNAc), mannose (Man) and fucose (Fuc) in the purified soluble PfMSP1p19 preparations, which are characteristic of insect cell N-glycosylation patterns. However, since N-glycosylation has never been demonstrated to occur with a proline in the second position, it was) assumed that in this construct only the NIS site is used, which is consistent with the N-terminal sequencing and mass spectrometry data.

N-glycosylated entities were identified by MALDI-TOF mass spectrometric analyses of lyophilized samples, and resulted in the various ions described above. In particular, minor ions including m/z=17054, 17204, 17403 and 17606 were in agreement with the detected presence of glycan structures containing N-acetylhexosmaine, hexose and deoxyhexose in the following ratios respectively of 2:3:1, 2:3:2, 3:3:2 and 4:3:2. The presence of two additional minor ions at m/z=16222 and 16430 was also consistent with 1 and 2 N-acetylhexosamines added to the core PfMSP1p19 polypeptide. These could correspond to glycans with a LacNAc unit composed of N-acetylglucosamine and +/−N-acetylglucosamine previously detected in recombinant proteins expressed in T. ni cells [43]. Although no galactosylated N-glycans were detected here, the corresponding ion at m/z=16430 is very low intensity, and could be below the detection limit. Concerning the PfMSP1p19+A construct, quantitative monosaccharide analysis revealed the presence of 3% sugar in the protein preparation, including fucose, mannose and N-acetylglucosamine residues in the respective molar ratio of 0.5:3:1.5. Taking into account the 16 kDa molecular mass of the PfMSP1p19+A protein, these data suggested that half of the PsMSP1p19+A preparation is non N-glycosylated and half carries one N-glycan similar to the soluble recombinant form.

The amount of inositol was also quantified by GC-MS analysis, that showed the presence of 0.15 µg of inositol per 100 µg of protein. Since the mass of MSP1-19 was estimated at 16 kDa, no more than 14% of protein contained one inositol residue, indicating that only a small part of the MSP1-19 membrane bound preparation contains a GPI.

1-3-Discussion

1) Production and Purification

The production and purification procedure of both proteins is relatively rapid, scalable and generate a high amount of proteins. The cells infection conditions described above were found optimal for soluble as well as for membrane bound proteins. Two days of infection were needed in order to obtain high amount of secreted protein, while longer infection time leaded to degradation of the protein. One metallo-affinity chromatography appeared to be sufficient for obtaining a high purity of the protein as proved by the N-terminal sequencing and mass spectrometry analysis. Concerning the membrane bound protein, cytometric analysis have showed that 3 days of infection were required for optimization of the production (Data not shown). This protein was better solubilized under octyl glucoside than TRITON® X-100 detergent (data not shown). According to Hooper and Turner, this finding suggests the presence of a GPI membrane anchor [46]. Such hypothesis was also supported by TRITON® X-114 phase partition studies as the pf19+A protein was recovered in the detergent phase, and the secreted form of the protein was located in the aqueous fraction (Data not shown). Such result suggested that the C-terminal alone is responsible for partition into the detergent phase, which is consistent with the presence of a GPI anchor [47]. Following purification by metallo-affinity, the precipitation step eliminated most of the contaminants and octyl SEPHAROSE® Chromatography permitted to isolate two protein forms of MSP1-19 in 2-3 ml fraction.

At the final step of the purification. N-terminal sequencing showed effectively that there is only MSP1-19 in both preparations and the amount of produced anchored and secreted proteins was 2 µg/$10^6$ cells and 7 µg/$10^6$ cells, respectively. Then, baculovirus infected cells are able to produce 3,5-fold more secreted recombinant protein than anchored one. This indicates that processing of the GPI signal peptide and/or attachment of the protein to the cell membrane limited the production of the protein in the baculovirus system. Such a result is not surprising because the GPI biosynthesis pathway is a multi-step process involving many biochemical reactions [48]. In addition, the N-terminal analysis revealed the presence of a 10% proportion of the protein, which retained the signal peptide at the N-terminal end. Moreover, no more than 14% of the membrane bound form contained a GPI-anchor and we can deduce from such results that around 70% of the purified protein is retained in the endoplasmic reticulum, without the peptide signal sequence, but with the sequence coding for the GPI attachment. This is not such surprising result as the protein was extracted from whole cells and that some protein is necessarily present in an intra cellular unprocessed or processed (but without the addition of the GPI) forms. The facts that insect cells were boosted in order to produce a lot of protein in a non-physiological manner and that by the late stage of baculovirus infection, some enzymes involved in glycosylation are reduced in activity [49], probably explain the great proportion of such intracellular protein forms. Proteins must be effectively correctly folded before they can exit the endoplasmic reticulum and incorrect folded proteins are retained as it was already described concerning GPI-proteins [50]. However, the final amount of purified protein is higher than previously reported for other anchored proteins expressed in the baculovirus system such as CD59: 0.75-1 µg/$10^6$ cells [51] or p97: 0,18 µg/$10^6$ cells [52].

Immunoblot on cell lysates revealed that a significant proportion of the secreted form of the protein (Pfl9) was also retained inside the cells (not shown). This could be due to a deletion in the secretory peptide signal sequence, or inefficient recognition of the signal or to a "staking" effect due to a limited secretory capacity of the cell. However, purification procedure permits to obtain only processed protein and with yields that generally varied from 20-30 mg/L in High Five insect cells.

2) Western Blot Analysis

The western blot analysis performed either with the monoclonal antibodies or the human immune serum revealed that both proteins retained conformational epitopes closely related to those present on the parasite MSP1-p19 protein occurring in natural setting. However, the results also suggested that the recognition by antibodies, either with the monoclonal antibody or the human serum, was better with the anchored form of the protein than with the secreted one. For some authors, this reduced reactivity without the GPI can come from the fact that the addition of the GPI anchor to the polypeptide within the endoplasmic reticulum is important for the conformation of their protein [53]. But we can not exclude a difference between the two proteins due to other post-transductional modifications or due to their presentation to the secondary antibodies on the transfert membrane and the following binding.

3) Electrophoresis Analysis

Electrophoresis analysis showed a lightly reduced mobility for the anchored one rather than the secreted one, probably due to the presence of the transmembrane part of the protein. The MAb G17 detected the presence of multimeric forms of the purified proteins. Such aggregation form of the protein may be facilitated by the presence of the hydrophobic C-terminal part (either the sequence coding for the GPI and the GPI itself) in the anchored form of MSP1-19.

Secreted protein present mainly 2 major protein bands. No difference in peptide sequence has been observed. MALDI-TOF analysis and carbohydrate detection (Mannose, glucose, Fucose) suggested the presence of an N-glycan probably linked to Asn position (see FIG. 1B). The presence of N-glycans can explain the double band of soluble MSP1-19 with a glycosyled higher molecular weight band and a non-glycosyled lower molecular weight one.

Concerning the anchored form, several hypothesis have been proposed to explain the presence of two protein bands in addition to aggregated protein forms: differences in glycosylations as for pf19, or differences in processing or GPI-anchoring between both molecular species.

Indeed, the PfMSP1p19 products expressed in insect cells appear to be partially mofified post-transcriptionally with typical insect N-glycan entities [64]. These probably account for the difference in SDS-PAGE migration of the different bands seen for soluble PfMSP1p19, which otherwise appear to have identical polypeptide contents. The two "monomer" SDS-PAGE bands for the PfMSP1p19+A products are more difficult to define due to proable variability of N-glycan content, coupled with the presence of two very different C-termini with either a GPI structure or hydrophobic amino acids. Interestingly, in insect cell glycoproteins, the proximal N-acetylglucosamine residue can be fucosylated at position 6, as in mammalian cells, but also at position 3 (a1,3-fucosylation) which is relatively ubiquitous in plants and insects, but absent in mammalian glycoproteins. This feature renders the corresponding glycoproteins immunogenic in mammals [65], and therefore could be of potential interest for baculovirus recombinant proteins designed to function as human vaccine candidates.

4) Baculovirus/Insect Cells System

It is now well admitted that the baculovirus/insect cells system represent a system of choice for the expression of recombinant proteins in their native conformation. In addition, there are several examples of GPI-anchored recombinant proteins that can be expressed at insect cells surface in a functionally active form as it as been shown for recombinant GPI-B7-1, a human protein [43] and a GPI-recombinant form of the human protein CD59 [51].

Concerning MSP1, recombinant MSP1 proteins expressed respectively in yeast [20]; [22]; [23]; [67] or in *E. coli* [20]; [21]; [22] have shown a highly inconsistent or generally poor protective efficacy in primates, with one possible exception [66]. Moreover, ELISA studies conduced with a recombinant PfMSP1p19 protein produced in *S. cerevisiae* or *E. coli* [68] have shown that the corresponding PfMSP1p19 specific antibodies did not correlate with protection against high levels of parasitemia. Concerning the GPI anchored form of MSP1, a synthetic gene was constructed with a markedly reduced A+T content but, when expressed in mammalian cells or *E. coli*, it was not transported to the cell surface [54]. As well, when MSP1 gene was expressed from a recombinant vaccinia virus, the amount of MSP1 found on the surface of the HeLa cells was very low [55]. There is now some clear evidences that membrane-bound proteins are not well transported to the cell surface in transformed mammalian cells [56]. Even when the protein MSP1 was expressed in mammalian cell with a synthetic DNA construct encoding human sequence for N-terminal signal and C-terminal recognition/attachment signal for the GPI-anchor, only a very small amount of the recombinant protein was present on the surface of the cells [57].

However, it will be important, in the future, to evaluate if the presence of N-glycosylations has an impact or not on biological properties of the proteins. Such a finding was effectively mentioned in the mammalian expression system, where the recombinant MSP1 protein presents a high level of N-Glycosylations [57], that is not the case in the native protein and which could potentially interfere with the immunogenicity of the protein.

5) GPI Group

Recombinant MSP1-19 expressed at the cell surface of infected Sf9 and HF insect cells was cleaved with PI-Phospholipase C (PI-PLC), showed that the protein was correctly attached via a GPI-anchor, as intented in the experimental design. However, no more than 14% of membrane bound MSP1-19 contains an Inositol residue indicating that the main part of recombinant protein is not transferred to a GPI-anchor and stay in the cell. Such a result can be easily explain by the fact that the infection by the baculovirus kill the insect cells, which become rapidly not able to synthesised the GPI as proposed by Kedees [58]. Theses authors used two constructions for MSP1: one corresponding to the intact C-terminal MSP1 fragment, modified by addition of a signal sequence for secretion, and one similar but in which translation of the GPI-cleavage/attachment site was abolished by insertion of a stop codon into the DNA. When expressed in insect cells, both proteins could only be detected intracellularly, indicating a lack of secretion as well as transport to the cell surface. As no GPI could be detected, contrary to our results, they concluded that the baculovirus system does not seem to be the system of choice if expression in a native and GPI-anchored form is desired.

Our results show that, especially with Sf9 cells, PI-Phospholipase C do not cleave all the GPI-protein present at the surface of the insect cells. It is possible that these proteins are differentially processed in the two insect cell lines. For example, Hegedus et al. showed that Sf9 cell lines are able to express recombinant p97 protein that is GPI-anchored to the cell membrane, while Dipteran cell lines are not able to [59]. Some previous studies realized with insect cells expressing human recombinant protein have already reported that about 60% or 80% of cell surface proteins were cleaved after PIPLC treatment [51]; [43], that can be due to inaccessibility of the anchor [51] or the presence of a PIPLC-resistant form of GPI anchor with some additional acyl groups [60].

It is noteworthy that native MSP1 could not be cleaved from the parasite surface because of the presence of a fatty acid on the inositol ring [1]. Thus, GPI synthesised by the insect cells differs in their structure from those synthesised by the parasite; and it will be essential to evaluate how this recombinant protein can mimic the native one in in vivo conditions.

Example 2

Immunogenicity Studies with GPI-anchored and Secreted Form of *Plasmodium falciparum* MSP1-p19, Produced in the Baculovirus Expression System, GPI Acting as an Adjuvant 2-1-Materials and Methods Cells, Constructions, Generation and Purification of Recombinant Proteins

*Trichoplusia ni* (High Five, H5) and *Spodoptera frugiperda* (SF9) insect cells (INVITROGEN®) grown either in monolayer or in suspension cultures were cultured at 27° C. in INSECT X-PRESS™ medium (BIOWHITTAKER®) supplemented with 4 mM glutamine (GIBCO®-BRL) or SF-900™ (GIBCO®-BRL), respectively. The amplification of recombinant virus was done in Sf9 cells and proteins expression was done in HF cells.

The MSPI-p19 constructs used to express the secreted (pf19) and the anchored form (pf19+A) of the protein were generated as described previously (example 1) and contain sequences derived from *P. falciparum* (Uganda Palo-Alto isolate) sequence and a His-Tag used for the purification step. Both sequences are identical except that the one coding for the anchored form pf19+A i.e., the construct PfMSP1p19/His/GPI, includes the glycosylphosphatidylinositol (GPI) anchor signal at the C terminal end, after the His-tag.

For the protein expression, around $1.6 \cdot 10^6$ HF cells/ml were infected with recombinant virus ($10^8$ pfu/ml; moi=10) and allowed to grow in suspension cultures, at 27° C., in Insect X-Press medium (BIOWHITTAKER®) in the presence of gentamycine, and for 2 and 3 days for pf19 and pf19+A, respectively.

The purification protocol has already been described (example 1). Briefly, the secreted form of MSP1-p19 was purified from culture supernatants, dialysed against 20 mM Tris-HCl, pH8/500 mM NaCl, by a passage over a 1 ml HITRAP™ chelating HP column (AMERSHAM PHARMACIA BIOTECH™) charged with $CoCl_2$ 0.1M and elution with a linear gradient from 0 to 100% of 200 mM imidazole in 20 mM Tris-HCl, pH8/300 mM NaCl, on an AKTA™ purifier system (AMERSHAM PHARMACIA BIOTECH™). For the membrane bound form of MSP1-p19, purification was performed following two protocols, leading to two different immunisation trials. In each case, protein was purified in the presence of protease inhibitors (Complete EDTA-free, Roche) from the infected insect cells harvested from the culture. After solubilisation in octyl β-glucopyranoside, two purification steps were performed, one on a TALON® metal affinity resin (CLONTECH™, Palo Alto, Calif.) and a second, after precipitation of the contaminants in 1 M ammonium sulphate, on a HITRAP™ Octyl Sepharose FF column ( AMERSHAM PHARMACIA BIOTECH™) on a AKTA™ purifier system (AMERSHAM PHARMACIA BIOTECH™). The sample was applied in 20 mM Tris HCl, pH8 containing 1 M ammonium sulphate and eluted with a linear gradient from 0 to 100% of 0.05% Triton X-100 and 20 mM Tris HCl pH8 in 30% propanol-1. For the first immunisation trial (exp. 1), an additional final step of purification was performed on TALON® Metal Affinity Resin as described above and eluted with 50 mM imidazole in 0,05% TRITON® X100/20 mM Tris HCl pH8/100 mM NaCl. For the second immunisation trial (exp. 2), the protein was already purified after the second purification step on the HITRAP™ Octyl SEPHAROSE® FF column and eluted at 50% of the elution buffer described above. Protein purity of each sample was checked by Coomassie blue staining 4-12% acrylamide NUPAGE® gels (INVITROGEN®). N-terminal and mass spectrometry analysis.

Experimental Animals and Subcutaneous Immunization Trials

Six-eight weeks old female NMRI outbred mice were obtained from Janvier (Le Genest-St-isle, France). Proteins were concentrated on AMICON ULTRA™ (MILLIPORE™) before used in injections assays. Twenty μg of anchored MSP1-p19 (pf19+A) or secreted MSP1-p19 (pf19) were injected subcutaneously in two mouse abdomen sites. Sera from immunized animals were prepared from 100-200 μl whole blood samples drawn via the tail vein.

Two immunization protocols were performed. The first (exp.1) consisted on 5 mice injected with pf19 and 5 mice with pf19+A obtained with the first purification protocol (see above). Both protein were injected in 6.4 mM Tris HCl pH8, 32 mM NaCl, 0,016% TRITON® X-100, 16 mM imidazole. Injections were performed in the presence of MONTANIDE™ ISA 51 adjuvant (SEPPIC. France) in weight: Volume proportion. Five bleeds were performed at Day 0, Day 33, Day 110, Day 167 and Day 222, 33 days after a boost practised at Day 189 under the same protocol as the first injection. In other to evaluate the impact of TRITON® and imidazole on the immune response, 3 additional immunization protocol were performed in the presence of MONTANIDE™ ISA51: 5 mice were injected with pf19 in PBS, 5 mice with pf19 in PBS/0.016% TRITON® and 5 mice with pf19 in PBS/16 mM imidazole. Two bleeds were then performed at Day 0 and Day 33 after injections.

For the second protocol (exp. 2), both proteins were injected in conditions obtained with the second purification protocol for pf19+A and final concentrations of 5 mM Tris HCl pH8, 0.006% TRITON® X-100. Five mice were injected with pf19 and 5 with pf19+A in the presence of MONTANIDE™ ISA 51. In parallel, five mice were injected with pf19 and 5 with pf19+A in the presence of PBS (Phosphate Buffer Saline), without any adjuvant. Four bleeds were performed at days 0, 33, 70 and day 104, 33 days after a boost practised at day 71.

ELISA

The presence of specific antibodies against purified secreted MSP1-P19 antigen as well as total levels of immunoglobulins in mouse serum samples was determined by enzyme-linked immunosorbent assay (ELISA).

Anti-MSP1-p19 Ig. 96-well microtiter plates (Immunoplate Maxisorp, Nunc) were coated with 0.025 µg/well of purified secreted MSP1-p19 in PBS, overnight at 4° C., and saturated with 100 µl/well 0.5% gelatine (SIGMA™) in PBS for 1 h. Wells were then incubated with serial dilution (starting at 1:1000 dilution for IgG. IgG1 and IgG2b detection and 1:100 dilution for IgG2a. IgG3 and IgM detection) of sera from immunized mice diluted in 0.5 gelatine/0.1% TWEEN® 20 (MERCK®)/PBS for 1 h30. In order to evaluate the concentration of specific anti-MSP1 IgG2a antibodies in mg/ml, we used a mouse monoclonal anti-MSP1 IgG2a antibody name G17-12 as a standard. G17-12 hybridoma was obtained from BALB/c mice immunised with insect Sf9 cells expressing the recombinant protein MSP1-p19. G17-12 was applied at 750 ng/ml for the first dilution, and mice serum applied at serial dilutions starting at 1:100 dilution, as primary antibodies. Bound Igs were detected by the addition of a 1:6000 dilution of HRP-conjugated goat anti-mouse isotype-specific IgG and IgM-specific (SOUTHERN BIOTECHNOLOGY ASSOCIATES™ Inc. (SBA), Birmingham, Alabama) or 1:7000 dilution of HRP-conjugated goat anti-murine IgG (SBA) in 0.5% gelatine/0.1% Tween 20/PBS for 1 h. After washing, reactions were revealed adding 100 µl/well of 0.4 mg/ml o-Phenylenediamine (OPD) (SIGMA™) in 0.05 M phosphate-citrate buffer pH5 and 0.1% $H_2O_2$. After a 10 min. incubation step, the reaction was blocked with 50 µl 3 N HCl and absorbance was determined spectrophotometrically at wavelengths of 490/650 nm using a microplate reader (MOLECULAR DEVICES™). Titers were arbitrary defined as the maximum serum dilution used to detect a minimum O.D. of 0.5.

Total immunoglobulin in the sera. 96-well microtiter plates were coated overnight at 4° C. with 0.375 µg/well of goat anti-mouse Ig (SBA). As above, and after saturation, mice immunized serum were diluted and added at serial dilution starting at 1:1000 for 1 h30. Purified mouse IgG isotypes and IgM (SBA) were also applied at 0.75 µg/ml for the first dilution and used as standard and antibody detection was then carried out as described above.

2-2-Results 1) Both Proteins are Highly Immunogenic

Figure 10A:
FIG. 10A-C ELISA for total antibodies in mice sera. Mice were immunized either with anchored form of MSP1-19 (pf19+A, black bars) or secreted form of MSP1-9 (pf19, white bars) diluted in 6.1 mM Tris pH8, 32 mM Nacl, 0.016% TRITON® X100, 16 mM imidazole and in the presence of MONTANIDE™ ISA 51. Concentrations in mg/ml of total IgG, each IgG isotype and IgM antibodies were evaluated at days 0 (A) before the immunization, 167 days (B) after the immunization, and at day 222, 33 days after a boost (C). Bars indicate standard deviation from five tested mice.
Figure 10B:
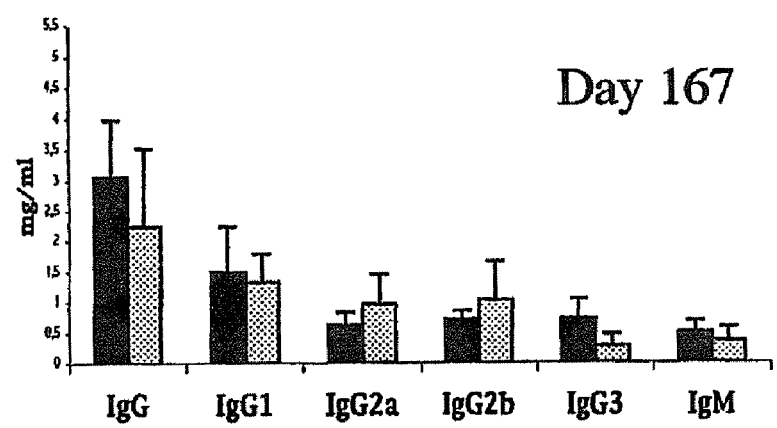

No systemic or local reactions were detected after any of the immunization assays, indicating that all antigens as well as the adjuvant are well tolerated by the mice. The minor differences detected between individual mice could be attributed firstly, to the fact that they are out-bred mice and secondly to variations in age as they arrived at the laboratory between 6 and 8 weeks old. However, no difference in level was detected between groups injected with pf19 or pf19+A, in both trial 1 or 2 and for each IgG isotypes and IgM. Non-specific antibodies detection. At day 0, in all groups, mice had more IgG than IgM, and less represented IgG isotype was IgG3 (Mean of all groups for both experiments: 0.046 mg/ml (n=30, range: 0.011-0.103)) when IgG2b (Mean of all groups for both experiments: 0.41 mg/ml (n=30, range: 0.163-0.955)) was the most represented one. Concentrations of total antibodies of each mouse detected before and 167 days after immunizations in the first trial are presented in FIG. 10A-C and in Table 3A.

TABLE 3

Evaluation of the immune response generated after immunisation with the anchored (GPI-MSP1-19) or the secreted (MSP1-19) form of MSP1-19: ratio of total serum antibodies induced in:
(A) vaccine trial 1: 167 days after the injection and 33 days after a second injection performed on day 189 (day 222) of each protein diluted in 6.4 mM Tris pH 8, 32 mM Nacl, 0.016% TRITON® X-100, 16 mM imidazole and in the presence of MONTANIDE™ ISA 51.
(B) vaccine trial 2: 33 days after the injection of each protein diluted in 5 mM Tris pH 8, 0.006% TRITON® X-100, in the presence (MONTANIDE™ ISA 51) or in the absence (PBS) of adjuvant. Each result corresponds to the mean of 5 mice.

A

| | GPI-MSP1-19 | | MSP1-19 | | ratio | ratio |
|---|---|---|---|---|---|---|
| | ratio D167/D0 | ratio D222/D0 | ratio D167/D0 | ratio D222/D0 | GPI-MSP1-19/ MSP1-19 Day 167* | GPI-MSP1-19/ MSP1-19 Day 222** |
| IgG | 6.1 | 9.7 | 3.0 | 7.3 | 2.0 | 1.3 |
| IgG1 | 7.9 | 12.3 | 4.8 | 8.2 | 1.6 | 1.5 |
| IgG2a | 7.5 | 14.0 | 7.9 | 8.3 | 1.0 | 1.7 |
| IgG2b | 3.5 | 6.3 | 3.3 | 6.9 | 1.0 | 0.9 |
| IgG3 | 12.9 | 8.1 | 5.8 | 4.8 | 2.2 | 1.7 |
| IgM | 3.8 | 3.5 | 3.6 | 5.0 | 1.1 | 0.7 |

*ratio GPI-MSP1-19/MSP1-19 Day 167 = (ratio D167/D0)GPI-MSP1-19/(ratio D167/D0)MSP1-19
**ratio GPI-MSP1-19/MSP1-19 Day 222 = (ratio D222/D0)GPI-MSP1-19/(ratio D222/D0)MSP1-19

B

| | MONTANIDE™ ISA 51 | | | PBS | | |
|---|---|---|---|---|---|---|
| | ratio GPI-MSP1-19 D33/D0 | ratio MSP1-19 D33/D0 | ratio GPI-MSP1-19/ MSP1-19* | ratio GPI-MSP1-19 D33/D0 | ratio MSP1-19 D33/D0 | ratio GPI-MSP1-19/ MSP1-19* |
| IgG | 2.3 | 2.1 | 1.1 | 1.6 | 1.6 | 1 |
| IgG1 | 5.2 | 3.3 | 1.6 | 1.9 | 1.1 | 1.7 |
| IgG2a | 1.5 | 3.0 | 0.5 | 5.6 | 2.3 | 2.4 |
| IgG2b | 1.5 | 1.5 | 1.0 | 1.3 | 1.6 | 0.8 |
| IgG3 | 3.3 | 7.2 | 0.5 | 4.0 | 3.4 | 1.2 |
| IgM | 2.1 | 2.6 | 0.8 | 1.9 | 1.4 | 1.3 |

*ratio GPI-MSP1-19/MSP1-19 = (ratio D33/D0)GPI-MSP1-19/(ratio D33/D0)MSP1-19

Figure 10C:
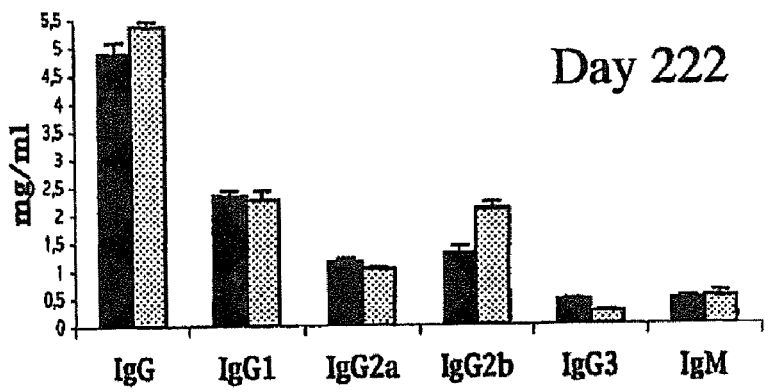

Immunizations with both proteins lead to an increase of all antibody subclass level, with the largest proportion of antibodies being of the IgG1 isotype (mean of 1.51 mg/ml and 1.33 mg/ml for pf19+A and pf19, respectively). The increase of the total IgG corresponded to 6-fold and 3-fold for pf19+A and pf19, respectively, and, in each group, the highest increase concerned the G3 (13-fold rises) for pf19+A and the IgG2a (8 fold rises) for pf19 (Table 3). The same general isotype profile was recovered before and 33 days after the boost, at day 222 (FIG. 10C, Table 3A). At this date, the induction of total IgG antibodies was around 2 times higher than at Day 167 for both proteins with the exception of IgG3. Looking at IgM levels, a slight increase was detected for the secreted protein and and a slight decrease for the anchored one.

Figure 11A:
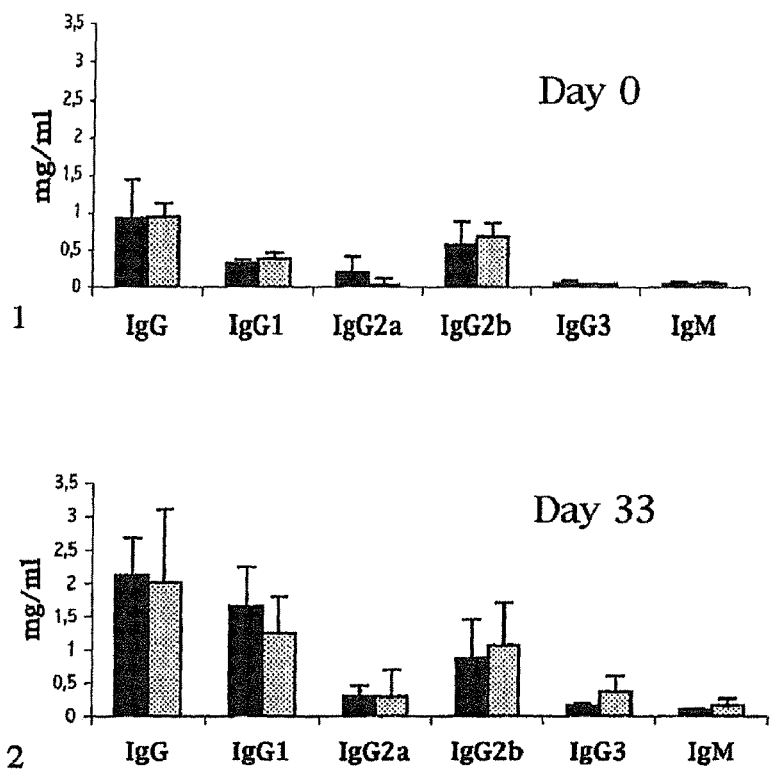
FIG. 11A-B ELISA for total antibodies in mice sera. Mice were immunized either with anchored form of MSP1-19 (pf19+A, black bars) or secreted form of MSP1-19 (pf19, white bars) diluted in 5 mM Tris pH8, 0.006% TRITON® X-100 and in the presence of MONTANIDE™ ISA 51(A) or in PBS without any adjuvant (B). Concentrations in mg/ml of total IgG, each IgG isotype and IgM antibodies were evaluated at days 0 (A1, B1) before the immunization and 33 days (A2, B2) after the immunization. Bars indicate standard deviation from five tested mice.

FIG. 11A and Table 3B show that, in trial 2, all IgG isotypes increased 33 days after immunisation with pf19+A or pf19 in the presence of MONTANIDE™, and that if global antibody levels were less than those detected at Day 167 in the first trial, they were in agreement with the previously seen domination of the IgG1 isotype (mean of 1.65 mg/ml and 1.25 mg/ml for pf19+A and pf19, respectively). The increase of the total IgG corresponded to more than 2-fold for both proteins, and IgG1 displayed the highest increase (5.2-fold rises) for pf19+A while it was IgG3 (7.2-fold rises) for pf19. This last result has to be considered carefully because such an significant IgG3 increase for the secreted protein came from one mouse among the 5 tested, which had a very high IgG3 titer at day 33. In addition, the high increase concerning the IgG2a was essentially due to the fact that 3 mice out of 5 had no detectable IgG2a antibodies at day 0 in this group.

Figure 11B:
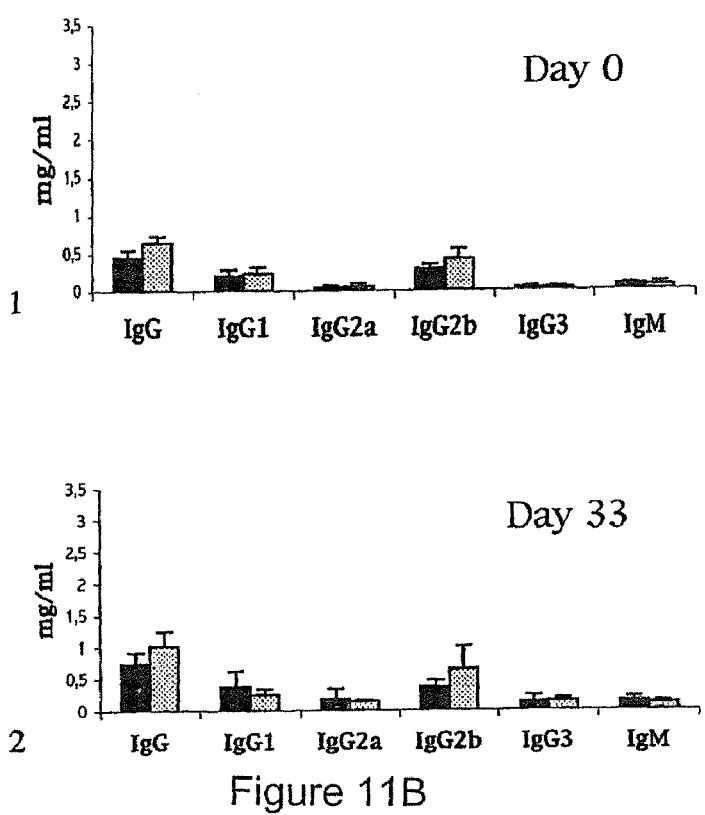

Immunisation with protein without adjuvant induced IgG responses, which exhibited same isotype profile as observed with MONTANIDE™ and showing that the proteins themselves were capable to generate a general immune response. The increase in IgG was 1.4 and 1.3 times weaker than after immunisation in the presence of the adjuvant for pf19+A and pf19, respectively. The highest increase concerned the IgG2a for pf19+A followed by IgG3 isotypes for both proteins (FIG. 11B, Table 3B).

Specific antibodies detection. Previous experiments have shown that injection of only MONTANIDE™ ISA51 without antigen did not induced any anti-MSP1-p19 antibodies (Data not shown). As expected, no mice had any anti-MSP1-p19 antibodies at the beginning of each trial (J0), before the injection of the antigens.

Figure 12:
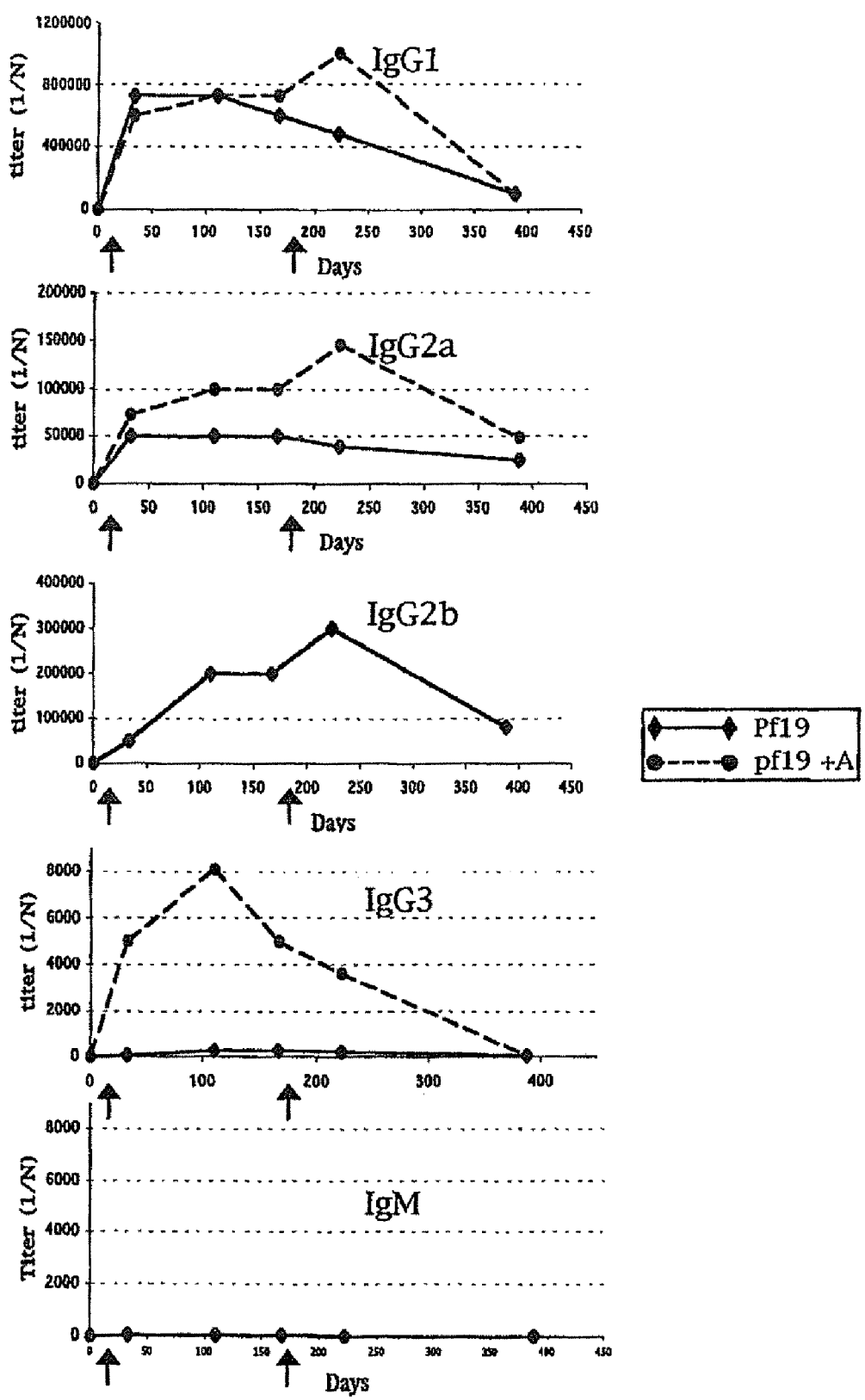
FIG. 12 Course of the anti-MSP1-19 antibodies titer in mice sera. Mice were immunized (↑) either with anchored form of MSP1-19 (pf19+A, broken curve) or secreted form MSP1-19 (pf19, thin curve) diluted in 6.4 mM Tris pH8, 32 mM Nacl, 0.016% TRITON® X-100, 16 mM imidazole and in the presence of MONTANIDE™ ISA 51. Absorbance corresponding to titers of each IgG isotype and IgM antibodies were evaluated at days 33, 110, 167 after the immunization, and at day 222 and 388, respectively 33 and 166 days after a second injection performed at day 189. Data are shown as mean of titer of each group (n=5) estimated as the highest dilution for a minimum absorbance of 0.5.

Concerning the trial 1, a single s.c. injection of 20 µg of pf19 or pf19+A induced high titers of serum anti-MSP1 antibodies, which were maintained at a steady level until Day 167 (FIG. 12). Even if it is difficult to compare the titers of each antibody class and subclasses because of potential misinterpretation that may result from widely different affinities of the secondary antibodies, we can estimate, with the first serum dilution used (1:1000), that the anti-MSP1-P19 response seemed to be essentially of the IgG1 types for each protein (estimated maximum titer 33 day days after a boost: 1/1000000). Concerning the IgG2a and IgG2b, the interpretation is difficult because of the cross-reactivity that exists between the two subclasses, but IgG2b seems to be the second most representative subclass (first dilution serum used: 1:1000 and estimated maximum titer 1/145000). Anti-MSP1 IgM antibodies were near the lowest level that could be detected in any serum and at any of the bleeds, which is a normal thing at day 33 post-injection. The same isotype subclass profile was recovered at days 33, 110, 167, as well as after a second injection. This boost led to an increase in the level of all IgG isotype antibodies specific to MSP1-P19 except IgG3.

Figure 14A:
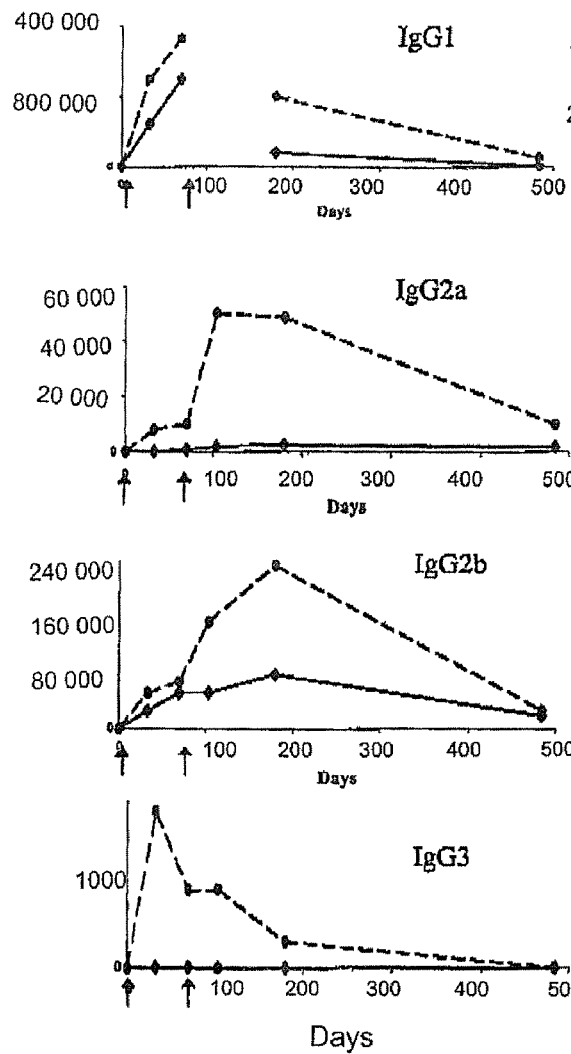
FIG. 14A-B: Anti-MSP1p19 antibody titers in mice sera. Mice were injected twice (↑) on days 0 and 71 with 20 ug of anchored (MSP1p19-GPI, dashed line) or secreted MP1p19 (solid line) diluted in 5 mM Tris pH8, 0.006% TRITON® X-100 formulated with MONTANIDE™ ISA 51(A) or PBS (B). Titers for IgG isotypes were determined 33 and 70 days after the first injection, and at days 104 and 180, respectively 33 and 109 days after the second injection. No IgM was recovered at any bleed of the trial. Data are shown as mean of titer of each group (n=5) at the highest dilution for a minimum absorbance of 0.5.
Figure 14B:
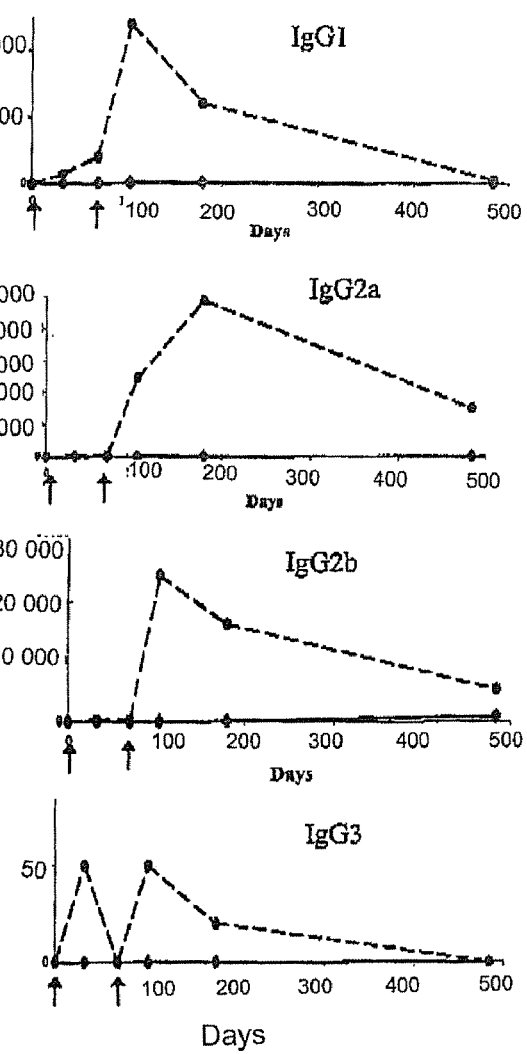

Data obtained from trial 2 confirmed the induction of a strong IgG anti-MSP1-P19 response until 70 days after the immunisation with pf19+A or pf19 in the presence of MONTANIDE™, and a predominance of the IgG1 subclass (FIG. 13A and 14A), though slightly less rapid than observed in trial 1 but of the same intensity at day 70 (estimated tier: 1/730000). When each protein was injected without adjuvant a specific, while weak, anti-MSP1-p19 response was only detected with pf19+A (also predominantly of the IgG1 type with estimated titer of 8000 at day 70 after only one injection) (FIG. 13B and 14B).

TABLE 4

|  |  | GPI-MSP1-19 | | | MSP1-19 | | | ratio | |
| --- | --- | --- | --- | --- | --- | --- | --- | --- | --- |
|  |  | anti-MSP1-19 IgG2a mg/ml | total IgG2a mg/ml | ratio %* | anti-MSP1-19 IgG2a mg/ml | total IgG2a mg/ml | ratio %* | ratio GPI-MSP1-19/ MSP1-19 | GPI-MSP1-19/ ratio MSP1-19* |
| Trial 1 | D0 | 0 | 0.08 | 0 | 0 | 0.12 | 0 | | |
|  | D167 | 0.088 | 0.62 | 16.3 | 0.037 | 0.97 | 4.3 | 2.4 | 3.8 |
|  | D222 | 0.221 | 1.15 | 20.45 | 0.049 | 1.02 | 5.4 | 4.5 | 3.8 |
| Trial 2 | D0 | 0 | 0.2 | 0 | 0 | 0.05 | 0 | | |
|  | D33 | 0.019 | 0.3 | 19 | 0.003 | 0.151 | 2.3 | 6.3 | 8.3 |

*relative proportion of specific antibodies among total induced antibodies for each antigen As summarised in Table 4, MSP1-P19 specific IgG2a were absent in all mice at Day 0. At Day 167 of the first trial, quantification of IgG2a revealed that 16.3% of the IgG2a produced after immunization with pf19+A and 4.3% of IgG2a produced after immunization with pf19 were some anti-MSP1-P19-IgG2a. Result obtained after the second injection show a 2.5-fold and 1.3-fold rises in anti-MSP1-P19 IgG2a between Day 167 and 33 days after boosting for pf19+A and pf19, respectively. The percentage of IgG2a antibodies specific to MSP1-P19 among total ones increased after boosting to 20.45% and 5.4% for pf19+A and pf19, respectively, confirming the specific action of the antigen. During the trial 2 with MONTANIDE™, the percentage of anti-MSP1-P19-IgG2a among total induced IgG2a, was almost identical with 19% for pf19+A and 2.3% for pf19. Such results indicated that both proteins generated a polyclonal response in addition to a specific one, at least as far as this isotype is concerned. It is noteworthy that, since only non-specific IgM was detected, a degree of general immune stimulation has occurred, indicating a possible additional stimulation by antigens present in the animal laboratory environment. However, it is also important to specify here that we evaluated only antibodies against MSP1-P19 as we have coated the secreted form of the protein and that the possible antibodies against the C-terminal part of the anchored form were not taken into account.

2) Effect of GPI on the Immune Response

Non-specific antibodies detection. When comparing the level of total IgG 167 days after an immunisation with Pf19+A or with Pf19 in the presence of MONTANIDE™ (trial 1), we showed that levels are augmented 2-fold in the presence of the GPI form of the protein. This increase is 2.2-fold and 1.6-fold higher for the IgG3 and IgG1, respectively, and is comparable for the IgG2a, IgG2b and IgM antibodies (FIG. 10A-C. Table 3A). After a second injection, comparable isotype profiles were recovered except a difference that emerges for the IgG2a antibodies, with a 1.7-fold higher induction with Pf19+A than with Pf19.

This general IgG subclasses repartition was not completely recovered 33 days after immunizations performed with the adjuvant in the trial 2 (FIG. 11A, Table 3B). The induction of IgG1 antibodies remained 1.6 times higher with ph19+A than with pf19. After the IgG1, IgG3 remained the highest increase for the anchored protein (3.4-fold rises) but, for this isotype as well as for IgG2a and IgM, we found a higher increase with pf19 but with the restriction discussed above.

Immunisation of each protein in the absence of adjuvant showed that if no difference was detected concerning the increase of total IgG, a higher level of increase of IgG1 (1.7-fold rises) and IgG2a (2.4-fold rises) was detected with pf19+A (FIG. 11B, Table 3B) while an almost equivalent level was detected concerning the other isotypes.

Specific antibodies detection. Concerning the anti-MSP1-P19 antibodies, immunization with pf19+A in the presence of MONTANIDE™ leads to higher titers of IgG3 and IgG2a than with pf19, 33, 110, 167 days after the injection (trial 1 and 2), as well as 33 days after the second injection in the trial 1. Titers were almost similar concerning the IgG1 and IgG2b between the two proteins with only slight higher titers with pf19+A (FIG. 12, 13A and 14A). Injection of both proteins without adjuvant showed that 33 days later, some IgG1, IgG2a, IgG2b and, in a lesser extent. IgG3 are detected with pf19+A when no antibodies could be detected for pf19 even with a serum dilution of 1:100 FIG. 13B and 14B).

While no difference was detected between the two proteins concerning the total IgG2a antibodies after one injection (see Table 3), results obtained with the use of Mab G17-12 as standard (Table 4) have confirmed that, concerning the anti-MSP1-P19 IgG2a, 2.4-fold more antibodies were produced after injection with pf19+A as compared to pf19 at day 167 of the trial 1. After the second injection, this difference increased with 4.5-fold more IgG2a concerning pf19+A. In addition, the proportion of specific anti-MSP1-P19 IgG2a antibodies among the total induced IgG2a antibodies was 3.8 times higher after pf19+A injection (either one or two) than after pf19 injection. Concerning the second trial in the presence of adjuvant, we found 6 and 5-fold more anti-MSP1-P19 IgG2a antibodies 33 and 70 days, respectively after injection with pf19+A than with pf19, and 8.3-fold more specific IgG2a among total induced ones with pf19+A than with pf19. In the absence of adjuvant, no IgG2a were detectable for pf19 while, for pf19+A, 20-fold less IgG2a were detectable 70 days after the injection (0.002 mg/ml) by comparison with the injection performed in the presence of ISA 51.

Importantly, there was no observed toxicity associated with the PfMSP1p19-GPI antigen over the course of the experiment (i.e., more than 1 year).

4) Imidazole and TRITON® Effect

To determine whether the imidazole or the TRITON® used during the trial 1 played a role in the induction of the high antibodies titers or isotypes obtained, we performed 3 series of mice immunisation with the secreted form of MSP1-p19 in the presence of adjuvant MONTANIDE™, with 16 mM imidazole, 0,016% TRITON® or PBS only. Concerning the non-specific response the ratios between antibody concentrations estimated at Day 33 on those detected on day 0 were equivalent with each formulation, indicating that there is no impact of TRITON® or imidazole on the non specific immune response (Data not shown). No anti-MSP1-P19 antibodies were detected at Day O. Thirty-three days after the immunisation, no specific IgM were detected and all IgG MSP1-P19 specific antibodies detected showed equivalent titres for each group (data not shown). Therefore, no influence of imidazole or TRITON® was detected on the immune response against MSP1-P19, when used in the concentrations of the first trial.

3-3-Discussion

Two series of vaccination trials were performed in order to determine the immunogenicity of baculovirus recombinant protein MSP1-p19 produced in order to obtain 2 forms of the protein: a GPI-anchored one and a secreted one. Expression and purification of such proteins have been already described (Bonnet, submitted). Constructions coding for each protein were similar except that the one designed to be GPI-anchored has the signal sequence coding for the GPI attachment at the C-terminal end. As expected, the absence of the GPI anchor sequence resulted in the failure of the protein to attach to the insect cell membrane and she was secreted in the culture medium, when the presence of such a structure permitted to obtain a membrane bound protein. We have showed that the insect expression system can add properly a GPI anchor to MSP1-P19 and that both form of the protein were recognized by antibodies present in human immune serum from endemic country, suggested that their conformation represents that of the native antigen MSP1-P19 (Bonnet, submitted).Both form, anchored (Pf19+A) and secreted (pf19), of the protein MSP1-p19 were highly immunogenic in mice and generate anti-MSP1-P19 antibody responses predominantly, but not exclusively, of the cytophilic IgG1 subclass. The use of a monoclonal antibody as a standard for anti-MSP1-IgG2a as well as the evaluation of the total antibodies in mice serum has permitted us to establish that both proteins induce specific as well as non-specific humoral responses. In adjuvant formulation, both proteins stimulate comparable proportions of specific IgG1, IgG2b and IgM. Some difference was observed concerning anti-MSP1-P19 IgG2a, with more antibodies induced by the GPI form of the protein. Finally, a greater and clear difference was recovered concerning the anti-MSP1-P19 IgG3 with a highest proportion of this isotype after an immunisation with Pf19+A than with pf19. These differences were reproducible between trials. Finally, we demonstrated that, in the absence of any adjuvant, pf19+A is capable to induce a specific immune response while pf19 does not.

1) Proteins Immunogenicity

It is interesting to note that on one hand, the antibody responses to both antigens are predominantly an IgG1 response, which represents classically a T-cell dependent response and, on the other hand, the both antigens stimulated also predominantly IgG2b, which corresponds usually to a T-cell independent response. Although similarities exist for many antigens within an antigen class, the several exceptions suggest that no single feature of antigen structure regulates isotype preference [69]. So it is clear that the categorization of antigens into subclasses of T-dependent or independent cells although operationally useful, implies special properties of the antigen and that some intermediate pattern such as those observed for MSP1-p19 exist. In addition, results indicated that both T-helper 1 (as indicated by the induction of IgG2a)

and T-helper 2 (as indicated by the induction of IgG1) subsets of T-helper cells were elicited by vaccination with both MSP1-P19 protein forms, which is considered as a primordial thing for an effective anti-malaria vaccine [70]; [71]. The fact that we observed a T-cell dependant response with recombinant MSP1-P19 from P. falciparum is in favour of the use of such part of the MSP1 protein as a malaria vaccine, which is not in agreement with previous studies claiming that immunodominant T-cell epitopes were found in sequences of the MSP1-33 region and not in the MSP1-P19 one [25]; [72]; [73].

The immune response obtained after immunisation with the two proteins exhibited very high specific antibody titres, which were maintained for more than 5 months with only one injection. Dosage of the total antibodies showed as well that the global immune response was increased more than 6-fold if we consider for example the total IgG generated 167 days after an injection with the GPI form of the protein. Although the production of antibodies recognizing MSP1-P19 epitopes does not represents the majority of antibodies induced by the secreted or the anchored form of the protein, we showed that, in trial 1 and at least concerning the IgG2a, from 16% (after one injection) to 20% (after two injections) of these antibodies were some specific ones after immunization with the anchored protein form, while theses percentages were only 4.3 to 5.4% with the secreted protein form.

Antibodies induced by both proteins were predominantly of the IgG1 type followed by IgG2b and IgG2a types. This isotype profile is similar to those observed by Dutta et al. after mice immunization with P. vivax MSP1-42 expressed in Escherichia coli [74]. The murine cytophilic IgG1 and IgG2a antibodies have been implicated in protection against murine malaria in several studies. Even, in 1978, green et al. demonstrated that the cytophilic immunoglobulin G1 was protective against P. berghei in rat. After that, in 1987, Falanga et al. showed that, in immunized mice, protected against a parasite challenge, the isotypic pattern showed that the IgG1 and IgM constituting the main part of the response [75]. Concerning IgG2a antibodies, it was also demonstrated that, in mice, they play dominant role in mediating immunity to P. yoeli [76], P. chabaudi [77]; [78] and P. berghei [79]. A recent study has confirmed such results and showed that, in mice, the sequential upregulated synthesis of IgG2a and IgG1, in that order, was associated with protective immunity against P. yoeli and P. chabaudi infections [80].

The use of adjuvant is a very important approach to enhancing the immunogenicity of vaccines and some new impressive adjuvants are urgently needed for human use. Our results shown that the MONTANIDE™ ISA 51, which is generally considered safe for human use, is a powerful immunostimulator, which can be envisaged for making single dose vaccines. This adjuvant is an oil and water emulsion and its formulation delays the degradation of the antigen and also provides controlled slow release of antigen, which probably participate in the high and long lasting immuno-stimulation reflected in our results.

2) Difference Between the Two Proteins (with and without Anchor Sequence)

Purified antigens are not usually strongly immunogenic on their own and require the addition of adjuvant. The injection of the both proteins forms without any adjuvant generated effectively a general immune response where around 1.5-time less total antibodies were detected than with the adjuvant. However, results showed that only the anchored form of the protein could induce a specific immune response without any adjuvant, even if this response was 20 time weaker than with the adjuvant as far as the anti-MSP1 IgG2a are concern.

Such a result represents a critical determinant for its use in vaccinology. These data suggest that the higher immune response detected with this protein has to be attributed to the protein and not to a different presentation of this antigen by the adjuvant. In addition, differences recovered after an immunization with the anchored form of the protein has to be attributed to the additional C-terminal part of the protein including GPI structures, as it is the only difference between the 2 recombinant proteins. To our knowledge, it is the first demonstration that a GPI structure can act itself as an adjuvant and can be used with antigens that carry their own covalent immunostimulator and/or immunomodulator. Our result showed effectively that GPI interacts with the immune system to enhance the immune response but as well to specifically modify the isotype of the response to the given antigen. It is possible that the two proteins stimulate the same subpopulations of B cells, essentially restricted to IgG1 and that the GPI form of the protein stimulate, in addition, a second subpopulation of B cells, restricted for example to IgG3 via the C terminal additional part of the protein corresponding to the glycolipidic GPI structure. It was effectively establish that anti-soluble protein or anti-carbohydrate antibodies are generally restricted to the IgG1 and IgG3, respectively [81]; [82]. As we have only 14% of GPI anchored protein in our pf19+A preparation (the other corresponding to non-processed protein either with the signal peptide or the sequence coding for the GPI attachment) it is possible that other forms of the protein present in this preparation were responsible of the resulting immune response by stimulating a panel of several subpopulations of B cells. This raises the possibility that antigens select IgG subclasses on the basis of selective interaction with B-cell receptors as suggested by [69]. It is noteworthy that in vitro study has showed that GPI-related glycoinositolphospholipids from Trypanosoma cruzi can induce both IgG3 and IgG1 production by murine B cells, in the absence of covalently linked proteins but with a requirement for cytokine costimulation [83].

GPI anchors from parasitic protozoa have been shown to exert a wide variety of effects on cells of the host innate immune system both by stimulating/regulating cells in a non-specific manner and by serving as targets for both specific T and B lymphocytes responses (review in [84]). However, the receptor(s) that are triggered by GPIs has not been identified and several proposition have been made. Joyce et al. have demonstrated that GPI anchors are the main natural ligand associated with mouse CD1d molecules [85] and Schofield at al. have demonstrated that NK cells were stimulated by GPIs in a CD1d-dependant manner [33]. However, such results were controversial and, in 2000, a study showed that, the absence of CD1d expression in knockout mice does not significantly influence the titers of IgGs directed against the GPI-anchored CS protein of P. berghei, and that B cell help is mediated through classical MHC class II/CD4+ T cell interaction [86]. Some studies have also demonstrated that GPI from Trypanosoma cruzi bind to CD1d but without eliciting dominant innate or adaptive immune response via this pathway [87], while previous ones reported that T. cruzi GPIs might stimulate NK T cell in a CD1d-restricted manner [88]. On the other hand. GPI of this protozoon have been implicated in the activation of Tool Like Receptor 2 (TLR-2) from both mouse and human origin, activation that lead to the initiation of the various macrophage functions induced by the GPIs [89]; [90]. Recently it was also demonstrated that the adjuvanticity of a TLR ligand, the Macrophage-activating lipopeptide-2 (MAP-2) from Mycoplasma fermentans, can be mediated, at least in part, by the stimulation of Dendritic cells maturation [91]. Consequently, TLR-ligands have been proposed as new possible vaccine adjuvants [92].

The questions if the insect-GPI generated adjuvant signal observed here implicates Toll like receptors or CD1d and the activation of macrophages as well as dendritic cells, is now open. In vivo immunisation of mice that lack CD1d or TLR with both recombinant MSP1-P19 protein forms should answer questions related to this pathway. The fact that these both receptors implicated in activation of the innate immunity are unrestricted emphasise the potential for GPIs as future constituents of vaccines. In fact, if GPIs are TLR or CD1d ligands, the low polymorphism detected for these receptors let us to envisage that GPIs could generate equal adjuvant signal for everyone without any HLA restriction. Naturally, a key feature for using insect-GPI as adjuvant will be its safety in human, which should first has to be tested in non human primates.

Our results showed that Pf19 and pf19+A antigens stimulated different patterns of response especially as far as the IgG2a was concerned, with 2.4 to 6.3-fold more IgG2a induced with the anchored MSP1-P19 form of the protein. Such IgG subclass is generally induced by viral infections [939 but also by parasite infections [79]; [94]. IgG2a activates the complement system more readily than do IgG1 antibodies [95] and are quite efficient mediators of antibody-dependant cell-mediated cytotoxicity [96]. They bond to specific receptors that are expressed on murine macrophages and are involved in phagocytosis [97]. It was demonstrated that such antibody subclass is elicited by interferon-gamma [98]; [99]. As previously mentioned, the fact that IgG2a have been implicated in the protection against murine malaria is a positive point concerning the use of a GPI-protein in vaccinology against malaria.

The GPI form of MSP1-P19 also induces significantly more total as well as specific IgG3 than the secreted form of the protein. Classically. IgG3 constitutes a very low fraction of IgG responses to T cell-dependent protein Ag [81]; [100]. It was demonstrated a long time ago that antigens can be categorized according to which of the four mice IgG subclasses is elicited and post-translational modification of proteins by lipids and carbohydrates are well known to influence the antigen presenting cell type and thus antibody subclass expression [81]; [102]; [93]. The specificity of IgG3 is directed primarily against carbohydrates, polysaccharides and repeating epitope Ags [81]; [103]. The IgG3, found in normal mouse serum in very low amounts, appear early in immune responses independently of T cell help and, as such, are early effector molecules of the immune system which can elicit powerful effector function like complement activation [81]; [103]. It has been shown that IgG3 antibodies are important in the resistance of pathogens like Streptococcus pneumoniae [104]; [105] or *Candida albicans* [106]. In 1998, Gavin et al. have identified the mouse IgG3 macrophage receptor as FcγRI, which was confirmed by recent data [107]; [108]. It was demonstrated that MO selectively up-regulated IgM to IgG3 class switching [109] and that NK cells, which area source of IL10, may play a role in mediating such humoral immunity [110].

3) Human Immunity

Human immunity to malaria is quite complex and still not completely understood but it now appears clear that humoral immune mechanisms may be very important in controlling the blood stages of the parasite. In this context of human malaria, the association between isotypes distribution and protective immunity remains controversial. However, it seems to emerge that Antibody-dependent protection against *P. falciparum* is primarily mediated by human cytophilic IgG antibodies (human IgG1 and IgG3), which activate cytotoxic and phagocytic effector functions of neutrophils and monocytes [111]; [112]; [113]; [114]; [115]. Thus, such a proposition correlates with the fact that murine cytophilic IgG1 and IgG2a antibodies are protective against malaria infection in mice, suggesting the necessity of a immune response implicating a Th1 as well as a Th2 response. In addition, Yount et al first demonstrated that polysaccharide but not protein antigens stimulated preferentially human IgG2 subclass [116] and this result was confirmed for a variety of polysaccharides [117]; [118]; [119]. The question if human IgG2 and mice IgG3 share a common ancestry have been raised as human IgG2 is the subclass associated with many anticarbohydrate variable regions and is the one supposed to be the most primitive of the human IgG subclasses [120]; [119]. However, during a fiels study performed in Papua New Guinea, Boutlis et al., have determined that the antibody response induced by *P. falciparum* GPIs is characterized predominantly by IgG3, with a lesser contribution from IgG1 and an absence of IgG2 and IgG4.

Conclusion

In conclusion, our study demonstrates that the baculovirus system is a powerful expression system for producing highly immunogenic recombinant malaria proteins and that GPI-posttranscriptional modification of these proteins are implicated in the resulting immune response. The question if it is possible or not to generate some anti-toxic antibodies against *P. falciparum* GPIs by vaccination with insect GPIs needs to be tested. However, to our point of view, this is not the most promising advantage of integrating an insect GPI anchor in a malaria vaccine. The question of whether the observed switching in antibody isotypes in the presence of the GPI is a good thing or not is now open and it would be also of great interest to test this antigen in monkey models in order to evaluated the protective effect of such elevated IgG3 and IgG2a antibodies.

Using the baculovirus/insect cell expression system, recombinant PfMSP1p19 was produced either as a soluble antigen, or as an insoluble membrane anchored form. The latter can be released from the infected insect cell surface by treatment with phosphatidyl-inositol phospholipase C (PI-PLC), which specifically cleaves GPI structures. By comparing the immunogenicity of the two forms of purified PfMSP1p19 in out-bred mice, the inventors have provided striking evidence that a covalent GPI structure can induce a dramatic increase in antibody titers of all isotypes in the absence of other adjuvants, compared to the same protein lacking this modification (FIGS. 14A-B). In conjunction with the MONTANIDE™ ISA 51 adjuvant (similar to IFA), the PfMSP1p19-GPI antigen mediates a surprisingly large increase in IgG1 and IgG3, compared to the soluble version (FIG. 14A-B). Importantly, there was no observed toxicity associated with the PfMSP1p19-GPI antigen over the course of the experiment (more than 1 year).

REFERENCES [NUMBER]

The following references correspond to those, for which the reference number is between brackets, i.e.: [number].

1. Gerold, P., et al., *Structural analysis of the glycosyl-phosphatidylinositol membrane anchor of the merozoite surface proteins-1 and -2 of Plasmodium falciparum*. Mol Biochem Parasitol, 1996. 75(2): p. 131-43.
2. Blackman, M. J., et al., *A single fragment of a malaria merozoite surface protein remains on the parasite during red cell invasion and is the target of invasion-inhibiting antibodies*. J Exp Med, 1990. 172(1): p. 379-82.

3. Holder, A. A. and M. J. Blackman, *What Is the Function of Msp-1 on the Malaria Merozoite. Parasitology Today*, 1994. 10(5): p. 182-184.
4. O'Donnell, R. A., et al., *Functional conservation of the malaria vaccine antigen MSP-1 19 across distantly related Plasmodium species*. Nat Med, 2000. 6(1): p. 91-5.
5. Hughes, M. K. and A. L. Hughes, *Natural selection on Plasmodium surface proteins*. Mol Biochem Parasitol, 1995. 71(1): p. 99-113.
6. Jongwutiwes, S., K. Tanabe, and H. Kanbara, *Sequence conservation in the C-terminal part of the precursor to the major merozoite surface proteins (MSP1) of Plasmodium falciparum from field isolates*. Mol Biochem Parasitol, 1993. 59(1): p. 95-100.
7. Kang, Y. and C. A. Long, *Sequence heterogeneity of the C-terminal, Cys-rich region of the merozoite surface protein-1 (MSP-1) in field samples of Plasmodium falciparum*. Mol Biochem Parasitol, 1995. 73(1-2): p. 103-10.
8. Kaneko, O., et al., *Plasmodium falciparum: allelic variation in the merozoite surface protein 1 gene in wild isolates from southern Vietnam*. Exp Parasitol, 1997. 86(1): p. 45-57.
9. Qari, S. H., et al., *Predicted and observed alleles of Plasmodium falciparum merozoite surface protein-1 (MSP-1), a potential malaria vaccine antigen*. Mol Biochem Parasitol, 1998. 92(2): p. 241-52.
10. Chitarra, V., et al., *The crystal structure of C-terminal merozoite surface protein 1 at 1.8 A resolution, a highly protective malaria vaccine candidate*. Mol Cell, 1999. 3(4): p. 457-64.
11. Pizarro, J. C., et al., *Crystal structure of a Fab complex formed with PfMSP1-19, the C-terminal fragment of merozoite surface protein 1 from Plasmodium falciparum: a malaria vaccine candidate*. J Mol Biol, 2003. 328(5): p. 1091-103.
12. Riley, E. M., et al., *Naturally acquired cellular and humoral immune responses to the major merozoite surface antigen (PfMSP1) of Plasmodium falciparum are associated with reduced malaria morbidity*. Parasite Immunol, 1992. 14(3): p. 321-37.
13. Egan, A. F., et al., *Clinical immunity to Plasmodium falciparum malaria is associated with serum antibodies to the 19-kDa C-terminal fragment of the merozoite surface antigen, PfMSP-1*. J Infect Dis, 1996. 173(3): p. 765-9.
14. Shi, Y. P., et al., *Natural immune response to the C-terminal 19-kilodalton domain of Plasmodium falciparum merozoite surface protein 1*. Infect Immun, 1996. 64(7): p. 2716-23.
15. Shai, S., M. J. Blackman, and A. A. Holder, *Epitopes in the 19 kDa fragment of the Plasmodium falciparum major merozoite surface protein-1 (PfMSP-1(19)) recognized by human antibodies*. Parasite Immunol, 1995. 17(5): p. 269-75.
16. Branch, O. H., et al., *A longitudinal investigation of IgG and IgM antibody responses to the merozoite surface protein-1 19-kiloDalton domain of Plasmodium falciparum in pregnant women and infants: associations with febrile illness, parasitemia, and anemia*. Am J Trap Med Hyg, 1998. 58(2): p. 211-9.
17. Perraut, R., et al., *Distinct surrogate markers for protection against Plasmodium falciparum infection and clinical malaria identified in a Senegalese community after radical drug cure*. J Infect Dis, 2003. 188(12): p. 1940-50.
18. Egan, A. F., et al., *Human antibodies to the 19 kDa C-terminal fragment of Plasmodium falciparum merozoite surface protein 1 inhibit parasite growth in vitro*. Parasite Immunol, 1999. 21(3): p. 133-9.
19. O'Donnell, R. A., et al., *Antibodies against merozoite surface protein (msp)-1(19) are a major component of the invasion-inhibitory response in individuals immune to malaria*. J Exp Med, 2001. 193(12): p. 1403-12.
20. Kumar, S., et al., *Immunogenicity and in vivo efficacy of recombinant Plasmodium falciparum merozoite surface protein-1 in Aotus monkeys*. Mol Med, 1995. 1(3): p. 325-32.
21. Burghaus, P. A., et al., *Immunization of Aotus nancymai with recombinant C terminus of Plasmodium falciparum merozoite surface protein 1 in liposomes and alum adjuvant does not induce protection against a challenge infection*. Infect Immun, 1996. 64(9): p. 3614-9.
22. Kumar, S., et al., *Immunogenicity and efficacy in aotus monkeys of four recombinant Plasmodium falciparum vaccines in multiple adjuvant formulations based on the 19-kilodalton C terminus of merozoite surface protein 1*. Infect Immun, 2000. 68(4): p. 2215-23.
23. Egan, A. F., M. J. Blackman, and D. C. Kaslow, *Vaccine efficacy of recombinant Plasmodium falciparum merozoite surface protein 1 in malaria-naive, -exposed, and/or -re-challenged Aotus vociferans monkeys*. Infect Immun, 2000. 68(3): p. 1418-27.
24. Stowers, A. W., et al., *Efficacy of Two Alternate Vaccines Based on Plasmodium falciparum Merozoite Surface Protein 1 in an Aotus Challenge Trial*. Infect Immun, 2001. 69(3): p. 1536-1546.
25. Chang, S. P., et al., *A recombinant Baculovirus 42-kilodalton c-terminal fragment of Plasmodium falciparum merozoite surface protein 1 protects Aotus monkeys against malaria*. Infection and Immunity, 1996. 64(1): p. 253-261.
26. Perera, K. L., et al., *Baculovirus merozoite surface protein 1 C-terminal recombinant antigens are highly protective in a natural primate model for human Plasmodium vivax malaria*. Infect Immun, 1998. 66(4): p. 1500-6.
27. Stowers, A. W., et al., *A recombinant vaccine expressed in the milk of transgenic mice protects Aotus monkeys from a lethal challenge with Plasmodium falciparum*. Proc Natl Acad Sci U S A, 2002. 99(1): p. 339-44.
28. Ferguson, M. A., et al., *Glycosyl-phosphatidylinositol molecules of the parasite and the host*. Parasitology, 1994. 108 Suppl: p. S45-54.
29. Schofield, L. and S. D. Tachado, *Regulation of host cell function by glycosylphosphatidylinositols of the parasitic protozoa*. Immunol Cell Biol, 1996a. 74(6): p. 555-63.
30. Schofield, L. and F. Hackett, *Signal transduction in host cells by a glycosylphosphatidylinositol toxin of malaria parasites*. J Exp Med, 1993. 177(1): p. 145-53.
31. Tachado, S. D., et al., *Glycosylphosphatidylinositol toxin of Plasmodium induces nitric oxide synthase expression in macrophages and vascular endothelial cells by a protein tyrosine kinase-dependent and protein kinase C-dependent signaling pathway*. J Immunol, 1996. 156(5): p. 1897-1907.
32. Schofield, L., et al., *Glycosylphosphatidylinositol toxin of Plasmodium up-regulates intercellular adhesion molecule-1, vascular cell adhesion molecule-1, and E-selectin expression in vascular endothelial cells and increases leukocyte and parasite cytoadherence via tyrosine kinase-dependent signal transduction*. J Immunol, 1996b. 156(5): p. 1886-96.
33. Schofield, L., et al., *CD1d-restricted immunoglobulin G formation to GPI-anchored antigens mediated by NKT cells*. Science, 1999. 283(5399): p. 225-9.
34. Naik, R. S., et al., *Glycosylphosphatidylinositol anchors of Plasmodium falciparum: molecular characterization* and naturally elicited antibody response that may provide immunity to malaria pathogenesis. J Exp Med, 2000b. 192(11): p. 1563-76.

35. de Souza, J. B., et al., *Prevalence and boosting of antibodies to Plasmodium falciparum glycosylphosphatidylinositols and evaluation of their association with protection from mild and severe clinical malaria.* Infect Immun, 2002. 70(9): p. 5045-51.

36. Boutlis, C. S., et al., *Antibodies to Plasmodium falciparum Glycosylphosphatidylinositols: Inverse Association with Tolerance of Parasitemia in Papua New Guinean Children and Adults.* Infect Immun, 2002. 70(9): p. 5052-5057.

37. Schofield, L., et al., *Synthetic GPI as a candidate antitoxic vaccine in a model of malaria.* Nature, 2002. 418 (6899): p. 785-9.

38. Longacre, S., K. N. Mendis, and P. H. David, *Plasmodium vivax merozoite surface protein 1 C-terminal recombinant proteins in baculovirus.* Mol Biochem Parasitol, 1994. 64(2): p. 191-205.

39. Chang, S. P., et al., *Plasmodium falciparum: gene structure and hydropathy profile of the major merozoite surface antigen (gp195) of the Uganda-Palo Alto isolate.* Exp Parasitol, 1988. 67(1): p. 1-11.

40. Summers, M. D. and G. E. Smith, *A manual of methods for baculovirus vectors and insect cells culture procedures.* Texas Agric. Exp. Station bull., 1987. 1555.

41. Fergusson, M. A. J., in *Lipid modification of proteins. A practical approach.*, A. J. Turner and N. M. Hooper, Editors. 1992, IRL press: Oxford. p. 191-230.

42. Kamerling, J. P., et al., *Characterization by gas-liquid chromatography-mass spectrometry and proton-magnetic-resonance spectroscopy of pertrimethylsilyl methyl glycosides obtained in the methanolysis of glycoproteins and glycopeptides.* Biochem J, 1975. 151(3): p. 491-5.

43. Nagarajan, S. and P. Selvaraj, *Expression and characterization of glycolipid-anchored B7-1 (CD80) from baculovirus-infected insect cells: protein transfer onto tumor cells.* Protein Expr Purif, 1999. 17(2): p. 273-81.

44. Brown, D. A. and J. K. Rose, *Sorting of GPI-anchored proteins to glycolipid-enriched membrane subdomains during transport to the apical cell surface.* Cell, 1992. 68(3): p. 533-44.

45. McHugh, R. S., et al., *Construction, purification, and functional incorporation on tumor cells of glycolipid-anchored human B7-1 (CD80).* Proc Natl Acad Sci U S A, 1995. 92(17): p. 8059-63.

46. Hooper, N. M. and A. J. Turner, *Ectoenzymes of the kidney microvillar membrane. Differential solubilization by detergents can predict a glycosyl-phosphatidylinositol membrane anchor.* Biochem J, 1988. 250(3): p. 865-9.

47. Hooper, N. M. and A. Bashir, *Glycosyl-phosphatidylinositol-anchored membrane proteins can be distinguished from transmembrane polypeptide-anchored proteins by differential solubilization and temperature-induced phase separation in Triton X-114.* Biochem J, 1991. 280 (Pt 3): p. 745-51.

48. Eisenhaber, B., et al., *Enzymes and auxiliary factors for GPI lipid anchor biosynthesis and post-translational transfer to proteins.* Bioessays, 2003. 25(4): p. 367-85.

49. van Die, I., et al., *Glycosylation in lepidopteran insect cells: identification of a beta 1->4-N-acetylgalactosaminyltransferase involved in the synthesis of complex-type oligosaccharide chains.* Glycobiology, 1996. 6(2): p. 157-64.

50. Delahunty, M. D., et al., *Uncleaved signals for glycosylphosphatidylinositol anchoring cause retention of precursor proteins in the endoplasmic reticulum.* J Biol Chem, 1993. 268(16): p. 12017-27.

51. Davies, A. and B. P. Morgan, *Expression of the glycosylphosphatidylinositol-linked complement-inhibiting protein CD59 antigen in insect cells using a baculovirus vector.* Biochem J, 1993. 295(Pt 3): p. 889-96.

52. Kennard, M. L., et al., *Expression of cell surface GPI-anchored human p97 in baculovirus infected insect cells.* Biotech. Bioeng., 1997. 55: p. 41-53.

53. Martinez, A. P., et al., *The roles of the glycosylphosphatidylinositol anchor on the production and immunogenicity of recombinant ookinete surface antigen Pbs21 of Plasmodium berghei when prepared in a baculovirus expression system.* Parasite Immunol, 2000. 22(10): p. 493-500.

54. Pan, W., et al., *Vaccine candidate MSP-1 from Plasmodium falciparum: a redesigned 4917 by polynucleotide enables synthesis and isolation of full-length protein from Escherichia coli and mammalian cells.* Nucleic Acids Res, 1999. 27(4): p. 1094-103.

55. Tine, J. A., et al., *NYVAC-Pf7: a poxvirus-vectored, multiantigen, multistage vaccine candidate for Plasmodium falciparum malaria.* Infect Immun, 1996. 64(9): p. 3833-44.

56. Moran, P. and I. W. Caras, *Requirements for glycosylphosphatidylinositol attachment are similar but not identical in mammalian cells and parasitic protozoa.* J Cell Biol, 1994. 125(2): p. 333-43.

57. Burghaus, P. A., et al., *Analysis of recombinant merozoite surface protein-1 of Plasmodium falciparum expressed in mammalian cells.* Mol Biochem Parasitol, 1999. 104(2): p. 171-83.

58. Kedees, M. H., et al., *Processing and localisation of a GPI-anchored Plasmodium falciparum surface protein expressed by the baculovirus system.* Eur J Cell Biol, 2000. 79(1): p. 52-61.

59. Hegedus, D. D., et al., *Differences in the expression and localization of human melanotransferrin in lepidopteran and dipteran insect cell lines.* Protein Expr Purif, 1999. 15(3): p. 296-307.

60. Roberts, W. L., et al., *Structural characterization of the glycoinositol phospholipid membrane anchor of human erythrocyte acetylcholinesterase by fast atom bombardment mass spectrometry.* J Biol Chem, 1988. 263(35): p. 18776-84.

61. Naik, R. S., E. A. Davidson, and D. C. Gowda, *Developmental stage-specific biosynthesis of glycosylphosphatidylinositol anchors in intraerythrocytic Plasmodium falciparum and its inhibition in a novel manner by mannosamine.* J Biol Chem, 2000a. 275(32): p. 24506-11

62. Gowda, D. C., *Structure and activity of glycosylphosphatidylinositol anchors of plasmodium falciparum.* Microbes and infection, 2002. 4: p.983-990.

63. Howell, S., et al., *A cleavable N-terminal signal peptide is not a prerequisite for the biosynthesis of glycosylphosphatidylinositol-anchored proteins.* J Biol Chem, 1994. 269(25): p. 16993-6.

64. Altmann, F. et al., *Insect cells as hosts for the expression of recombinant glycoproteins.* Glycoconj J 1999. 16(2): p.109-123.

65. Wilson, I. B. et al., *Core alpha 1,3-fucose is a key part of the epitope recognized by antibodies reacting against plant N-linked oligosaccharides and is present in a wide variety of plant extracts.* Glycobiology 1998. 8(7): p. 651-661.

66. Darko, C. A., Angov, E., Collins, W. E. et al. *The clinical-grade 42-kilodalton fragment of merozoite surface protein*

1 of Plasmodium falciparum strain FVO expressed in Escherichia coli protects Aotus nancymai against challenge with homologous erythrocytic-stage parasites. Infect Immun 2005;73(1): 287-297.
67. Stowers, A. W., Cioce, V., Shimp, R. L. et al. *Efficacy of two alternate vaccines based on plasmodium falciparum merozoite surface protein 1 in an Aotus challenge Trial.* Infect Immun 2001;69(3):1536-1546.
68. John, C. C., O'Donnell, R. A., Sumba, P. O. et al. *Evidence that invasion-inhibitory antibodies specific for the 19-kDa fragment of merozoite surface protein-1 (MSP-1)9) can play a protective role against blood-stage Plasmodium falciparum infection in individuals in a malaria endemic area of Africa.* J Immunol 2004; 173(1):666-672.
69. Slack, J., et al., *Subclass restriction of murine antibodies. II. The IgG plaque-forming cell response to thymus-independent type 1 and type 2 antigens in normal mice and mice expressing an X-linked immunodeficiency.* J Exp Med, 1980. 151(4): p. 853-62.
70. Taylor-Robinson, A. W., et al., *The role of TH1 and TH2 cells in a rodent malaria infection.* Science, 1993. 260 (5116): p. 1931-4.
71. Long, C. A., et al., *Immunity to erythrocytic stages of malarial parasites.* Am J Trop Med Hyg, 1994. 50(4 Suppl): p. 27-32.
72. Udhayakumar, V., et al., *Identification of T and B cell epitopes recognized by humans in the C-terminal 42-kDa domain of the Plasmodium falciparum merozoite surface protein (MSP)-1.* J Immunol, 1995. 154(11): p. 6022-30.
73. Egan, A., et al., *Characterization of human T- and B-cell epitopes in the C terminus of Plasmodium falciparum merozoite surface protein 1: evidence for poor T-cell recognition of polypeptides with numerous disulfide bonds.* Infect Immun, 1997. 65(8): p. 3024-31.
74. Dutta, S., et al., *Purification, characterization, and immunogenicity of a disulfide cross-linked Plasmodium vivax vaccine candidate antigen, merozoite surface protein 1, expressed in Escherichia coli.* Infect Immun, 2001. 69(9): p. 5464-70.
75. Falanga, P. B., et al., *Isotypic pattern of the polyclonal B cell response during primary infection by Plasmodium chabaudi and in immune-protected mice.* Eur J Immunol, 1987. 17(5): p. 599-603.
76. White, W. I., C. B. Evans, and D. W. Taylor, *Antimalarial antibodies of the immunoglobulin G2a isotype modulate parasitemias in mice infected with Plasmodium yoelii.* Infect Immun, 1991. 59(10): p. 3547-54.
77. Von der Weld, T., et al., *The immune response to Plasmodium chabaudi malaria in interleukin-4-deficient mice.* Eur J Immunol, 1994. 24(10): p. 2285-93.
78. Wunderlich, G., I. C. Moura, and H. A. del Portillo, *Genetic immunization of BALB/c mice with a plasmid bearing the gene coding for a hybrid merozoite surface protein 1-hepatitis B virus surface protein fusion protects mice against lethal Plasmodium chabaudi chabaudi PC1 infection.* Infect Immun, 2000. 68(10): p. 5839-45.
79. Waki, S., et al., *Interferon-gamma and the induction of protective IgG2a antibodies in non-lethal Plasmodium berghei infections of mice.* Parasite Immunol, 1995. 17(10): p. 503-8.
80. Smith, E. C. and A. W. Taylor-Robinson, *Parasite-specific immunoglobulin isotypes during lethal and non-lethal murine malaria infections.* Parasitol Res, 2003. 89(1): p. 26-33.
81. Perlmutter, R. M., et al., *Subclass restriction of murine anti-carbohydrate antibodies.* J Immunol, 1978. 121(2): p. 566-72.
82. Rosenberg, Y. J. and J. M. Chiller, *Ability of antigen-specific helper cells to effect a class-restricted increase in total Ig-secreting cells in spleens after immunization with the antigen.* J Exp Med, 1979. 150(3): p. 517-30.
83. Bento, C. A., et al., *Glycoinositolphospholipids purified from Trypanosoma cruzi stimulate Ig production in vitro.* J Immunol, 1996. 157(11): p. 4996-5001.
84. Ropert, C. and R. T. Gazzinelli, *Signaling of immune system cells by glycosylphosphatidylinositol (GPI) anchor and related structures derived from parasitic protozoa.* Curr Opin Microbiol, 2000. 3(4): p. 395-403.
85. Joyce, S., et al., *Natural ligand of mouse CD1d1: cellular glycosylphosphatidylinositol.* Science, 1998. 279(5356): p. 1541-4.
86. Molano, A., et al., *Cutting edge: the IgG response to the circumsporozoite protein is MHC class II-dependent and CD1d-independent: exploring the role of GPIs in NK T cell activation and antimalarial responses.* J Immunol, 2000. 164(10): p. 5005-9.
87. Procopio, D. O., et al., *Glycosylphosphatidylinositol-anchored mucin-like glycoproteins from Trypanosoma cruzi bind to CD1d but do not elicit dominant innate or adaptive immune responses via the CD1d/NKT cell pathway.* J Immunol, 2002. 169(7): p. 3926-33.
88. Duthie, M. S., et al., *During Trypanosoma cruzi infection CD1d-restricted NK T cells limit parasitemia and augment the antibody response to a glycophosphoinositol-modified surface protein.* Infect Immun, 2002. 70(1): p. 36-48.
89. Campos, M. A., et al., *Activation of Toll-like receptor-2 by glycosylphosphatidylinositol anchors from a protozoan parasite.* J Immunol, 2001. 167(1): p. 416-23.
90. Almeida, I. C. and R. T. Gazzinelli, *Proinflammatory activity of glycosylphosphatidylinositol anchors derived from Trypanosoma cruzi: structural and functional analyses.* J Leukoc Biol, 2001. 70(4): p. 467-77.
91. Link, C., et al., *The Toll-like receptor ligand MALP-2 stimulates dendritic cell maturation and modulates proteasome composition and activity.* Eur J Immunol, 2004. 34(3): p. 899-907.
92. Lien, E. and D. T. Golenbock, *Adjuvants and their signaling pathways: beyond TLRs.* Nat Immunol, 2003. 4(12): p. 1162-4.
93. Coutelier, J. P., et al., *IgG2a restriction of murine antibodies elicited by viral infections.* J Exp Med, 1987. 165 (1): p. 64-9.
94. Markine-Goriaynoff, D., et al., *IFN-gamma-independent IgG2a production in mice infected with viruses and parasites.* Int Immunol, 2000. 12(2): p. 223-30.
95. Klaus, G. G., et al., *Activation of mouse complement by different classes of mouse antibody.* Immunology, 1979. 38(4): p. 687-95.
96. Kipps, T. J., et al., *Importance of immunoglobulin isotype in human antibody-dependent, cell-mediated cytotoxicity directed by murine monoclonal antibodies.* J Exp Med, 1985. 161(1): p. 1-17.
97. Heusser, C. H., C. L. Anderson, and H. M. Grey, *Receptors for IgG: subclass specificity of receptors on different mouse cell types and the definition of two distinct receptors on a macrophage cell line.* J Exp Med, 1977. 145(5): p. 1316-27.
98. Snapper, C. M. and W. E. Paul, *Interferon-gamma and B cell stimulatory factor-1 reciprocally regulate Ig isotype production.* Science, 1987. 236(4804): p. 944-7.
99. Finkelman, F. D., et al., *IFN-gamma regulates the isotypes of Ig secreted during in vivo humoral immune responses.* J Immunol, 1988. 140(4): p. 1022-7.

100. Rubinstein, L. J. and K. E. Stein, *Murine immune response to the Neisseria meningitidis group C capsular polysaccharide. I. Ontogeny.* J Immunol, 1988. 141(12): p. 4352-6.

101. Grey, H. M., J. W. Hirst, and M. Cohn, *A new mouse immunoglobulin: IgG3.* J Exp Med, 1971. 133(2): p. 289-304.

102. Balkovic, E. S., J. A. Florack, and H. R. Six, *Immunoglobulin G subclass antibody responses of mice to influenza virus antigens given in different forms.* Antiviral Res, 1987. 8(3): p. 151-60.

103. Greenspan, N. S. and L. J. Cooper, *Intermolecular cooperativity: a clue to why mice have IgG3?* Immunol Today, 1992. 13(5): p. 164-8.

104. Briles, D. E., et al., *Mouse Igg3 antibodies are highly protective against infection with Streptococcus pneumoniae.* Nature, 1981. 294(5836): p. 88-90.

105. McLay, J., et al., *Gamma 3 gene-disrupted mice selectively deficient in the dominant IgG subclass made to bacterial polysaccharides. II. Increased susceptibility to fatal pneumococcal sepsis due to absence of anti-polysaccharide IgG3 is corrected by induction of anti-polysaccharide IgG1.* J Immunol, 2002. 168(7): p. 3437-43.

106. Han, Y., M. H. Riesselman, and J. E. Cutler, *Protection against candidiasis by an immunoglobulin G3 (IgG3) monoclonal antibody specific for the same mannotriose as an IgM protective antibody.* Infect Immun, 2000. 68(3): p. 1649-54.

107. Gavin, A. L., et al., *Identification of the mouse IgG3 receptor: implications for antibody effector function at the interface between innate and adaptive immunity.* J Immunol, 1998. 160(1): p. 20-3.

108. Barnes, N., et al., *FcgammaRI-deficient mice show multiple alterations to inflammatory and immune responses.* Immunity, 2002. 16(3): p. 379-89.

109. Shparago, N., et al., *IL-10 selectively regulates murine Ig isotype switching.* Int Immunol, 1996. 8(5): p. 781-90.

110. Snapper, C. M. and J. J. Mond, *A model for induction of T cell-independent humoral immunity in response to polysaccharide antigens.* J Immunol, 1996. 157(6): p. 2229-33.

111. Thelu, J., et al., *Development of natural immunity in Plasmodium falciparum malaria: study of antibody response by Western immunoblotting.* J Clin Microbiol, 1991. 29(3): p. 510-8.

112. Bouharoun-Tayoun, H. and P. Druilhe, *Plasmodium falciparum malaria: evidence for an isotype imbalance which may be responsible for delayed acquisition of protective immunity.* Infect Immun, 1992. 60(4): p. 1473-81.

113. Sarthou, J. L., et al., *Prognostic value of anti-Plasmodium falciparum-specific immunoglobulin G3, cytokines, and their soluble receptors in West African patients with severe malaria.* Infect Immun, 1997. 65(8): p. 3271-6.

114. Oeuvray, C., et al., *Cytophilic immunoglobulin responses to Plasmodium falciparum glutamate-rich protein are correlated with protection against clinical malaria in Dielmo, Senegal.* Infect Immun, 2000. 68(5): p. 2617-20.

115. Perlmann, P. and M. Troye-Blomberg, *Malaria blood-stage infection and its control by the immune system.* Folia Biol (Praha), 2000. 46(6): p. 210-8.

116. Yount, W. J., et al., *Studies on human antibodies. VI. Selective variations in subgroup composition and genetic markers.* J Exp Med, 1968. 127(3): p. 633-46.

117. Makela, O., et al., *Isotype concentrations of human antibodies to Haemophilus influenzae type b polysaccharide (Hib) in young adults immunized with the polysaccharide as such or conjugated to a protein (diphtheria toxoid).* J Immunol, 1987. 139(6): p. 1999-2004.

118. Ferrante, A., L. J. Beard, and R. G. Feldman, *IgG subclass distribution of antibodies to bacterial and viral antigens.* Pediatr Infect Dis J, 1990. 9(8 Suppl): p. S16-24.

119. Stein, K. E., *Thymus-independent and thymus-dependent responses to polysaccharide antigens.* J Infect Dis, 1992. 165 Suppl 1: p. 549-52.

120, Der Balian, G. P., et al., *Subclass restriction of murine antibodies. III. Antigens that stimulate IgG3 in mice stimulate IgG2c in rats.* J Exp Med, 1980. 152(1): p. 209-18.

121. Del Portillo et al., *Primary structure of the merozoite surface antigen 1 of Plasmodium vivax neveals sequences conserved between different Plasmodium species.* Proc Natl Acad Sci, 1991. 88(9): p4030-4.

REFERENCES (NUMBERS)

The following references correspond to those, for which the reference number is between parentheses, i.e.: (number).

(1) Holder, J. A. et al. (1982) Biosynthesis and processing of a *Plasmodium falciparum* schizont antigen recognized by immune serum and a monoclonal antibody". J. Exp. Med. 156:1528-1538.

(2) Howard, R. et al. (1984) "Localization of the major *Plasmodium falciparum* glycoprotein on the surface of mature intracellulartrophozoites and schizonts". Mol. Biochem. Parasitol. 11: 349-362, (3) Pinson, P. et al. (1985) "Characterization with monoclonal antibodies of a surface antigen of *Plasmodium falciparum* merozoites". J. Immuno. 134 1946-1951.

(4) Aley, S. B. et al. (1987) "*Plasmodium vivax*: Exoerythrocytic schizonts recognized by monoclonal antibodies against blood-stage schizonts". Exp. Parasitol. 64 :188-194.

(5) Holder, A. A. (1988) "The precursor to major merozoite surface antigen: structure and role in immunity". Prog. Allergy 41: 72-97.

(6) Cooper, J. A. (1993) "Merozoite surface antigen −1 of *Plasmodium*". Parasitol. Today 9: 50-54.

(7) Holder, A. A., et al. (1987) "Processing of the precursor to the major merozoite antigens of *Plasmodium falciparum*" Parasitology 94:199-208.

(8) Lyon, J. A. et al. (1986) "Epitope map and processing scheme for the 195 000-dalton surface glycoprotein of *Plasmodium falciparum* merozoites deduced from cloned overlapping segments of the gene". Proc. Natl. Acad. Sci. USA 83: 2989-2993.

(9) Blackman, M. J. et al. (1992) "Secondary processing of the *Plasmodium falciparum* merozoite surface protein-1 (MSP1) by calcium-dependent membrane-bound serine protease: shedding of $MSP1_{33}$ as a noncovalently associated complex with other fragments of the MSOP1". Mol, Biochem. Parasitol. 50: 307-316.

(10) Haldar, K., et al. (1985) "Acylation of a *Plasmodium falciparum* merozoite surface antigen via sn-1,2-diacyl glycerol.". J. Biol. Chem. 260: 4969-4974.

(11) Braun Breton, C. et al. (1990) "Glycolipid anchorage of *Plasmodium falciparum* surface antigens". Res. Immunol. 141: 743-755.

(12) Kumar, S. et al. (1995) "Immunogenicity and in vivo Efficacy of Recombinant *Plasmodium falciparum* Merozoite surface protein-1 in Aotus Monkeys". Molecular Medicine, Vol. 1, 3: 325-332.

(14) Longacre, S. et al. (1994) "*Plasmodium vivax* merozoite surface protein 1 C-terminal recombinant proteins in baculovirus". Mol. Biochem. Parasitol. 64:191-205.

(15) McBride, J. S. et al. (1987) "Fragments of the polymorphic Mr 185 000 glycoprotein from the surface of isolated *Plasmodium falciparum* merozoites form an antigenic complex". Mol. Biochem. Parasitol. 23: 71-84.

(16) Blackman, M. J. et al. (1990) "A single fragment of a malaria merozoite surface protein remains on the parasite during red cell invasion and is the target of invasion-inhibiting antibodies". J. Exp. Med. 172: 379-382.

(17) Koslow, D. C. et al. (1994) "Expression and antigenicity of *Plasmodium falciparum* major merozoite surface protein (MSP1$_{19}$) variants secreted from *Saccharomyces cerevisiae*". Mol. biochem. Parasitol. 63 ; 283-289.

(18) Chang, S. P., et al. (1992) "A carboxyl-terminal fragment of *Plasmodium falciparum* gp195 expressed by a recombinant baculovirus induces antibodies that completely inhibit parasite growth". J. Immunol. 149: 548-555

(19) Longacre, S. (1995) "The *Plasmodium cynomolgi* merozoite surface protein 1 C-terminal sequence and its homologies with other *Plasmodium species*". Mol. Biochem. Parasitol. 74:105-111.

(20) Del Portillo, H. A., et al. (1990) "Primary structure of the merozoite surface antigen 1 of *Plasmodium vivax* reveals sequences conserved between different *Plasmodium species*". Proc. Natl. Acad. Sci. USA 88: 4030-4034.

(21) Gibson, H. L., et al. (1992) "Structure and expression of the gene for Pv200, a major blood-stage surface antigen of *Plasmodium vivax*". Mol. biochem. Parasitol. 50: 325-334.

(22) Dissanaike, A. S. et al. (1965) "Two new malaria parasites, *Plasmodium cynomolgi* ceylonensis sub sp. nov. and *Plasmodium fragile* sp. nov. from monkeys in Ceylon". Ceylon Journal of Medical Science 14:1-9.

(23) Cochrane, A. H., et al. (1986) "Further studies on the antigenic diversity of the circumsporozoite proteins of the *Plasmodium cynomolgi* complex". Am. J. Trop. Med. Hyg. 35: 479-487.

(24) Naotunne, T. de S., et al. (1990) "*Plasmodium cynomolgi*: serum-mediated blocking and enhancement of infectivity to mosquitos during infections in the natural host, *Macaca sinica*". Exp. Parasitol, 71, 305-313.

(25) Ihalamulla, R. L. et al. (1987) "*Plasmodium vivax*: isolation of mature asexual stages and gametocytes from infected human blood by colloidal silica (Percoll) gradient centrifugation". Trans. R. Soc. Trop. Med. Hyg. 81:25-28.

(26) Kimura, E., et al. (1990) "Genetic diversity in the major merozoite surface antigen of *Plasmodium falciparum*: high prevalence of a third polymorphic form detected in strains derived in strains derived from malaria patients". Gene 91: 57-62.

(27) Heidrich, H.-G., et al. (1989) "The N-terminal amino acid sequences of the *Plasmodium falciparum* (FCBI) merozoite surface antigen of 42 and 36 kilodalton, both derived from the 185-195 kilodalton precursor". Mol. Biochem. Parasitol. 34 :147-154.

(28) Blackman, M. J., et al. (1991) "Proteolytic processing of the *Plasmodium falciparum* merozoite surface protein-1 produces a membrane-bound fragment containing two epidermal growth factor-like domains". Mol. Biochem. Parasitol. 49: 29-34.

(29) Adams, J. M. et al. (1992) "A family of erythrocyte binding proteins of malaria parasites". Proc. Natl. Acad. Sci, 89:7085-7089.

(30) Sim B. K. L (1995) "EBA-175: An erythrocyte-binding ligand of *Plasmodium falciparum*". Parasitology Today, vol. II, no 6:213-217.

(31) Sim B. K. L. (1994) "Receptor and ligand domains for invasion of erythrocytes by *Plasmodium falciparum*". Science, 264:1941-1944.

(32) Davies, A. et al. (1993), Biochem J. 295 (Pt3): 889 -896. "Expression of the glycosylphosphatidylinositol-linked complement-inhibiting protein CD59 antigen in insect cells using a baculovirus vector".

(33) Haziot A. et al. (1994) J. Immunol. 152: 5868. "Recombinant soluble CD14 Inhibits LPS-Induced Tumor Necrosis Factor & Production by Cells in Whole Blood".

(34) Chang, S. P. et al., (1988) "*Plasmodium falciparum*: gene structure and hydropathy profile of the major merozoite surface antigen (gp195) of the Uganda-Palo Alto isolate. Exp. Parasitol. 67 :1-11.

(35) Holder, A. S. et al. (1985) "Primary structure of the precursor to the three major surface antigens of *Plasmodium falciparum* merozoites". Nature 317: 270-273

(36) G. Bourdoiseau et al. (May 1995) "Les babesioses bovines", Le point vétérinaire, vol. 27, n-168.

(37) P. Bourdeau et al. (May 1995) "La babésiose canine à Babesia canis", Le point vétérinaire, vol. 27, n~168.

(38) C. Soule (May 1995) "Les babésioses équines", Le point vétérinaire, vol. 27 n~168.

(39) T. P. M. Schetters et al. (1995) "Vaccines against Babesiosis using Soluble Parasite Antigens", Parasitology Today, vol. 11, no 1 2.

(40) P. A. Burghaus et al. (1996) "Immunization of *Aotus nancymai* with Recombinant C Terminus of *Plasmodium falciparum* Merozoite Surface Protein 1 in Liposomes and Alum Adjuvant Does Not Induce Protection against a Challenge Infection", Infection and Immunity, 64:3614-3619.

(41) S. P. Chang, et al. (1996) A Recombinant Baculovirus 42-Kilodalton C-Terminal Fragment of *Plasmodium falciparum* Merozoite Surface Protein 1 Protects Aotus Monkeys against Malaria". Infection and Immunity, 64: 253-261.

(42) L. H. Miller et al. (1997) "The Need for Assays Predictive of Protection in Development of Malaria Bloodstage Vaccines", Parasitology Today, vol. 13, no 2:46-47.

---

The invention claimed is:

1. A purified polypeptide comprising a C-terminus Merozoite Surface Protein 1 (MSP1) antigen from *Plasmodium* carrying a Glycosyl-phosphatidyl-inositol group (GPI), wherein said GPI-carrying C-terminus MSP1 antigen from *Plasmodium* has been recombinantly produced in a baculovirus/insect cell expression system, wherein said MSP1 antigen is the MSP1-19 peptide from *Plasmodium*, wherein said MSP1-19 peptide is expressed with a His-tag, and wherein the sequence of said MSP1-19 peptide is as follows:

```
                                                   (SEQ ID NO: 2)
VTHESYQELVKKLEAFEDAVLTGYEFNTIISKLIEGKFQDMLNISQHQCV
KKQCPENSGCFRHLDEREECKCLLNYKQEGDKCVENPNPTCNENNGGCDA
DAKCTEEDSGSNGKKITCECTKPDSYPLFDGIFCSHHHHHHGIFSS.
```

2. The purified polypeptide of claim 1, wherein said MSP1 antigen is a *Plasmodium falciparum* antigen.

3. The purified polypeptide of claim 1, which is a recombinant polypeptide recovered from the plasma membrane of an insect cell where it is anchored through the GPI.

4. The purified polypeptide of claim 1, which is a recombinant polypeptide recovered from the plasma membrane of an insect cell where it is anchored through the GPI, and wherein said MSP1-19 peptide has the following amino-acid sequence:

```
                                                   (SEQ ID NO: 1)
VTHESYQELVKKLEAFEDAVLTGYEFNTIISKLIEGKFQDMLNISQHQCV
KKQCPENSGCFRHLDEREECKCLLNYKQEGDKCVENPNPTCNENNGGCDA
DAKCTEEDSGSNGKKITCECTKPDSYPLFDGIFCSGIFSS.
```

5. The purified polypeptide of claim 1, which is recognized by conformation-dependent antibodies directed against the MSP1-19 peptide.

6. The purified polypeptide of claim 1, wherein said MSP1-19 peptide reproduces the disulphide bonded double EGF-like domain structure of native MSP1p19.

7. An immunogenic composition, comprising the purified polypeptide of claim 1 and a pharmaceutically acceptable carrier.

8. The composition of claim 7, wherein said composition is devoid of an adjuvant of the immune response.

9. A vaccine against a *Plasmodium* infection, wherein said vaccine comprises an active principle which is the purified polypeptide of claim 1.

10. The vaccine of claim 9, wherein said vaccine is devoid of an adjuvant of the immune response.

11. The vaccine of claim 9, which further comprises polymer additives.

12. The vaccine of claim 9, wherein a further antigen of *Plasmodium* is added as an active principle.

13. The vaccine of claim 9 for use against infection by *Plasmodium falciparum*.

14. The polypeptide of claim 1, which comprises the amino acid sequence of SEQ ID NO 6.

15. A purified polypeptide consisting of a C-terminus Merozoite Surface Protein 1 (MSP1) antigen from *Plasmodium* carrying a Glycosyl-phosphatidyl-inositol group (GPI), wherein said GPI-carrying C-terminus MSP1 antigen from *Plasmodium* has been recombinantly produced in a baculovirus/insect cell expression system, wherein said MSP1 antigen is the MSP1-19 peptide from *Plasmodium*, wherein said MSP1-19 peptide is expressed with a His-tag, and wherein the sequence of said MSP1-19 peptide is as follows:

```
                                                   (SEQ ID NO: 2)
VTHESYQELVKKLEAFEDAVLTGYEFNTIISKLIEGKFQDMLNISQHQCV
KKQCPENSGCFRHLDEREECKCLLNYKQEGDKCVENPNPTCNENNGGCDA
DAKCTEEDSGSNGKKITCECTKPDSYPLFDGIFCSHHHHHHGIFSS.
```

16. An immunogenic composition, comprising the purified polypeptide of claim 15 and a pharmaceutically acceptable carrier.

* * * * *

SEQUENCE LISTING

```
<160> NUMBER OF SEQ ID NOS: 38

<210> SEQ ID NO 1
<211> LENGTH: 140
<212> TYPE: PRT
<213> ORGANISM: Plasmodium falciparum

<400> SEQUENCE: 1

Val Thr His Glu Ser Tyr Gln Glu Leu Val Lys Lys Leu Glu Ala Phe
1               5                   10                  15
```

```
Glu Asp Ala Val Leu Thr Gly Tyr Glu Phe Asn Thr Ile Ile Ser Lys
            20                  25                  30

Leu Ile Glu Gly Lys Phe Gln Asp Met Leu Asn Ile Ser Gln His Gln
            35                  40                  45

Cys Val Lys Lys Gln Cys Pro Glu Asn Ser Gly Cys Phe Arg His Leu
 50                      55                      60

Asp Glu Arg Glu Cys Lys Cys Leu Leu Asn Tyr Lys Gln Glu Gly
 65                      70                  75                  80

Asp Lys Cys Val Glu Asn Pro Asn Pro Thr Cys Asn Glu Asn Asn Gly
                    85                  90                      95

Gly Cys Asp Ala Asp Ala Lys Cys Thr Glu Glu Asp Ser Gly Ser Asn
                100                 105                 110

Gly Lys Lys Ile Thr Cys Glu Cys Thr Lys Pro Asp Ser Tyr Pro Leu
                115                 120                 125

Phe Asp Gly Ile Phe Cys Ser Gly Ile Phe Ser Ser
130                 135                 140

<210> SEQ ID NO 2
<211> LENGTH: 146
<212> TYPE: PRT
<213> ORGANISM: Artificial Sequence
<220> FEATURE:
<223> OTHER INFORMATION: Synthetic Peptide

<400> SEQUENCE: 2

Val Thr His Glu Ser Tyr Gln Glu Leu Val Lys Lys Leu Glu Ala Phe
 1               5                  10                  15

Glu Asp Ala Val Leu Thr Gly Tyr Glu Phe Asn Thr Ile Ile Ser Lys
            20                  25                  30

Leu Ile Glu Gly Lys Phe Gln Asp Met Leu Asn Ile Ser Gln His Gln
            35                  40                  45

Cys Val Lys Lys Gln Cys Pro Glu Asn Ser Gly Cys Phe Arg His Leu
 50                      55                      60

Asp Glu Arg Glu Cys Lys Cys Leu Leu Asn Tyr Lys Gln Glu Gly
 65                      70                  75                  80

Asp Lys Cys Val Glu Asn Pro Asn Pro Thr Cys Asn Glu Asn Asn Gly
                    85                  90                      95

Gly Cys Asp Ala Asp Ala Lys Cys Thr Glu Glu Asp Ser Gly Ser Asn
                100                 105                 110

Gly Lys Lys Ile Thr Cys Glu Cys Thr Lys Pro Asp Ser Tyr Pro Leu
                115                 120                 125

Phe Asp Gly Ile Phe Cys Ser His His His His His Gly Ile Phe
130                 135                 140

Ser Ser
145

<210> SEQ ID NO 3
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 3

Met Lys Ile Ile Phe Phe Leu Cys Ser Phe Leu Phe Phe Ile Ile Asn
 1               5                  10                  15

Thr Gln Cys
```

```
<210> SEQ ID NO 4
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 4

Ser Ser Asn Phe Leu Gly Ile Ser Phe Leu Leu Ile Leu Met Leu Ile
1               5                   10                  15

Leu Tyr Ser Phe Ile
            20

<210> SEQ ID NO 5
<211> LENGTH: 564
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(564)

<400> SEQUENCE: 5 atg aag atc ata ttc ttt ttg tgt tcg ttc ctc ttc ttc atc atc aac      48
Met Lys Ile Ile Phe Phe Leu Cys Ser Phe Leu Phe Phe Ile Ile Asn
1               5                   10                  15 acg caa tgt gtg acc cac gag agc tac caa gag ctc gtc aag aaa ctg      96
Thr Gln Cys Val Thr His Glu Ser Tyr Gln Glu Leu Val Lys Lys Leu
            20                  25                  30 gag gcc ttc gag gac gcg gtg ttg acc ggc tac gaa ttc aac acg atc     144
Glu Ala Phe Glu Asp Ala Val Leu Thr Gly Tyr Glu Phe Asn Thr Ile
        35                  40                  45 atc tcg aaa ttg atc gag ggc aaa ttc caa gac atg ttg aac atc tcg     192
Ile Ser Lys Leu Ile Glu Gly Lys Phe Gln Asp Met Leu Asn Ile Ser
    50                  55                  60 cag cac caa tgc gtg aaa aaa caa tgt ccc gag aac tct ggc tgt ttc     240
Gln His Gln Cys Val Lys Lys Gln Cys Pro Glu Asn Ser Gly Cys Phe
65                  70                  75                  80 aga cac ttg gac gag aga gag gag tgt aaa tgt ctg ctg aac tac aaa     288
Arg His Leu Asp Glu Arg Glu Glu Cys Lys Cys Leu Leu Asn Tyr Lys
                85                  90                  95 cag gag ggc gac aag tgc gtg gag aac ccc aac ccg acc tgt aac gag     336
Gln Glu Gly Asp Lys Cys Val Glu Asn Pro Asn Pro Thr Cys Asn Glu
            100                 105                 110 aac aac ggc ggc tgt gac gca gac gcc aaa tgc acc gag gag gac tcg     384
Asn Asn Gly Gly Cys Asp Ala Asp Ala Lys Cys Thr Glu Glu Asp Ser
        115                 120                 125 ggc agc aac ggc aag aaa atc acg tgt gag tgt acc aaa ccc gac tcg     432
Gly Ser Asn Gly Lys Lys Ile Thr Cys Glu Cys Thr Lys Pro Asp Ser
    130                 135                 140 tac ccg ctg ttc gac ggc atc ttc tgc agc cac cat cac cat cac cat     480
Tyr Pro Leu Phe Asp Gly Ile Phe Cys Ser His His His His His His
145                 150                 155                 160 ggc atc ttc agc agc tcc tct aac ttc ttg ggc atc tcg ttc ttg ttg     528
Gly Ile Phe Ser Ser Ser Ser Asn Phe Leu Gly Ile Ser Phe Leu Leu
                165                 170                 175 atc ctc atg ttg atc ttg tac agc ttc att taa taa                     564
Ile Leu Met Leu Ile Leu Tyr Ser Phe Ile
            180                 185

<210> SEQ ID NO 6
<211> LENGTH: 186
<212> TYPE: PRT
```

```
<213> ORGANISM: Artificial Sequence
<220> FEATURE:
<223> OTHER INFORMATION: Synthetic Peptide

<400> SEQUENCE: 6

Met Lys Ile Ile Phe Phe Leu Cys Ser Phe Leu Phe Ile Ile Asn
1               5                   10                  15

Thr Gln Cys Val Thr His Glu Ser Tyr Gln Glu Leu Val Lys Lys Leu
            20                  25                  30

Glu Ala Phe Glu Asp Ala Val Leu Thr Gly Tyr Glu Phe Asn Thr Ile
                35                  40                  45

Ile Ser Lys Leu Ile Glu Gly Lys Phe Gln Asp Met Leu Asn Ile Ser
        50                  55                  60

Gln His Gln Cys Val Lys Lys Gln Cys Pro Glu Asn Ser Gly Cys Phe
65                  70                  75                  80

Arg His Leu Asp Glu Arg Glu Cys Lys Cys Leu Leu Asn Tyr Lys
                85                  90                  95

Gln Glu Gly Asp Lys Cys Val Glu Asn Pro Asn Pro Thr Cys Asn Glu
                100                 105                 110

Asn Asn Gly Gly Cys Asp Ala Asp Ala Lys Cys Thr Glu Glu Asp Ser
            115                 120                 125

Gly Ser Asn Gly Lys Lys Ile Thr Cys Glu Cys Thr Lys Pro Asp Ser
130                 135                 140

Tyr Pro Leu Phe Asp Gly Ile Phe Cys Ser His His His His His
145                 150                 155                 160

Gly Ile Phe Ser Ser Ser Ser Asn Phe Leu Gly Ile Ser Phe Leu Leu
                165                 170                 175

Ile Leu Met Leu Ile Leu Tyr Ser Phe Ile
            180                 185

<210> SEQ ID NO 7
<211> LENGTH: 49
<212> TYPE: DNA
<213> ORGANISM: Artificial Sequence
<220> FEATURE:
<223> OTHER INFORMATION: Synthetic DNA

<400> SEQUENCE: 7
cccggatccg aaaatgaaga tcatattctt tttgtgttcg ttcctcttc                49

<210> SEQ ID NO 8
<211> LENGTH: 48
<212> TYPE: DNA
<213> ORGANISM: Artificial Sequence
<220> FEATURE:
<223> OTHER INFORMATION: Synthetic DNA

<400> SEQUENCE: 8
tctcgtgggt cacacattgc gtgttgatga tgaagaagag gaacgaac                 48

<210> SEQ ID NO 9
<211> LENGTH: 50
<212> TYPE: DNA
<213> ORGANISM: Artificial Sequence
<220> FEATURE:
<223> OTHER INFORMATION: Synthetic DNA

<400> SEQUENCE: 9
gtgtgaccca cgagagctac caagagctcg tcaagaaact ggaggccttc               50

<210> SEQ ID NO 10
```

```
<211> LENGTH: 50
<212> TYPE: DNA
<213> ORGANISM: Artificial Sequence
<220> FEATURE:
<223> OTHER INFORMATION: Synthetic DNA

<400> SEQUENCE: 10
cccgaattcg tagccggtca acaccgcgtc ctcgaaaggc ctccagtttc                  50

<210> SEQ ID NO 11
<211> LENGTH: 84
<212> TYPE: DNA
<213> ORGANISM: Artificial Sequence
<220> FEATURE:
<223> OTHER INFORMATION: Synthetic DNA

<400> SEQUENCE: 11
ggggaattca acatctcgca gcaccaatgc gtgaaaaaac aatgtcccga gaactctggc      60
tgtttcagac acttggacga gaga                                             84

<210> SEQ ID NO 12
<211> LENGTH: 87
<212> TYPE: DNA
<213> ORGANISM: Artificial Sequence
<220> FEATURE:
<223> OTHER INFORMATION: Synthetic DNA

<400> SEQUENCE: 12
acaggtcggg ttggggttct ccacgcactt gtcgccctcc tgtttgtagt tcagcagaca      60
tttacactcc tctctctcgt ccaagtg                                          87

<210> SEQ ID NO 13
<211> LENGTH: 84
<212> TYPE: DNA
<213> ORGANISM: Artificial Sequence
<220> FEATURE:
<223> OTHER INFORMATION: Synthetic DNA

<400> SEQUENCE: 13
cccaacccga cctgtaacga gaacaacggc ggctgtgacg ccgacgccaa atgcaccgag      60
gaggactcgg gcagcaacgg caag                                             84

<210> SEQ ID NO 14
<211> LENGTH: 84
<212> TYPE: DNA
<213> ORGANISM: Artificial Sequence
<220> FEATURE:
<223> OTHER INFORMATION: Synthetic DNA

<400> SEQUENCE: 14
agaggagctg cagaagatgc cgtcgaacag cgggtacgag tcgggtttgg tacactcaca      60
cgtgattttc ttgccgttgc tgcc                                             84

<210> SEQ ID NO 15
<211> LENGTH: 87
<212> TYPE: DNA
<213> ORGANISM: Artificial Sequence
<220> FEATURE:
<223> OTHER INFORMATION: Synthetic DNA

<400> SEQUENCE: 15
ttctgcagct cctctaactt cttgggcatc tcgttcttgt tgatcctcat gttgatcttg      60
tacagcttca tttaataaag atctccc                                          87
```

```
<210> SEQ ID NO 16
<211> LENGTH: 23
<212> TYPE: DNA
<213> ORGANISM: Artificial Sequence
<220> FEATURE:
<223> OTHER INFORMATION: Synthetic DNA

<400> SEQUENCE: 16
gggagatctt tattaaatga agc                                              23

<210> SEQ ID NO 17
<211> LENGTH: 22
<212> TYPE: DNA
<213> ORGANISM: Artificial Sequence
<220> FEATURE:
<223> OTHER INFORMATION: Synthetic DNA

<400> SEQUENCE: 17
ggggaattca acatctcgca gc                                               22

<210> SEQ ID NO 18
<211> LENGTH: 45
<212> TYPE: DNA
<213> ORGANISM: Artificial Sequence
<220> FEATURE:
<223> OTHER INFORMATION: Synthetic DNA

<400> SEQUENCE: 18
gcccaaagat ctttattagc tgcagaagat gccgtcgaac agcgg                      45

<210> SEQ ID NO 19
<211> LENGTH: 516
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(516)

<400> SEQUENCE: 19 atg aag gcg cta ctc ttt ttg ttc tct ttc att ttt ttc gtt acc aaa        48
Met Lys Ala Leu Leu Phe Leu Phe Ser Phe Ile Phe Phe Val Thr Lys
1               5                   10                  15 tgt caa tgt gaa aca gaa agt tat aag cag ctt gta gcc aac gtg gac        96
Cys Gln Cys Glu Thr Glu Ser Tyr Lys Gln Leu Val Ala Asn Val Asp
            20                  25                  30 gaa ttc ata tta tcc cag ctg cta aat gtg caa act cag tta tta act       144
Glu Phe Ile Leu Ser Gln Leu Leu Asn Val Gln Thr Gln Leu Leu Thr
        35                  40                  45 atg agc tcc gag cac aca tgt ata gac acc aat gtg cct gat aat gca       192
Met Ser Ser Glu His Thr Cys Ile Asp Thr Asn Val Pro Asp Asn Ala
    50                  55                  60 gcc tgc tat agg tac ttg gac gga acg gaa gaa tgg aga tgc ttg tta       240
Ala Cys Tyr Arg Tyr Leu Asp Gly Thr Glu Glu Trp Arg Cys Leu Leu
65                  70                  75                  80 acc ttt aaa gaa gaa ggc ggc aag tgt gtg cca gca tcg aat gtg act       288
Thr Phe Lys Glu Glu Gly Gly Lys Cys Val Pro Ala Ser Asn Val Thr
                85                  90                  95 tgt aag gat aac aat ggt ggt tgt gcc cct gaa gct gaa tgt aaa atg       336
Cys Lys Asp Asn Asn Gly Gly Cys Ala Pro Glu Ala Glu Cys Lys Met
            100                 105                 110 acg gac agc aat aaa atc gtc tgt aaa tgt act aaa gaa ggt tct gag       384
Thr Asp Ser Asn Lys Ile Val Cys Lys Cys Thr Lys Glu Gly Ser Glu
        115                 120                 125
```

```
cca ctc ttt gag gga gtt ttc tgt agc cac cat cac cat cac cat gga      432
Pro Leu Phe Glu Gly Val Phe Cys Ser His His His His His His Gly
    130                 135                 140 gtt ttc tct agc tcc tcc agc ttc cta agc ttg tcc ttc ttg ttg ctc      480
Val Phe Ser Ser Ser Ser Ser Phe Leu Ser Leu Ser Phe Leu Leu Leu
145                 150                 155                 160 atg ttg ctt ttc ctc ctg tgc atg gag ctt taa taa                      516
Met Leu Leu Phe Leu Leu Cys Met Glu Leu
                165                 170
```

<210> SEQ ID NO 20
<211> LENGTH: 170
<212> TYPE: PRT
<213> ORGANISM: Artificial Sequence
<220> FEATURE:
<223> OTHER INFORMATION: Synthetic Peptide

<400> SEQUENCE: 20

```
Met Lys Ala Leu Leu Phe Leu Phe Ser Phe Ile Phe Phe Val Thr Lys
1               5                   10                  15

Cys Gln Cys Glu Thr Glu Ser Tyr Lys Gln Leu Val Ala Asn Val Asp
            20                  25                  30

Glu Phe Ile Leu Ser Gln Leu Leu Asn Val Gln Thr Gln Leu Leu Thr
        35                  40                  45

Met Ser Ser Glu His Thr Cys Ile Asp Thr Asn Val Pro Asp Asn Ala
    50                  55                  60

Ala Cys Tyr Arg Tyr Leu Asp Gly Thr Glu Glu Trp Arg Cys Leu Leu
65                  70                  75                  80

Thr Phe Lys Glu Glu Gly Gly Lys Cys Val Pro Ala Ser Asn Val Thr
                85                  90                  95

Cys Lys Asp Asn Asn Gly Gly Cys Ala Pro Glu Ala Glu Cys Lys Met
            100                 105                 110

Thr Asp Ser Asn Lys Ile Val Cys Lys Cys Thr Lys Glu Gly Ser Glu
        115                 120                 125

Pro Leu Phe Glu Gly Val Phe Cys Ser His His His His His His Gly
    130                 135                 140

Val Phe Ser Ser Ser Ser Ser Phe Leu Ser Leu Ser Phe Leu Leu Leu
145                 150                 155                 160

Met Leu Leu Phe Leu Leu Cys Met Glu Leu
                165                 170
```

<210> SEQ ID NO 21
<211> LENGTH: 127
<212> TYPE: DNA
<213> ORGANISM: Artificial Sequence
<220> FEATURE:
<223> OTHER INFORMATION: Synthetic DNA

<400> SEQUENCE: 21

```
gccgtagaag acgtcggtgg tagtggtagt ggtaccgtag aagtcgtcga ggagattgaa      60
gaacccgtag agcaagaaca actaggagta caactagaac atgtcgaagt aaattatttc     120
tagaccc                                                               127
```

<210> SEQ ID NO 22
<211> LENGTH: 73
<212> TYPE: DNA
<213> ORGANISM: Artificial Sequence
<220> FEATURE:
<223> OTHER INFORMATION: Synthetic DNA -continued

<400> SEQUENCE: 22

```
ccggaattca acacgatcat ctcgaaattg atcgagggca aattccaaga catgttgaac    60
atctcgcagc acc                                                      73
```

<210> SEQ ID NO 23
<211> LENGTH: 57
<212> TYPE: DNA
<213> ORGANISM: Artificial Sequence
<220> FEATURE:
<223> OTHER INFORMATION: Synthetic DNA

<400> SEQUENCE: 23

```
gggagatctt tattaatggt gatggtgatg gtggctgcag aagatgccgt cgaacag    57
```

<210> SEQ ID NO 24
<211> LENGTH: 291
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(291)

<400> SEQUENCE: 24

```
gaa ttc aac atc tcg cag cac caa tgc gtg aaa aaa caa tgt ccc gag      48
Glu Phe Asn Ile Ser Gln His Gln Cys Val Lys Lys Gln Cys Pro Glu
1               5                   10                  15 aac tct ggc tgt ttc aga cac ttg gac gag aga gag gag tgt aaa tgt      96
Asn Ser Gly Cys Phe Arg His Leu Asp Glu Arg Glu Glu Cys Lys Cys
            20                  25                  30 ctg ctg aac tac aaa cag gag ggc gac aag tgc gtg gag aac ccc aac     144
Leu Leu Asn Tyr Lys Gln Glu Gly Asp Lys Cys Val Glu Asn Pro Asn
        35                  40                  45 ccg acc tgt aac gag aac aac ggc ggt tgt gac gca gac gcc aaa tgc     192
Pro Thr Cys Asn Glu Asn Asn Gly Gly Cys Asp Ala Asp Ala Lys Cys
    50                  55                  60 acc gag gag gac tcg ggc agc aac ggc aag aaa atc acg tgt gag tgt     240
Thr Glu Glu Asp Ser Gly Ser Asn Gly Lys Lys Ile Thr Cys Glu Cys
65                  70                  75                  80 acc aaa ccc gac tcg tac ccg ctg ttc gac ggc atc ttc tgc agc taa     288
Thr Lys Pro Asp Ser Tyr Pro Leu Phe Asp Gly Ile Phe Cys Ser
                85                  90                  95 taa                                                                 291
```

<210> SEQ ID NO 25
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 25

```
Glu Phe Asn Ile Ser Gln His Gln Cys Val Lys Lys Gln Cys Pro Glu
1               5                   10                  15

Asn Ser Gly Cys Phe Arg His Leu Asp Glu Arg Glu Glu Cys Lys Cys
            20                  25                  30

Leu Leu Asn Tyr Lys Gln Glu Gly Asp Lys Cys Val Glu Asn Pro Asn
        35                  40                  45

Pro Thr Cys Asn Glu Asn Asn Gly Gly Cys Asp Ala Asp Ala Lys Cys
    50                  55                  60

Thr Glu Glu Asp Ser Gly Ser Asn Gly Lys Lys Ile Thr Cys Glu Cys
```

```
                   65                  70                  75                  80
Thr Lys Pro Asp Ser Tyr Pro Leu Phe Asp Gly Ile Phe Cys Ser
                        85                  90                  95

<210> SEQ ID NO 26
<211> LENGTH: 279
<212> TYPE: DNA
<213> ORGANISM: Plasmodium falciparum

<400> SEQUENCE: 26
aacatttcac aacaccaatg cgtaaaaaaa caatgtccag aaaattctgg atgtttcaga      60
catttagatg aaagagaaga atgtaaatgt ttattaaatt acaaacaaga aggtgataaa     120
tgtgttgaaa atccaaatcc tacttgtaac gaaaataatg gtggatgtga tgcagatgcc     180
aaatgtaccg aagaagattc aggtagcaac ggaaagaaaa tcacatgtga atgtactaaa     240
cctgattctt atccactttt cgatggtatt ttctgcagt                            279

<210> SEQ ID NO 27
<211> LENGTH: 354
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(354)

<400> SEQUENCE: 27 gaa ttc aac atc tcg cag cac caa tgc gtg aaa aaa caa tgt ccc gag       48
Glu Phe Asn Ile Ser Gln His Gln Cys Val Lys Lys Gln Cys Pro Glu
1               5                   10                  15 aac tct ggc tgt ttc aga cac ttg gac gag aga gag gag tgt aaa tgt       96
Asn Ser Gly Cys Phe Arg His Leu Asp Glu Arg Glu Glu Cys Lys Cys
            20                  25                  30 ctg ctg aac tac aaa cag gag ggc gac aag tgc gtg gag aac ccc aac      144
Leu Leu Asn Tyr Lys Gln Glu Gly Asp Lys Cys Val Glu Asn Pro Asn
        35                  40                  45 ccg acc tgt aac gag aac aac ggc ggc tgt gac gca gac gcc aaa tgc      192
Pro Thr Cys Asn Glu Asn Asn Gly Gly Cys Asp Ala Asp Ala Lys Cys
    50                  55                  60 acc gag gag gac tcg ggc agc aac ggc aag aaa atc acg tgt gag tgt      240
Thr Glu Glu Asp Ser Gly Ser Asn Gly Lys Lys Ile Thr Cys Glu Cys
65                  70                  75                  80 acc aaa ccc gac tcg tac ccg ctg ttc gac ggc atc ttc tgc agc tcc      288
Thr Lys Pro Asp Ser Tyr Pro Leu Phe Asp Gly Ile Phe Cys Ser Ser
                85                  90                  95 tct aac ttc ttg ggc atc tcg ttc ttg ttg atc ctc atg ttg atc ttg      336
Ser Asn Phe Leu Gly Ile Ser Phe Leu Leu Ile Leu Met Leu Ile Leu
            100                 105                 110 tac agc ttc att taa taa                                              354
Tyr Ser Phe Ile
        115

<210> SEQ ID NO 28
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 28

Glu Phe Asn Ile Ser Gln His Gln Cys Val Lys Lys Gln Cys Pro Glu
1               5                   10                  15
```

```
Asn Ser Gly Cys Phe Arg His Leu Asp Glu Arg Glu Cys Lys Cys
         20                  25                  30

Leu Leu Asn Tyr Lys Gln Glu Gly Asp Lys Cys Val Glu Asn Pro Asn
         35                  40                  45

Pro Thr Cys Asn Glu Asn Gly Gly Cys Asp Ala Asp Ala Lys Cys
     50                  55                  60

Thr Glu Glu Asp Ser Gly Ser Asn Gly Lys Lys Ile Thr Cys Glu Cys
65                   70                  75                  80

Thr Lys Pro Asp Ser Tyr Pro Leu Phe Asp Gly Ile Phe Cys Ser Ser
                 85                  90                  95

Ser Asn Phe Leu Gly Ile Ser Phe Leu Leu Ile Leu Met Leu Ile Leu
             100                 105                 110

Tyr Ser Phe Ile
         115

<210> SEQ ID NO 29
<211> LENGTH: 342
<212> TYPE: DNA
<213> ORGANISM: Plasmodium falciparum

<400> SEQUENCE: 29
aacatttcac aacaccaatg cgtaaaaaaa caatgtccag aaaattctgg atgtttcaga      60
catttagatg aaagagaaga atgtaaatgt ttattaaatt acaaacaaga aggtgataaa     120
tgtgttgaaa atccaaatcc tacttgtaac gaaataatg gtggatgtga tgcagatgcc     180
aaatgtaccg aagaagattc aggtagcaac ggaaagaaaa tcacatgtga atgtactaaa     240
cctgattctt atccactttt cgatggtatt ttctgcagtt cctctaactt cttaggaata     300
tcattcttat taatactcat gttaatatta tacagtttca tt                       342

<210> SEQ ID NO 30
<211> LENGTH: 387
<212> TYPE: DNA
<213> ORGANISM: Plasmodium falciparum
<220> FEATURE:
<221> NAME/KEY: CDS
<222> LOCATION: (1)..(387)

<400> SEQUENCE: 30 atg aag gcg cta ctc ttt ttg ttc tct ttc att ttt ttc gtt acc aaa       48
Met Lys Ala Leu Leu Phe Leu Phe Ser Phe Ile Phe Phe Val Thr Lys
1               5                   10                  15 gaa ttc aac atc tcg cag cac caa tgc gtg aaa aaa caa tgt ccc gag       96
Glu Phe Asn Ile Ser Gln His Gln Cys Val Lys Lys Gln Cys Pro Glu
             20                  25                  30 gaa ttc aac atc tcg cag cac caa tgc gtg aaa aaa caa tgt ccc gag      144
Glu Phe Asn Ile Ser Gln His Gln Cys Val Lys Lys Gln Cys Pro Glu
             35                  40                  45 aac tct ggc tgt ttc aga cac ttg gac gag aga gag gag tgt aaa tgt      192
Asn Ser Gly Cys Phe Arg His Leu Asp Glu Arg Glu Cys Lys Cys
         50                  55                  60 ctg ctg aac tac aaa cag gag ggc gac aag tgc gtg gag aac ccc aac      240
Leu Leu Asn Tyr Lys Gln Glu Gly Asp Lys Cys Val Glu Asn Pro Asn
65                  70                  75                  80 ccg acc tgt aac gag aac aac ggc ggc tgt gac gca gac gcc aaa tgc      288
Pro Thr Cys Asn Glu Asn Asn Gly Gly Cys Asp Ala Asp Ala Lys Cys
                 85                  90                  95 acc gag gag gac tcg ggc agc aac ggc aag aaa atc acg tgt gag tgt      336
Thr Glu Glu Asp Ser Gly Ser Asn Gly Lys Lys Ile Thr Cys Glu Cys
             100                 105                 110
```

```
acc aaa ccc gac tcg tac ccg ctg ttc gac ggc atc ttc tgc agc taa        384
Thr Lys Pro Asp Ser Tyr Pro Leu Phe Asp Gly Ile Phe Cys Ser
        115                 120                 125 taa                                                                     387

<210> SEQ ID NO 31
<211> LENGTH: 127
<212> TYPE: PRT
<213> ORGANISM: Plasmodium falciparum

<400> SEQUENCE: 31

Met Lys Ala Leu Leu Phe Leu Phe Ser Phe Ile Phe Phe Val Thr Lys
1               5                   10                  15

Glu Phe Asn Ile Ser Gln His Gln Cys Val Lys Lys Gln Cys Pro Glu
            20                  25                  30

Glu Phe Asn Ile Ser Gln His Gln Cys Val Lys Lys Gln Cys Pro Glu
        35                  40                  45

Asn Ser Gly Cys Phe Arg His Leu Asp Glu Arg Glu Glu Cys Lys Cys
    50                  55                  60

Leu Leu Asn Tyr Lys Gln Glu Gly Asp Lys Cys Val Glu Asn Pro Asn
65                  70                  75                  80

Pro Thr Cys Asn Glu Asn Asn Gly Gly Cys Asp Ala Asp Ala Lys Cys
                85                  90                  95

Thr Glu Glu Asp Ser Gly Ser Asn Gly Lys Lys Ile Thr Cys Glu Cys
            100                 105                 110

Thr Lys Pro Asp Ser Tyr Pro Leu Phe Asp Gly Ile Phe Cys Ser
        115                 120                 125

<210> SEQ ID NO 32
<211> LENGTH: 330
<212> TYPE: DNA
<213> ORGANISM: Plasmodium falciparum
<220> FEATURE:
<221> NAME/KEY: CDS
<222> LOCATION: (1)..(330)

<400> SEQUENCE: 32 gaa aca gaa agt tat aag cag ctt gta gcc aac gtg gac gaa ttc aac         48
Glu Thr Glu Ser Tyr Lys Gln Leu Val Ala Asn Val Asp Glu Phe Asn
1               5                   10                  15 atc tcg cag cac caa tgc gtg aaa aaa caa tgt ccc gag aac tct ggc         96
Ile Ser Gln His Gln Cys Val Lys Lys Gln Cys Pro Glu Asn Ser Gly
            20                  25                  30 tgt ttc aga cac ttg gac gag aga gag gag tgt aaa tgt ctg ctg aac        144
Cys Phe Arg His Leu Asp Glu Arg Glu Glu Cys Lys Cys Leu Leu Asn
        35                  40                  45 tac aaa cag gag ggc gac aag tgc gtg gag aac ccc aac ccg acc tgt        192
Tyr Lys Gln Glu Gly Asp Lys Cys Val Glu Asn Pro Asn Pro Thr Cys
    50                  55                  60 aac gag aac aac ggc ggc tgt gac gca gac gcc aaa tgc acc gag gag        240
Asn Glu Asn Asn Gly Gly Cys Asp Ala Asp Ala Lys Cys Thr Glu Glu
65                  70                  75                  80 gac tcg ggc agc aac ggc aag aaa atc acg tgt gag tgt acc aaa ccc        288
Asp Ser Gly Ser Asn Gly Lys Lys Ile Thr Cys Glu Cys Thr Lys Pro
                85                  90                  95 gac tcg tac ccg ctg ttc gac ggc atc ttc tgc agc taa taa                330
Asp Ser Tyr Pro Leu Phe Asp Gly Ile Phe Cys Ser
            100                 105

<210> SEQ ID NO 33
```

```
<211> LENGTH: 108
<212> TYPE: PRT
<213> ORGANISM: Plasmodium falciparum

<400> SEQUENCE: 33

Glu Thr Glu Ser Tyr Lys Gln Leu Val Ala Asn Val Asp Glu Phe Asn
1               5                   10                  15

Ile Ser Gln His Gln Cys Val Lys Lys Gln Cys Pro Glu Asn Ser Gly
            20                  25                  30

Cys Phe Arg His Leu Asp Glu Arg Glu Cys Lys Cys Leu Leu Asn
        35                  40                  45

Tyr Lys Gln Glu Gly Asp Lys Cys Val Glu Asn Pro Asn Pro Thr Cys
    50                  55                  60

Asn Glu Asn Asn Gly Gly Cys Asp Ala Asp Ala Lys Cys Thr Glu Glu
65                  70                  75                  80

Asp Ser Gly Ser Asn Gly Lys Lys Ile Thr Cys Glu Cys Thr Lys Pro
                85                  90                  95

Asp Ser Tyr Pro Leu Phe Asp Gly Ile Phe Cys Ser
            100                 105

<210> SEQ ID NO 34
<211> LENGTH: 379
<212> TYPE: PRT
<213> ORGANISM: Plasmodium cynomolgi

<400> SEQUENCE: 34

Asp Gln Val Thr Thr Gly Glu Ala Glu Ser Glu Ala Pro Glu Ile Ile
1               5                   10                  15

Val Pro Gln Gly Ile Asn Glu Tyr Asp Val Val Tyr Ile Lys Pro Leu
            20                  25                  30

Ala Gly Met Tyr Lys Thr Ile Lys Lys Pro Leu Glu Asn His Val Asn
        35                  40                  45

Ala Leu Asn Thr Asn Ile Ile Asp Met Leu Asp Ser Arg Leu Lys Lys
    50                  55                  60

Arg Asn Tyr Phe Leu Asp Val Leu Asn Ser Asp Leu Asn Pro Tyr Ser
65                  70                  75                  80

Ile Pro His Ser Gly Glu Tyr Ile Ile Lys Asp Pro Tyr Lys Leu Leu
                85                  90                  95

Asp Leu Glu Lys Lys Leu Leu Gly Ser Tyr Lys Tyr Ile Gly Ala
            100                 105                 110

Ser Val Asp Lys Asp Met Val Thr Ala Asn Asp Gly Leu Ala Tyr Tyr
        115                 120                 125

Gln Lys Met Gly Asp Leu Tyr Lys Lys His Leu Asp Glu Val Asn Ala
    130                 135                 140

Cys Ile Lys Glu Val Glu Ala Asn Ile Asn Lys His Asp Glu Glu Ile
145                 150                 155                 160

Lys Lys Ile Gly Ser Glu Ala Ser Lys Ala Asn Asp Lys Asn Gln Leu
                165                 170                 175

Asn Ala Lys Lys Glu Glu Leu Gln Lys Tyr Leu Pro Phe Leu Ser Ser
            180                 185                 190

Ile Gln Lys Glu Tyr Ser Thr Leu Val Asn Lys Val His Ser Tyr Thr
        195                 200                 205

Asp Thr Leu Lys Lys Ile Ile Asn Asn Cys Gln Ile Glu Lys Lys Glu
    210                 215                 220

Thr Glu Thr Ile Val Asn Lys Leu Glu Asp Tyr Ser Lys Met Asp Glu
225                 230                 235                 240
```

```
Glu Leu Asp Val Tyr Lys Gln Ser Lys Lys Glu Asp Val Lys Ser
                245                 250                 255

Ser Gly Leu Leu Glu Lys Leu Met Asn Ser Lys Leu Ile Asn Gln Glu
        260                 265                 270

Glu Ser Lys Lys Ala Leu Ser Glu Leu Leu Asn Val Gln Thr Gln Met
        275                 280                 285

Leu Asn Met Ser Ser Glu His Arg Cys Ile Asp Thr Asn Val Pro Glu
    290                 295                 300

Asn Ala Ala Cys Tyr Arg Tyr Leu Asp Gly Thr Glu Glu Trp Arg Cys
305                 310                 315                 320

Leu Leu Tyr Phe Lys Glu Asp Ala Gly Lys Cys Val Pro Ala Pro Asn
                325                 330                 335

Met Thr Cys Lys Asp Lys Asn Gly Gly Cys Ala Pro Glu Ala Glu Cys
                340                 345                 350

Lys Met Asn Asp Lys Asn Glu Ile Val Cys Lys Cys Thr Lys Glu Gly
                355                 360                 365

Ser Glu Pro Leu Phe Glu Gly Val Phe Cys Ser
        370                 375

<210> SEQ ID NO 35
<211> LENGTH: 380
<212> TYPE: PRT
<213> ORGANISM: Plasmodium vivax-like sp.

<400> SEQUENCE: 35

Asp Gln Val Thr Thr Gly Glu Ala Glu Ser Glu Ala Pro Glu Ile Leu
1               5                  10                  15

Val Pro Ala Gly Ile Ser Asp Tyr Asp Val Val Tyr Leu Lys Pro Leu
            20                  25                  30

Ala Gly Met Tyr Lys Thr Ile Lys Lys Gln Leu Glu Asn His Val Asn
        35                  40                  45

Ala Phe Asn Thr Asn Ile Thr Asp Met Leu Asp Ser Arg Leu Lys Lys
    50                  55                  60

Arg Asn Tyr Phe Leu Glu Val Leu Asn Ser Asp Leu Asn Pro Phe Lys
65                  70                  75                  80

Tyr Ser Pro Ser Gly Glu Tyr Ile Ile Lys Asp Pro Tyr Lys Leu Leu
                85                  90                  95

Asp Leu Glu Lys Lys Lys Leu Leu Gly Ser Tyr Lys Tyr Ile Gly
            100                 105                 110

Ala Ser Ile Asp Lys Asp Leu Ala Thr Ala Asn Asp Gly Val Thr Tyr
        115                 120                 125

Tyr Asn Lys Met Gly Glu Leu Tyr Lys Thr His Leu Thr Ala Val Asn
    130                 135                 140

Glu Glu Val Lys Lys Val Glu Ala Asp Ile Lys Ala Glu Asp Asp Lys
145                 150                 155                 160

Ile Lys Lys Ile Gly Ser Asp Ser Thr Lys Thr Thr Glu Lys Thr Gln
                165                 170                 175

Ser Met Ala Lys Lys Ala Glu Leu Glu Lys Tyr Leu Pro Phe Leu Asn
            180                 185                 190

Ser Leu Gln Lys Glu Tyr Glu Ser Leu Val Ser Lys Val Asn Thr Tyr
        195                 200                 205

Thr Asp Asn Leu Lys Lys Val Ile Asn Asn Cys Gln Leu Glu Lys Lys
    210                 215                 220

Glu Ala Glu Ile Thr Val Lys Lys Leu Gln Asp Tyr Asn Lys Met Asp
225                 230                 235                 240
```

Glu Lys Leu Glu Glu Tyr Lys Ser Glu Lys Asn Glu Val Lys
            245                 250                 255

Ser Ser Gly Leu Leu Glu Lys Leu Met Lys Ser Lys Leu Ile Lys Glu
            260                 265                 270

Asn Glu Ser Lys Glu Ile Leu Ser Gln Leu Leu Asn Val Gln Thr Gln
            275                 280                 285

Leu Leu Thr Met Ser Ser Glu His Thr Cys Ile Asp Thr Asn Val Pro
290                 295                 300

Asp Asn Ala Ala Cys Tyr Arg Tyr Leu Asp Gly Thr Glu Glu Trp Arg
305                 310                 315                 320

Cys Leu Leu Thr Phe Lys Glu Gly Gly Lys Cys Val Pro Ala Ser
            325                 330                 335

Asn Val Thr Cys Lys Asp Asn Asn Gly Gly Cys Ala Pro Glu Ala Glu
            340                 345                 350

Cys Lys Met Thr Asp Ser Asn Lys Ile Val Cys Lys Cys Thr Lys Glu
            355                 360                 365

Gly Ser Glu Pro Leu Phe Glu Gly Val Phe Cys Ser
370                 375                 380

<210> SEQ ID NO 36
<211> LENGTH: 380
<212> TYPE: PRT
<213> ORGANISM: Plasmodium vivax-like sp.

<400> SEQUENCE: 36

Asp Gln Val Thr Thr Gly Glu Ala Glu Ser Glu Ala Pro Glu Ile Leu
1               5                   10                  15

Val Pro Ala Gly Ile Ser Asp Tyr Asp Val Val Tyr Leu Lys Pro Leu
            20                  25                  30

Ala Gly Met Tyr Lys Thr Ile Lys Lys Gln Leu Glu Asn His Val Asn
            35                  40                  45

Ala Phe Asn Thr Asn Ile Thr Asp Met Leu Asp Ser Arg Leu Lys Lys
        50                  55                  60

Arg Asn Tyr Phe Leu Glu Val Leu Asn Ser Asp Leu Asn Pro Phe Lys
65                  70                  75                  80

Tyr Ser Ser Ser Gly Glu Tyr Ile Ile Lys Asp Pro Tyr Lys Leu Leu
                85                  90                  95

Asp Leu Glu Lys Lys Lys Leu Ile Gly Ser Tyr Lys Tyr Ile Gly
            100                 105                 110

Ala Ser Ile Asp Met Asp Leu Ala Thr Ala Asn Asp Gly Val Thr Tyr
            115                 120                 125

Tyr Asn Lys Met Gly Glu Leu Tyr Lys Thr His Leu Asp Gly Val Lys
        130                 135                 140

Thr Glu Ile Lys Lys Val Glu Asp Ile Lys Lys Gln Asp Glu Glu
145                 150                 155                 160

Leu Lys Lys Leu Gly Asn Val Asn Ser Gln Asp Ser Lys Lys Asn Glu
                165                 170                 175

Phe Ile Ala Lys Lys Ala Glu Leu Glu Lys Tyr Leu Pro Phe Leu Asn
            180                 185                 190

Ser Leu Gln Lys Glu Tyr Glu Ser Leu Val Ser Lys Val Asn Thr Tyr
            195                 200                 205

Thr Asp Asn Leu Lys Lys Val Ile Asn Asn Cys Gln Leu Glu Lys Lys
        210                 215                 220

Glu Ala Glu Ile Thr Val Lys Lys Leu Gln Asp Tyr Asn Lys Met Asp
225                 230                 235                 240

```
Glu Lys Leu Glu Glu Tyr Lys Lys Ser Glu Lys Lys Asn Glu Val Lys
            245                 250                 255

Ser Ser Gly Leu Leu Glu Lys Leu Met Lys Ser Lys Leu Ile Lys Glu
            260                 265                 270

Asn Glu Ser Lys Glu Ile Leu Ser Gln Leu Leu Asn Val Gln Thr Gln
            275                 280                 285

Leu Leu Thr Met Ser Ser Glu His Thr Cys Ile Asp Thr Asn Val Pro
            290                 295                 300

Asp Asn Ala Ala Cys Tyr Arg Tyr Leu Asp Gly Thr Glu Glu Trp Arg
305                 310                 315                 320

Cys Leu Leu Thr Phe Lys Glu Gly Gly Lys Cys Val Pro Ala Ser
            325                 330                 335

Asn Val Thr Cys Lys Asp Asn Gly Gly Cys Ala Pro Glu Ala Glu
            340                 345                 350

Cys Lys Met Thr Asp Ser Asn Lys Ile Val Cys Lys Cys Thr Lys Glu
            355                 360                 365

Gly Ser Glu Pro Leu Phe Glu Gly Val Phe Cys Ser
370                 375                 380

<210> SEQ ID NO 37
<211> LENGTH: 281
<212> TYPE: PRT
<213> ORGANISM: Artificial Sequence
<220> FEATURE:
<223> OTHER INFORMATION: Synthetic Peptide

<400> SEQUENCE: 37

Asp Gln Val Thr Thr Gly Glu Ala Glu Ser Glu Ala Pro Glu Ile Val
1               5                   10                  15

Pro Gly Ile Tyr Asp Val Val Tyr Lys Pro Leu Ala Gly Met Tyr Lys
            20                  25                  30

Thr Ile Lys Lys Leu Glu Asn His Val Asn Ala Asn Thr Asn Ile Asp
            35                  40                  45

Met Leu Asp Ser Ala Leu Lys Lys Ala Asn Tyr Phe Leu Val Leu Asn
        50                  55                  60

Ser Asp Leu Asn Pro Ser Gly Glu Tyr Ile Ile Lys Asp Pro Tyr Lys
65                  70                  75                  80

Leu Leu Asp Leu Glu Lys Lys Lys Leu Gly Ser Tyr Lys Tyr Ile Gly
            85                  90                  95

Ala Ser Asp Asp Thr Ala Asn Asp Gly Tyr Tyr Lys Met Gly Leu Tyr
            100                 105                 110

Lys His Leu Val Lys Val Glu Ile Asp Lys Gly Lys Ala Lys Lys
            115                 120                 125

Glu Leu Lys Tyr Leu Pro Phe Leu Ser Gln Lys Glu Tyr Leu Val Lys
            130                 135                 140

Val Tyr Thr Asp Leu Lys Lys Ile Asn Asn Cys Gln Glu Lys Lys Glu
145                 150                 155                 160

Glu Val Lys Leu Asp Tyr Lys Met Asp Glu Leu Tyr Lys Ser Lys Val
            165                 170                 175

Lys Ser Ser Gly Leu Leu Glu Lys Leu Met Ser Lys Leu Ile Glu Ser
            180                 185                 190

Lys Leu Ser Leu Leu Asn Val Gln Thr Gln Leu Met Ser Ser Glu His
            195                 200                 205

Cys Ile Asp Thr Asn Val Pro Asn Ala Ala Cys Tyr Arg Tyr Leu Asp
            210                 215                 220

Gly Thr Glu Glu Trp Arg Cys Leu Leu Phe Lys Glu Gly Lys Cys Val
```

-continued

```
                225                 230                 235                 240
Pro Ala Asn Thr Cys Lys Asp Asn Gly Gly Cys Ala Pro Glu Ala Glu
                245                 250                 255

Cys Lys Met Asp Asn Ile Val Cys Lys Cys Thr Lys Glu Gly Ser Glu
            260                 265                 270

Pro Leu Phe Glu Gly Val Phe Cys Ser
        275                 280

<210> SEQ ID NO 38
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 38

Leu Asn Val Gln Thr Gln
1               5
```